United States Patent
Ye et al.

(10) Patent No.: US 11,918,550 B2
(45) Date of Patent: Mar. 5, 2024

(54) SENSITIZATION OF CANCER CELLS TO DIFFERENTIATION THERAPY WITH MITOCHONDRIAL UNCOUPLER NICLOSAMIDE ETHANOLAMINE

(71) Applicant: The Board of Trustees of the Leland Stanford Junior University, Stanford, CA (US)

(72) Inventors: Jiangbin Ye, Stanford, CA (US); Haowen Jiang, Stanford, CA (US); Yang Li, Sunnyvale, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 55 days.

(21) Appl. No.: 17/542,145

(22) Filed: Dec. 3, 2021

(65) Prior Publication Data
US 2022/0175704 A1    Jun. 9, 2022

Related U.S. Application Data

(60) Provisional application No. 63/238,630, filed on Aug. 30, 2021, provisional application No. 63/123,243, filed on Dec. 9, 2020.

(51) Int. Cl.
| | |
|---|---|
| *A61K 31/167* | (2006.01) |
| *A61K 31/06* | (2006.01) |
| *A61K 31/203* | (2006.01) |
| *A61K 31/225* | (2006.01) |
| *A61P 35/00* | (2006.01) |

(52) U.S. Cl.
CPC ............ *A61K 31/167* (2013.01); *A61K 31/06* (2013.01); *A61K 31/203* (2013.01); *A61K 31/225* (2013.01); *A61P 35/00* (2018.01)

(58) Field of Classification Search
CPC .... A61K 31/167; A61K 31/06; A61K 31/203; A61K 31/225; A61P 35/00
USPC ......................................................... 514/622
See application file for complete search history.

(56) References Cited

U.S. PATENT DOCUMENTS

2020/0261393 A1    8/2020  Ye

OTHER PUBLICATIONS

Cancer [online], [retrieved on Jul. 6, 2007] Retrieved from the Internet, URL: http://www.nlm.nih.gov/medlineplus/cancer.html (Year: 2007).*
Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science (1999), vol. 286, 531-537 (Year: 1999).*
Li el al., (2020) "Metabolic Profiling Reveals a Dependency of Human Metastatic Breast Cancer on Mitochondrial Serine and One-Carbon Unit Metabolism", Mol Cancer Res, vol. 18, No. 4, pp. 599-611.
Li et al., (2020) "Acetate supplementation restores chromatin accessibility and promotes tumor cell differentiation under hypoxia", Cell Death Dis, 11:102.

* cited by examiner

*Primary Examiner* — Kristin A Vajda
(74) *Attorney, Agent, or Firm* — Pamela J. Sherwood; Bozicevic, Field and Francis LLP

(57) ABSTRACT

Methods are provided for the treatment of cancer by administering a mitochondrial uncoupler in a dose effective to increase differentiation of the cancer cells, which may be provided in a combination with a retinoic acid to differentiate the cancer cells. The effect on the targeted cancer cell is enhanced relative to a regimen in which a single agent is used; and the effect may be synergistic relative to a regimen in which a single agent is used. The cancer may be resistant to retinoic acid.

15 Claims, 49 Drawing Sheets

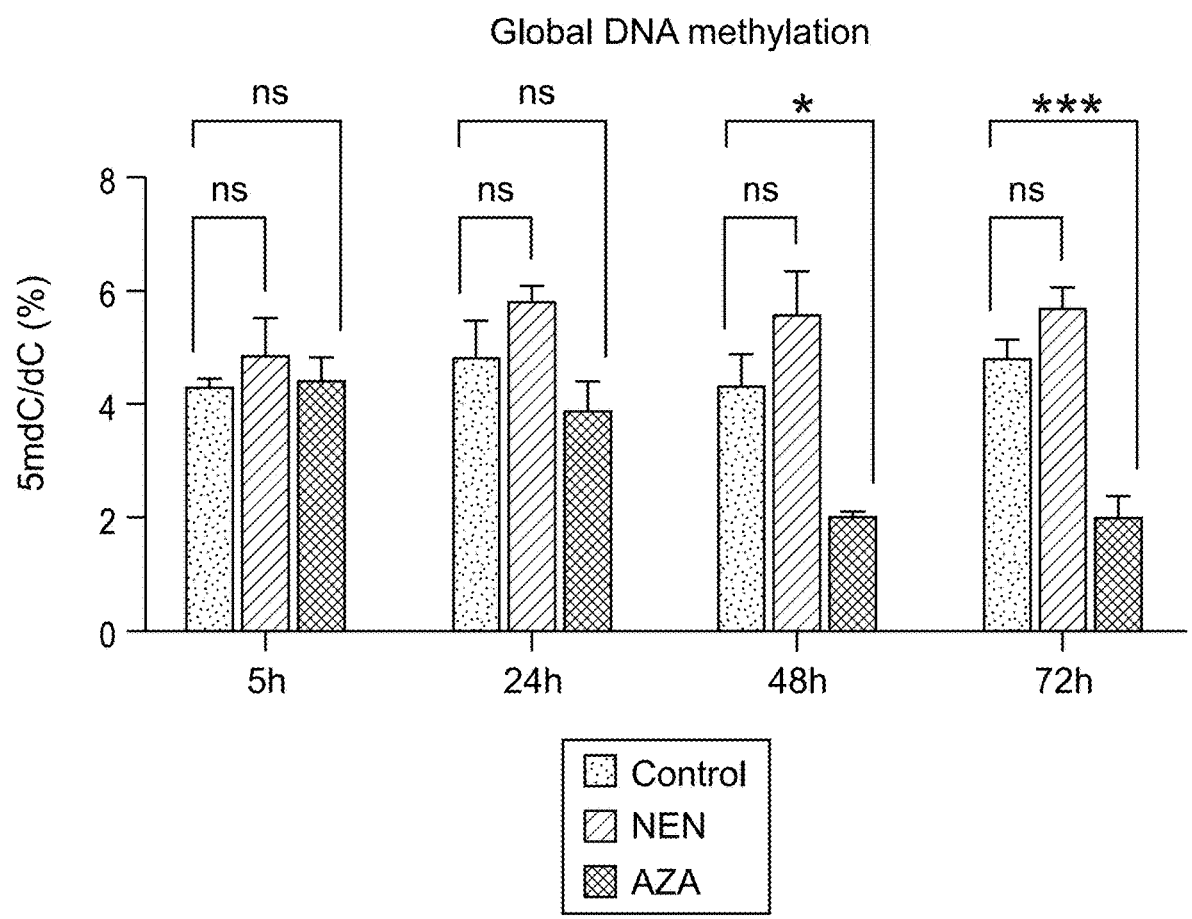

c (Cont.)

h i j c d

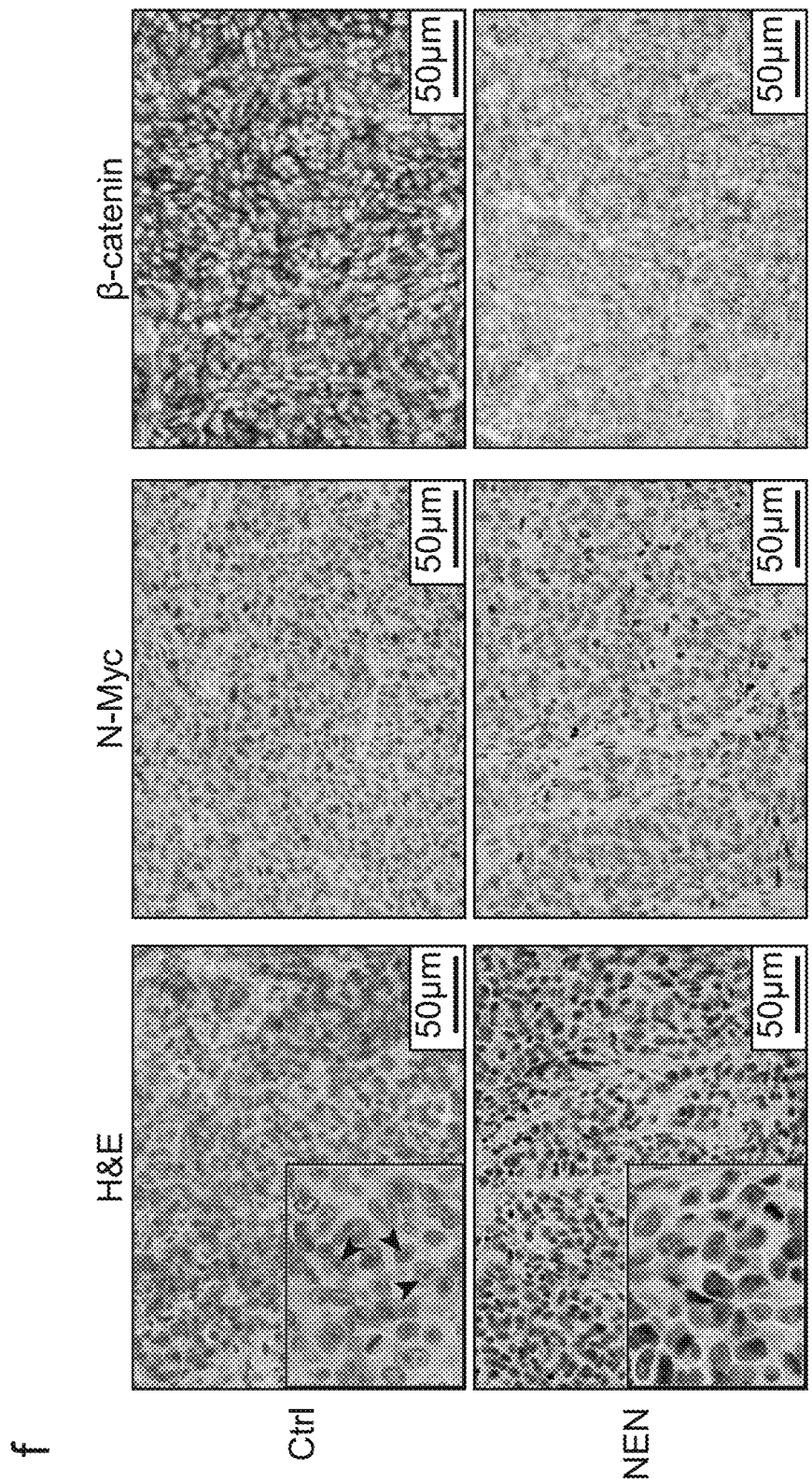

b b (Cont.)

a b b c e (Cont.)

f

**SK-N-BE(2)
3 days**

**SK-N-BE(2)
6 days**

SENSITIZATION OF CANCER CELLS TO DIFFERENTIATION THERAPY WITH MITOCHONDRIAL UNCOUPLER NICLOSAMIDE ETHANOLAMINE

CROSS REFERENCE

This application claims benefit of U.S. Provisional Patent Application No. 63/238,630, filed Aug. 30, 2021 and U.S. Provisional Patent Application No. 63/123,243, filed Dec. 9, 2020, which applications are incorporated herein by reference in their entirety.

STATEMENT REGARDING FEDERALLY SPONSORED RESEARCH

This invention was made with Government support under contracts HL157540 and OD029586 awarded by the National Institutes of Health. The Government has certain rights in the invention.

BACKGROUND

Neuroblastoma (NB) is derived from the neural crest cells that fail to exit the cell cycle and differentiate. Most neuroblastomas occur spontaneously, but a small percentage appear to be inherited. Some markers such as MYCN oncogene amplification, hyperdiploidy, histopathology correlate with progression and prognosis. About 40 to 50% of children have localized or regional disease at diagnosis; 50 to 60% have metastases at diagnosis. Neuroblastoma may metastasize to bone marrow, bone, liver, lymph nodes, or, less commonly, skin or brain.

Neuroblastoma accounts for 7% of all childhood cancers and 15% of childhood cancer-related deaths, with an incidence of over 600 cases per year in the U.S. Over 50% of NB cases present with metastasis. In high-risk patients, disease relapse occurs frequently after surgery or chemotherapy and eventually becomes fatal. This necessitates the development of alternative strategies for effective treatment. Retinoic acids (RA) are chemicals that derived from vitamin A, which has been used to induce differentiation in neuroblastoma cells for over 15 years. However, not all neuroblastoma patients benefit from retinoid therapy. About 50% of neuroblastoma patients who initially respond to RA therapy develop RA-resistance. Epigenetic silencing of retinoic acid receptor (RAR) signaling through DNA methylation is one of the major causes of RA-resistance.

Novel therapy strategy is urgently needed to eliminate RA-resistance of cancer.

SUMMARY

Methods are provided for a combination therapy to efficiently differentiate cancer cells. The methods comprise administering an effective dose of a mitochondrial uncoupler to sensitize the cancer cells to differentiation therapy. In some embodiments the mitochondrial uncoupler is oxyclozanide or dinitrophenol (DNP). In some embodiments the mitochondrial uncoupler is niclosamide ethanolamine (NEN), which is is a cell-permeable, orally bioavailable, non-toxic salt form of niclosamide that acts as a reversible, mild uncoupler of mitochondria. NEN reprograms global DNA methylation and restores retinoic acid receptor expression to overcome retinoic acid resistance in cancer cells. In some embodiments the differentiation therapy comprises administering an effective dose of an a retinoic acid. The therapy may further comprise one or both of an effective dose of α-ketoglutarate, and an acetate supplementation agent, e.g. glyceryltriacetate (GTA). In some embodiments, the combination therapy is administered in the absence of additional agents. In other embodiments additional anti-cancer agents are administered. In some embodiments the cancer to be treated is resistant to retinoic acid therapy in the absence of the treatment.

The therapeutic forms of RA include all trans retinoic acid (ATRA, tretinoin); 9-cis-retinoic acid (Alitretinoin); and 13-cis-retinoic acid (Isotretinoin). In some embodiments the retinoic acid is 13-cis-retinoic acid.

According to another embodiment, articles of manufacture are provided. The articles of manufacture, also referred to as kits, include packaging material and a therapeutic combination of niclosamide ethanolamine (NEN) and a retinoic acid, wherein the article of manufacture also includes a label or package insert. According to another aspect of the invention, use of a niclosamide ethanolamine in the manufacture of a medicament for the treatment of cancer is provided.

Without being limited by the theory, it is believed that treatment with niclosamide ethanolamine (NEN) increases the intracellular α-ketoglutarate (αKG) level and the ratio of αKG/2-hydroxyglutarate (2-HG) through accelerating glutaminolysis. NEN treatment reduces 2-HG levels under both normoxia and hypoxia. NEN treatment also blocks reductive carboxylation to conserve αKG. These metabolic reprogramming effects alter DNA methylation, increase p53 expression, repress β-catanin and N-Myc expression, and restores RAR expression, eliminating RA-resistance in cancer cells. GTA in combination with RA and αKG or NEN further enhanced the change in differentiation with a synergistic effect on activating RA signaling and differentiation in these cells. In some embodiments NEN is administered to decrease methylation of a cancer cell. In some embodiments NEN is administered to decrease methylation of a normal (non-cancerous) cell.

A benefit of the present invention can be the use of lowered doses of the agents relative to the dose required as a single agent. A benefit of the present invention can also, or alternatively, be a decrease in the length of time required for treatment, relative to the length of time required for treatment as a single agent. A benefit of the present invention can also, or alternatively, be an enhanced response relative to the response observed after treatment with a single agent.

Methods of administration include, without limitation, oral administration, systemic administration, intra-tumoral administration, etc. Usually the active agent (i) is administered within about a period of about 45 days, about 30 days, about 21 days, about 14 days, about 10 days, about 8 days, about 7 days, about 6 days, about 5 days, about 4 days, about 3 days, about 2 days, about 1 day or substantially the same day as an agent (ii). In some embodiments an agent (i) is administered prior to an agent (ii). In some embodiments an agent (i) is administered after an agent (ii). The agents can be considered to be combined if administration scheduling is such that the serum level of both agents is at a therapeutic level at the same time. Administration may be repeated as necessary for differentiation of the cancer cell population.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

(FIG. 1c) Relative intracellular L-glutamine and L-glutamate levels were measured using LC/MS in SK-N-BE(2) cells and NB16 cells treated with DMSO or 1 μM NEN for 5 h. (FIG. 1d) Schematic of $^{13}$C-labeling patterns of TCA cycle metabolites froi U-$^{13}$C-glutamine. (FIG. 1e) SK-N-BE(2) and NB16 cells were pretreated by DMSO or 1 μM NEN for 3 h, then labeled with U-$^{13}$C-glutamine for 2 h. Relative isotopic labelling abundance in αKG, 2HG and the ratio of m+5 αKG/m+5 2HG were measured using LC/MS. Data represent mean±SEM (n=3, biologically repeats). Representative of at least two independent experiments. *P<0.05, P<0.01, *P<0.001. Two-sided Student's t-test.

(FIG. 2a) Quantification of global DNA methylation in SK-N-BE(2) cells treated by DMSO, 1 μM NEN or 1 μM 5-AZA for 5 h, 24 h and 48 h by using the LC-MS. (FIG. 2b) The differential methylation changes were annotated to specific region in SK-N-BE(2) cells treated with DMSO or 1 μM NEN for 24 or 48 hours. (FIG. 2c) The differential methylated CpG sites were presented in the heatmap.

(FIG. 3a) Number of genes differentially expressed with a sleuth q-value<0.05 and fold change estimate b>abs (ln(2)) and (FIG. 3b) The distribution of the gene profile after NEN treatment for 16 hrs in SK-N-BE(2) cells. (FIG. 3c) The top 10 gene expression signature pathways enriched from upregulated genes from David analysis. (FIG. 3d) Immunofluorescence staining of β-tubulin III (Red) and DAPI (Blue) in SK-N-EB(2) and NB16 cells treated by DMSO, 1 μM NEN for 72 h. Scale bar: 25 μm. (FIG. 3e) Left: morphological feature of NB16 and SK-N-BE(2) cells treated by DMSO or 1 μM NEN for 96 h (Scale bar: 50 μM). Right: Quantification of neurite outgrowth with NeuronJ. (FIG. 3f) The top 10 gene expression signatures enriched from downregulated genes from David analysis. (FIG. 3g) Cells were plated in 12 wells plates (2×10$^4$ cells/well). After 24 hrs, cells were treated with DMSO or 1 μM NEN for 3 days, and then counted. (FIG. 3h) GSEA of E2F targets and G2M checkpoints pathways genes from the RNA-seq (n=3) experiments in SK-N-BE(2) cells. (FIG. 3i) mRNA and protein levels of N-myc were examined in SK-N-BE(2) cells treated with 1 μM NEN for indicated time. (FIG. 3j) GSEA of N-myc targets pathway genes from the RNA-seq (n=3) experiments in SK-N-BE(2) cells.

(FIG. 4a) Heatmap of genes expression of wnt signaling pathway from the RNA-seq (n=3) experiments in SK-N-BE (2) cells. (FIG. 4b) qPCR analysis (n=3) were employed to validate the RNA-seq data in SK-N-BE(2) cells. (FIG. 4c) The protein expression level of nuclear β-catenin of SK-N-BE(2) and NB16 cells were examined by western blot treated by DMSO, 1 μM NEN for 24 and 48 hrs. (FIG. 4d) GSEA of p53 pathways genes from the RNA-seq (n=3) experiments in SK-N-BE(2) cells. (FIG. 4e) The DNA methylation profile changes in ctnnbip1 and tp53 promoter were determined by EPIC methylation array in SK-N-BE(2) cells treated with DMSO or 1 μM NEN for 24 h.

FIG. 5a-FIG. 5. c. NEN treatment decreased the reductive carboxylation. (FIG. 5a) Schematic of carbon atom (circles) transitions from U-$^{13}$C-glutamine (blue) and 1-$^{13}$C glutamine (yellow) into oxidation TCA cycle or reductive carboxylation. (FIG. 5b) SK-N-BE(2) and NB16 cells were pretreated by DMSO or 1 μM NEN for 3 h, then switched to medium contained same treatment in the presence of U-$^{13}$C-glutamine for 2 h. The Isotopomer distribution of citrate, malate, fumarate and aspartate from U-$^{13}$C-glutamine were measured using LC/MS. (FIG. 5c) SK-N-BE(2) cells were pretreated by DMSO or 1 μM NEN for 3 h under normoxia or hypoxia (0.5% oxygen), then switched to medium contained same treatment in the presence of 1-$^{13}$C-glutamine for 3 h. The Isotopomer distribution of citrate, malate and fumarate were measured using LC/MS. Data represent the mean±SEM from three biologically repeats. *P<0.05, P<0.01 and *P<0.001. Two-sided Student's t-test.

(FIG. 6a) Relative Intracellular metabolite level or ratio were measured by LC/MS in SK-N-BE(2) cells treated by DMSO under normoxia or DMSO/1 μM NEN under hypoxia for 3 h or 6 h. (FIG. 6b) The protein expression level of nuclear HIF1α and HIF2α of SK-N-BE(2) were examined by western blot treated by DMSO, 2 or 4 μM NEN, 3.5 mM α-KG for indicated time under normoxia or hypoxia. (FIG. 6c) The gene expression of pdk1, pdk3, pgk1 and ldha were determined by RT-PCR in SK-N-BE(2) cells treated by treated by DMSO, 2 or 4 μM NEN under normoxia or hypoxia. (FIG. 6d) Left panel: Morphological feature of SK-N-BE(2) cells treated by DMSO or 1 μM NEN under normoxia or hypoxia for 4 days (Scale bar: 50 μM). Right panel: cells from left panel were trypsinized and replated (2×10$^4$ cells/well) in 12 wells plates. Count the cells after 5 days. *P<0.05 P<0.01 and *P<0.00 for comparisons were calculated using a two-sided Student's t-test.

(FIG. 7a) The schematic of in vivo experiment. (FIG. 7b) The plasma NEN concentrations were measured by LC/MS. (FIG. 7c) Tissue NEN accumulation were measured by LC/MS. (d) Quantification of time to reach certain tumor volume on CTRL group (n=6) and NEN group (n=4). (e) Relative metabolite levels or ratios in the tumors were measured using LC/MS from control or NEN treatment group. (FIG. 7f) The tumors from CTRL and NEN treatment group were stained with H&E and processed for N-Myc and β-catenin immunohistochemistry staining. Nucleolar formation in the tumors cells were examined by H&E staining in both CTRL and Treatment group. The arrows point out the prominent nucleolar formation.

(FIG. 8a) The gene expression data generated by RNA-seq (n=3) was analyzed by using GSEA to perform enrichment in SK-N-BE(2) cells. The gene sets (favorable or unfavorable prognosis, p-value<0.05) were defined from 11 available neuroblastoma databases from R2. (FIG. 8b) Represented analysis plot from (a). (FIG. 8c) Overlap the favorable prognosis gene sets (p-value<0.05, gene number>1000) from 7 available neuroblastoma databases from R2. And the overlapped genes were submitted to David analysis. (FIG. 8d) Overlap the unfavorable prognosis gene sets (p-value<0.05, gene number>1000) from 7 available neuroblastoma databases from R2. And the overlapped genes were submitted to David analysis.

(FIG. 9a, FIG. 9b) Morphological feature of NB16 and SK-N-BE(2) cells treated by DMSO, 1 μM NEN, with or without 1 μM 13-cis-RA for 96 h. Scale bar: 50 μm and quantification of neurite outgrowth with NeuronJ, a plugin in the ImageJ package. (FIG. 9c) Immunofluorescence staining of β-tubulin III (Red) and DAPI (Blue) in NB16 and SK-N-EB(2) cells treated by DMSO, 1 μM NEN or without 1 μM 13-cis-RA for 72 h. Scale bar: 25 μm. (FIG. 9d) Heatmap of genes expression of RAR signaling in SK-N-EB(2) cells treated by DMSO, 1 μM NEN, 1 μM 13-cis-RA or NEN+RA for 16 hrs. Gene expression levels were determined by RNA-Seq (n=3). (FIG. 9e) qPCR analysis (n=3) were employed to validate the RNA-seq data in SK-N-BE(2) cells. (FIG. 9f) The protein expression levels of RA signaling proteins and N-Myc in SK-N-BE(2) cells treated by DMSO, 1 μM NEN, or 1 μM 5-AZA with or without 1 μM RA for 24 hrs were examined by western blot.

FIG. 11-FIG. 11b. NEN treatment reprograms glutamine metabolism. (FIG. 11a) SK-N-BE(2) and NB16 cells were pretreated by DMSO or 1 μM NEN for 3 h, then change the medium contained same treatment in the presence of U-$^{13}$C-glutamine for 2 h. Data represent mean±SEM (n=3, biologically repeats). Representative of at least two independent experiments. *P<0.05 P<0.01 and *P<0.001 Two-sided Student's t-test.

(FIG. 13a) 250 μg NEN in DMSO were delivered to mice through intraperitoneal injection. Blood sample were collected at the timepoints indicated from tail vein. The NEN concentration were measured using LC-MS (n=3). (b) Overlapping good prognosis genes (p-value<0.05, gene number>1000) of 7 available neuroblastoma datasets from R2 database. And the overlapping genes were submitted to David analysis. (c) Overlapping bad prognosis genes (p-value<0.05, gene number>1000) of 7 available neuroblastoma datasets from R2 database. And the overlapping genes were submitted to David analysis.

(FIG. 14a) $2\times10^4$ cells/well plated in the well of 12-well plate. After 24 hrs, cells were treated by DMSO or indicated concentration of 13-cis-RA. Then the cells were counted in 48 hrs and 96 hrs after treatment. The morphological changes were show 96 hrs after treatment. (FIG. 14b) The expression of RA receptors and N-myc under indicated concentration of RA treatment for 24 h between different neuroblastoma cells (Data in B and C are represented as mean±SD of three biological repeats. *P<0.05; P<0.01; *P<0.001, determined by Student's two-tailed t-test).

(FIG. 15a) Cells were plated in 12-well plates ($2\times10^4$ cells/well). After 24 h, cells were treated with as indicated for 3 days. (FIG. 15b) qPCR analysis (n=3) were employed to validate the RNA-seq data. (FIG. 15c) The protein expression level of RA signaling proteins and N-myc of NB16 cells were examined by western blot treated by DMSO, 1 μM NEN, or 1 μM 5-AZA with or without 1 μM RA for 24 hrs. (FIG. 15d) 500 cells/well were plated in the dish of 60 mm plate. After 24 hrs, cells were treated by DMSO, 1 μM NEN, with or without 1 μM RA. After two weeks, the cells fixed and stained by crystal violet. The quantification were done by using countPHICS. (FIG. 15e) SK-N-BE(2) cells were treated by DMSO or 1 μM NEN 5 hrs, then the methylation of promoter region of indicated genes were detected by performing Methylated-IP with 5mc or IgG antibody and followed with Q-PCR to analysis the output of this IP. The methylation were represent as the fold changes against the input genomic DNA. Some of the IgG output could not be detected by Q-PCR, and mark by N.D. (FIG. 15f) $2\times10^4$ cells/well plated in the well of 12-well plate. After 24 hrs, cells were treated by DMSO, 1 μM NEN, 2 Mm 5-AZA or 5 μM 5-AZA with or without 1 μM 13-cis-RA. The morphological changes were capture after 3 days and 6 days treatment.

DETAILED DESCRIPTION

Figure 1:
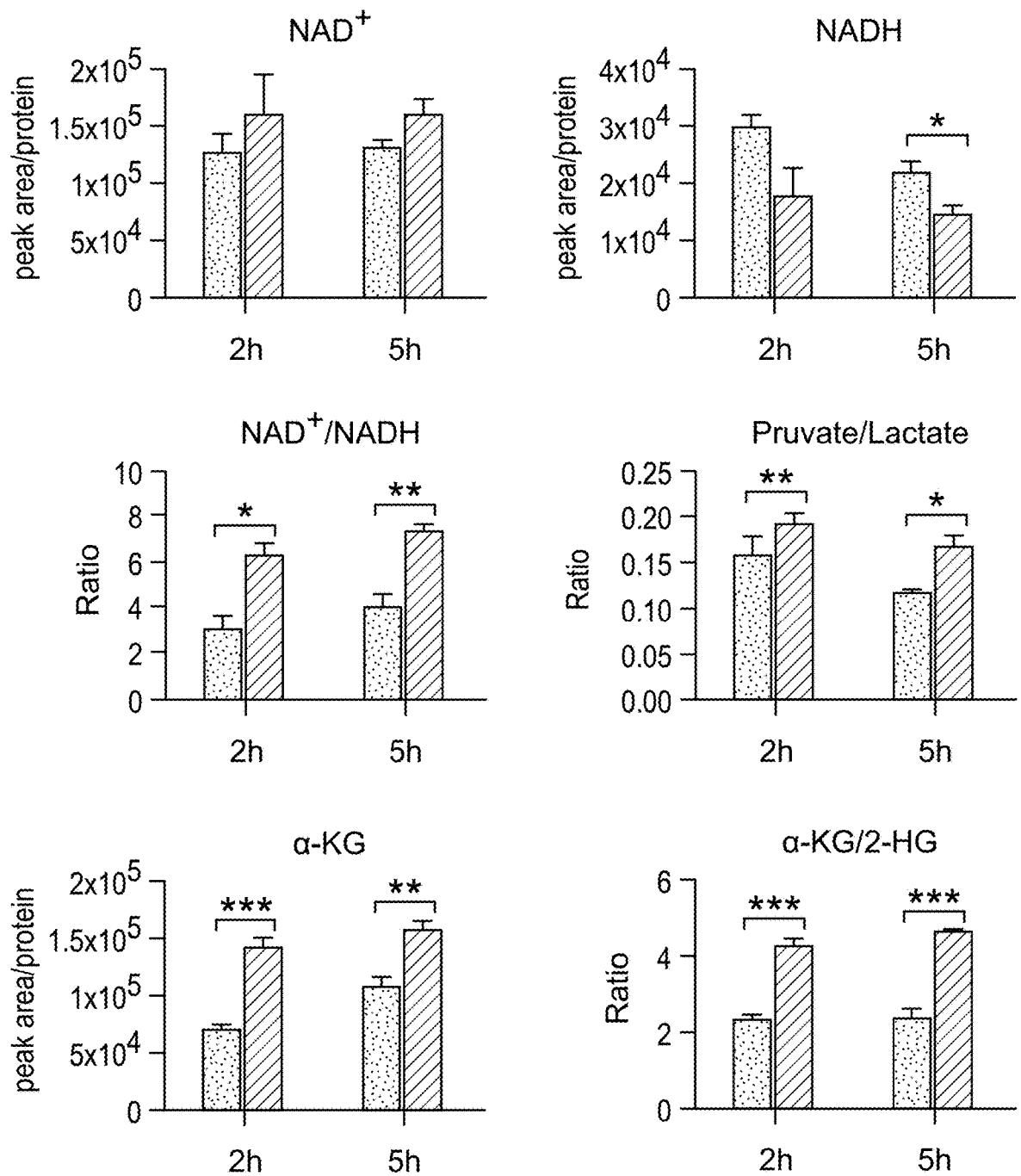
FIG. 1a-FIG. 1e. NEN treatment accelerates glutaminolysis to increase cellular αKG. Relative intracellular metabolite levels were measured using LC/MS in SK-N-BE(2) cells (FIG. 1a) and NB16 cells (FIG. 1b) treated with DMSO or 1 μM NEN for 2 h or 5 h.
Figure 1:
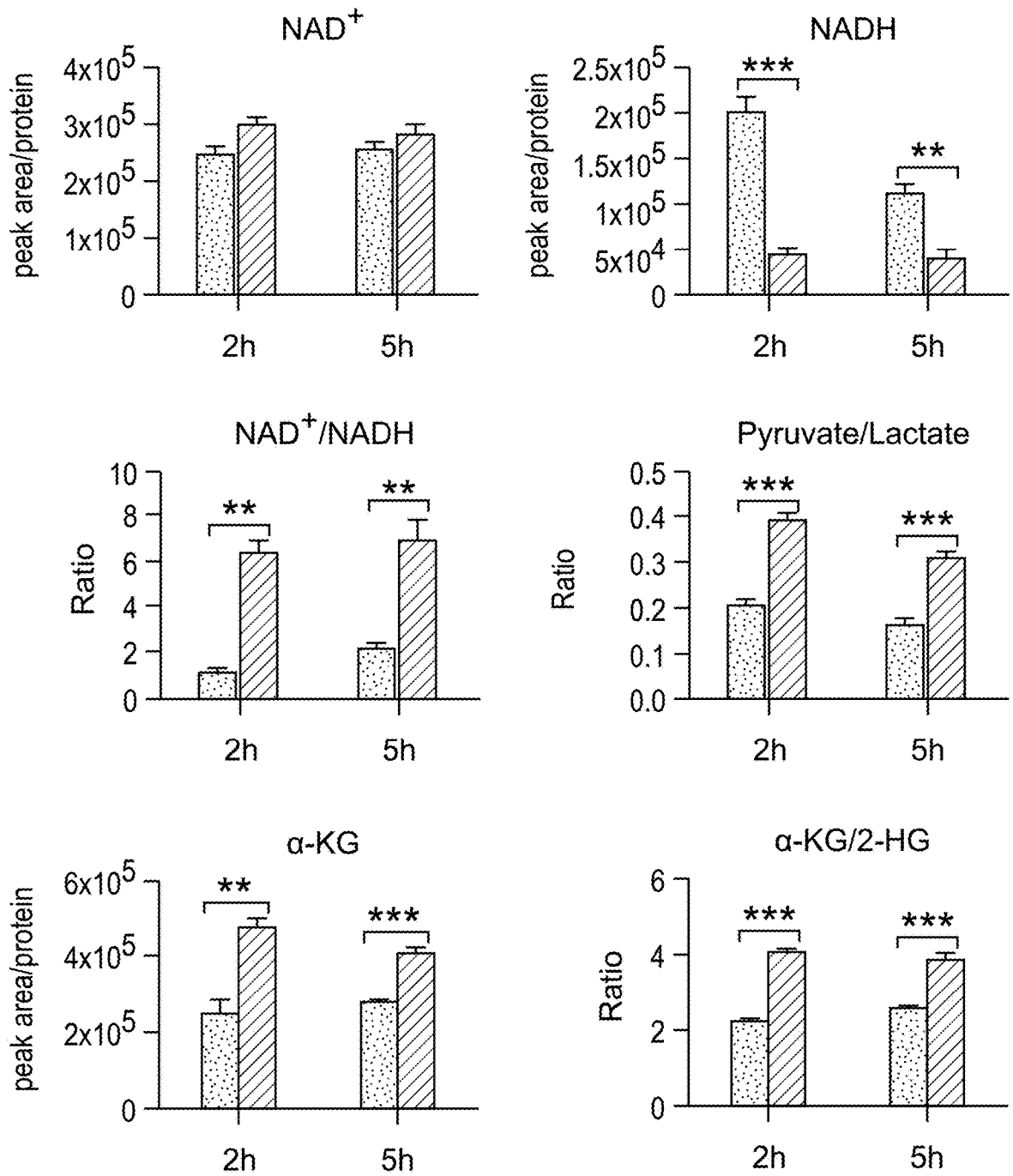
Figure 1:
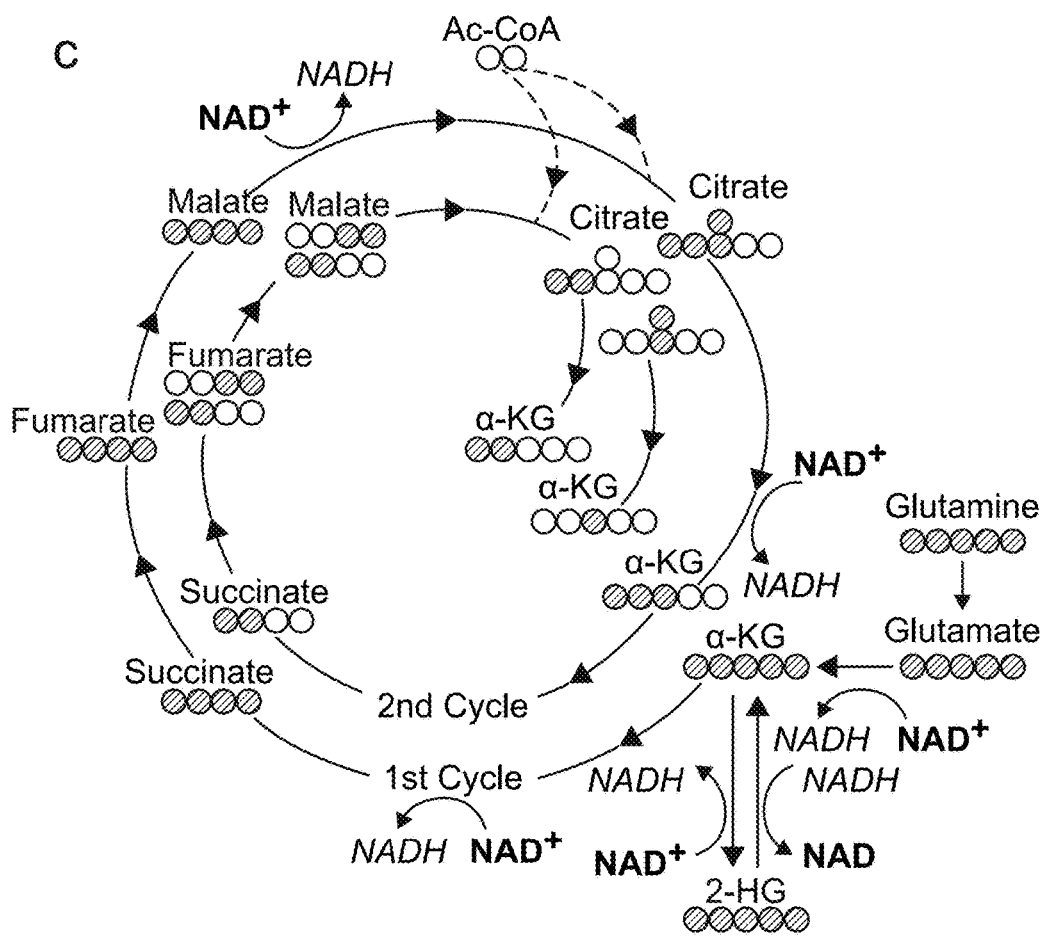
Figure 1:
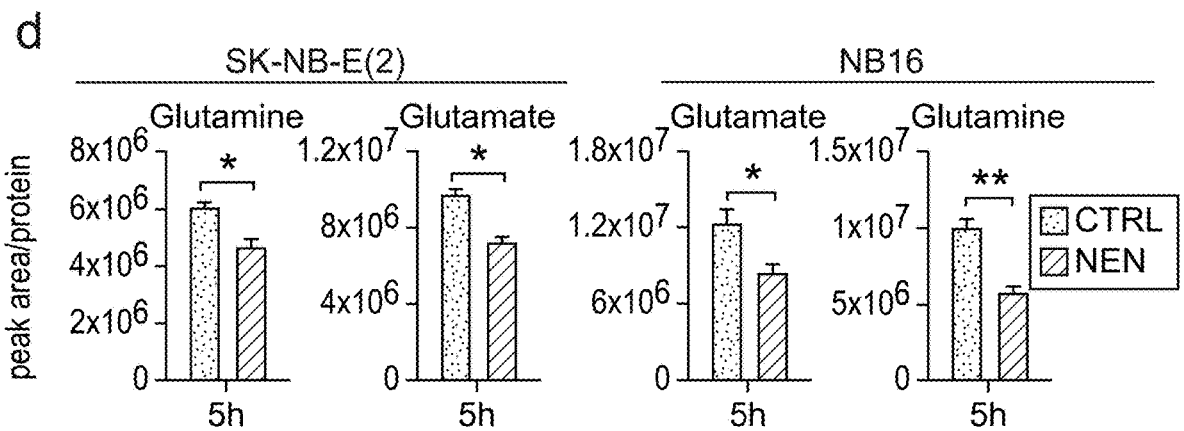
Figure 1:
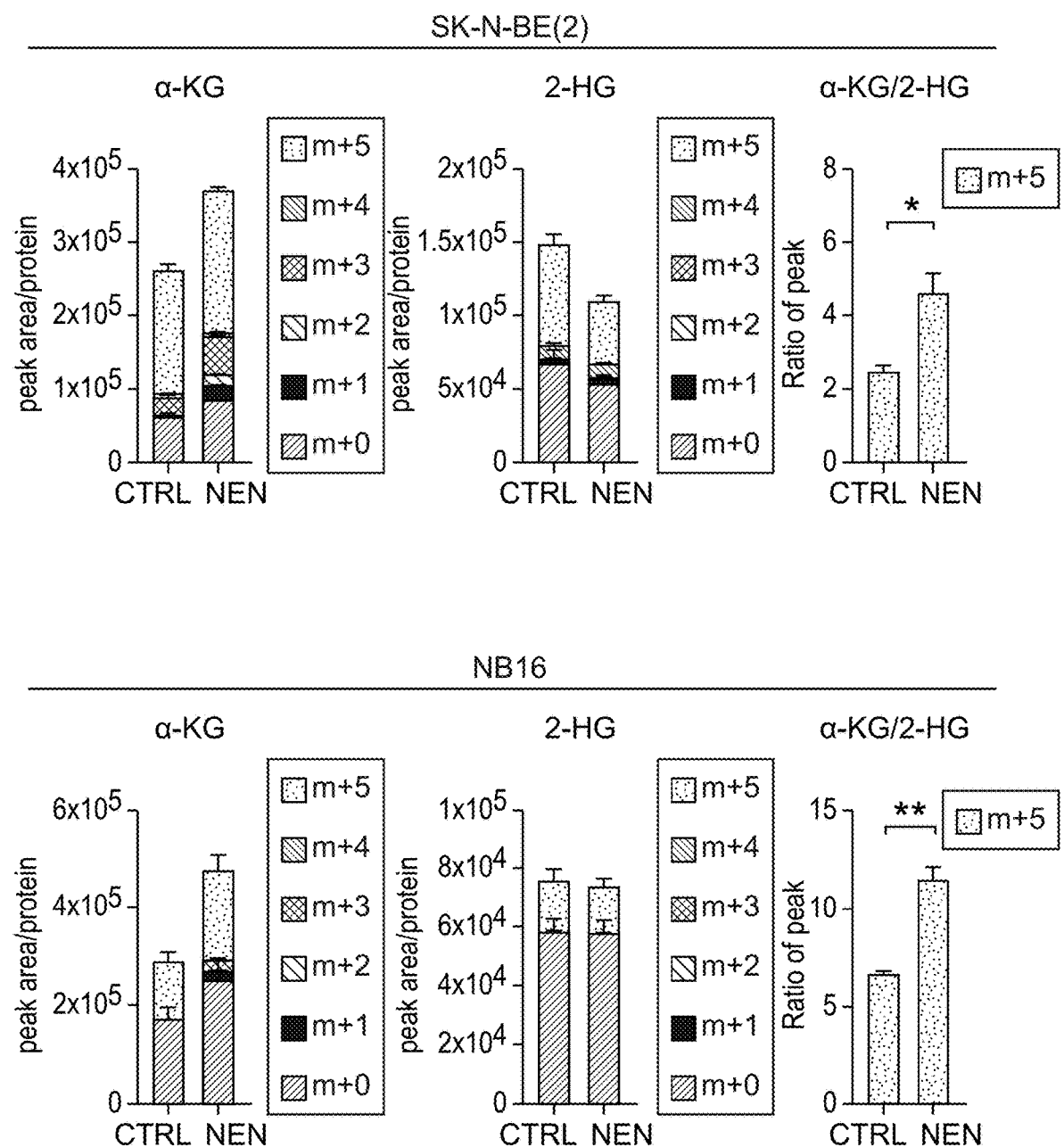

Methods are provided for the treatment of cancer by administering a combination of agents that provide for metabolic interventions, which induce differentiation of the cancer cells. In some embodiments, the combination of agents provides a synergistic effect relative to the administration of an agent as a monotherapy. In various embodiments, the combination of agents may be administered in a therapeutic regimen that includes conventional treatment, e.g. targeted anti-tumor antibodies, chemotherapy, radiation therapy, surgery, and the like.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer. In some embodiments the cancer is other than a glioma.

Cancers that have been treated with retinoic acid and that can benefit from NEN treatment include, without limitation, juvenile chronic myelogenous leukemia (CML), neuroblastoma, including high risk neuroblastoma, recurrent cervical cancer, squamous cell head and neck cancer, and squamous cell skin carcinoma. In some embodiments the cancer is neuroblastoma. In some embodiments the neuroblastoma is high risk neuroblastoma. In some embodiments the cancer is RA-resistant prior to treatment with the combination therapy described herein.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable number of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of a cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of the agents described herein. When administered in combination, each component can be administered at the same time or sequentially in any order at different points in time. Thus, each component can be administered separately but sufficiently closely in time so as to provide the desired therapeutic effect.

"Concomitant administration" of active agents in the methods of the invention means administration with the reagents at such time that the agents will have a therapeutic effect at the same time. Such concomitant administration may involve concurrent (i.e. at the same time), prior, or subsequent administration of the agents. A person of ordinary skill in the art would have no difficulty determining the appropriate timing, sequence and dosages of administration for particular drugs and compositions of the present invention.

As used herein, endpoints for treatment will be given a meaning as known in the art and as used by the Food and Drug Administration.

Overall survival is defined as the time from randomization until death from any cause, and is measured in the intent-to-treat population. Survival is considered the most reliable cancer endpoint, and when studies can be conducted to adequately assess survival, it is usually the preferred endpoint. This endpoint is precise and easy to measure, documented by the date of death. Bias is not a factor in endpoint measurement. Survival improvement should be analyzed as a risk-benefit analysis to assess clinical benefit. Overall survival can be evaluated in randomized controlled studies. Demonstration of a statistically significant improvement in overall survival can be considered to be clinically significant if the toxicity profile is acceptable, and has often supported new drug approval. A benefit of the methods of the invention can include increased overall survival of patients.

Endpoints that are based on tumor assessments include DFS, ORR, TTP, PFS, and time-to-treatment failure (TTF). The collection and analysis of data on these time-dependent endpoints are based on indirect assessments, calculations, and estimates (e.g., tumor measurements). Disease-Free Survival (DFS) is defined as the time from randomization until recurrence of tumor or death from any cause. The most frequent use of this endpoint is in the adjuvant setting after definitive surgery or radiotherapy. DFS also can be an important endpoint when a large percentage of patients achieve complete responses with chemotherapy.

Objective Response Rate. ORR is defined as the proportion of patients with tumor size reduction of a predefined amount and for a minimum time period. Response duration usually is measured from the time of initial response until documented tumor progression. Generally, the FDA has defined ORR as the sum of partial responses plus complete responses. When defined in this manner, ORR is a direct measure of drug antitumor activity, which can be evaluated in a single-arm study.

Time to Progression and Progression-Free Survival. TTP and PFS have served as primary endpoints for drug approval. TTP is defined as the time from randomization until objective tumor progression; TTP does not include deaths. PFS is defined as the time from randomization until objective tumor progression or death. The precise definition of tumor progression is important and should be carefully detailed in the protocol.

Niclosamide ethanolamine (NEN) increases levels of the RA receptor (RARα and RARγ) in a cell. Treatment with NEN increased the intracellular α-ketoglutarate (αKG) level and the ratio of αKG/2-hydroxyglutarate (2-HG) through accelerating glutaminolysis. This metabolic reprogramming decreased DNA methylation and restored the RA-receptor expression, eliminating RA-resistance in cancer cells.

Niclosamide ethanolamine is also referred to as Clonitralid; Niclosamidel; Bayluscide; Mollutox; Baylucit; Phenasal ethanolamine salt; Bayer 25648; 5-chloro-N-(2-chloro-4-nitrophenyl)-2-hydroxybenzamide compound with 2-aminoethanol (1:1); 5,2'-Dichloro-4'-nitrosalicylanilide; Salicylanilide, 2',5-dichloro-4'-nitro-, ethanolamine salt. It has the structure:

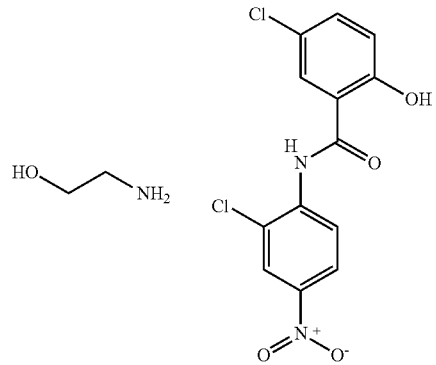

NEN can be orally administered. The dosage may be, for example, a fixed dose of 25, at least 50, at least 75, at least 100, at least 250, at least 500, at least 750, at least 1000, at least 2000, at least 3000, at least 4000 mgdaily. Administration on a weight basis may be from about 1 mg/kg, about 5 mg/kg, about 10 mg/kg, about 25 mg/kg, about 50 mg/kg, about 100 mg/kg, about 250 mg/kg, up to about 1000 mg/kg, up to about 500 mg/kg, up to about 250 mg/kg.

In some embodiments, the total amount of NEN administered to the subject in a single day is between 5 to 100 g/kg body weight. In certain embodiments, the NEN is administered to the subject more than once and wherein the frequency of administration is at least once per month, once per week, every other day, or once per day. In some embodiments, the NEN is administered to the subject in a pharmaceutical composition. In some embodiments, the subject is a human. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. In some embodiments, a maximum dose can be used, that is, the highest safe dose according to sound medical judgment.

Multiple doses of compounds of the invention are also contemplated. In some instances, a compound of the invention, (e.g. NEN) can be administered at least daily, every other day, weekly, every other week, monthly, etc. Doses may be administered once per day or more than once per day, for example, 2, 3, 4, 5, or more times in one 24 hour period.

Retinoic acid (RA). Retinoic acid is a metabolite of vitamin A (retinol) that mediates the functions of vitamin A required for growth and development. The therapeutic forms of RA include all trans retinoic acid (ATRA, tretinoin); 9-cis-retinoic acid (Alitretinoin); and 13-cis-retinoic acid (Isotretinoin). 13-cis-retinoic acid is most commonly used for the treatment of neuroblastoma.

Retinoic acid acts by binding to the retinoic acid receptor (RAR), which is bound to DNA as a heterodimer with the retinoid X receptor (RXR) in regions called retinoic acid response elements (RAREs). Retinoic acid receptors mediate transcription of different sets of genes controlling differentiation of a variety of cell types, thus the target genes regulated can provide for differentiation of cancer cells to a non-pathogenic phenotype. As demonstrated herein, the effectiveness on the desired target genes is improved with NEN treatment.

Administration of RA is usually oral. Where the RA is isotretinoin, the dosage may range from at least 10, at least 25, least 50, at least 100, at least 200 and up to about 1000, up to about 750, up to about 500 mg/m$^2$/day.

Dosage of isotretinoin for the treatment of CML may be, for example, 100 mg/m$^2$/day orally, and up to 200 mg/m$^2$/day. Complete response for CML may be defined as white blood cell (WBC) normalization and resolution of organomegaly and partial response may be defined as a greater than 50% decrease in WBC count and organomegaly. An example of dosage of isotretinoin for the treatment of neuroblastoma may be, for example, 160 mg/m$^2$/day PO divided in 2 divided doses for 14 days repeated every 28 days for 6 cycles. An example of isotretinoin for the treatment of recurrent cervical cancer may be, for example, 1 mg/kg/day PO (rounded to the nearest 10 mg) divided into 2 doses. An example of dosage of isotretinoin for the treatment of squamous cell carcinoma is 50 mg/m$^2$/day PO, or 1 mg/kg/day PO. Isotretinoin is often administered in combination with interferon alfa, which may be administered in combination with NEN.

Acetate supplementation Agent. An acetate supplementation agent increases levels of acetate in a cell, and may be administered in combination with NEN and RA. In some embodiments the agent is a glyceryltriacetate (GTA). GTA is a triglyceride 1,2,3-triacetoxypropane and is also known at least as triacetin; glyceryltriacetate, glycerin triacetate; 1,2,3-propanetriyl triacetate; Enzactin; Fungacetin, Glycerin triacetate; Triacetylglycerol; glycerol triacetate; Glyped; kesscoflex TRA; Tracetine; Vanay, Glycerol triacetate tributyrin; triacetyl glycerine; and Propane-1,2,3-triyl triacetate.

GTA can be orally administered. The dosage may be, for example, at least 25, at least 50, at least 75, at least 100, at least 250, at least 500, at least 750, at least 1000, at least 2000, at least 3000, at least 4000 mg/kg/daily, and may be up to 5000 mg/kg, up to 4000, up to 3000, up to 2000, up to 1000 mg/kg/daily.

In some embodiments, the total amount of GTA compound administered to the subject in a single day is between 0.1 and 100 g/kg body weight. In certain embodiments, the GTA compound is administered to the subject more than once and wherein the frequency of administration is at least once per month, once per week, every other day, or once per day. In some embodiments, the GTA compound is administered to the subject in a pharmaceutical composition. In some embodiments, the subject does not have Canavan disease. In some embodiments, the subject is a human. In certain embodiments, the subject is not undergoing treatment with the GTA compound for a non-cancer indication. In some embodiments, the subject is free of any indications otherwise calling for treatment with the GTA compound.

In embodiments of the invention, an amount of GTA compound in a dose administered to a subject as a treatment for a cancer is significantly higher than an amount of GTA suitable for use as a pharmaceutical excipient or carrier, for example, for inclusion in a pharmaceutical product as an excipient or carrier for an active pharmaceutical ingredient. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. In some embodiments, a maximum dose can be used, that is, the highest safe dose according to sound medical judgment.

Multiple doses of compounds of the invention are also contemplated. In some instances, a compound of the invention, (e.g. GTA) can be administered at least daily, every other day, weekly, every other week, monthly, etc. Doses may be administered once per day or more than once per day, for example, 2, 3, 4, 5, or more times in one 24 hour period.

The term "isolated" refers to a molecule that is substantially free of its natural environment. For instance, an isolated protein is substantially free of cellular material or other proteins from the cell or tissue source from which it is derived. The term refers to preparations where the isolated protein is sufficiently pure to be administered as a therapeutic composition, or at least 70% to 80% (w/w) pure, more preferably, at least 80%-90% (w/w) pure, even more preferably, 90-95% pure; and, most preferably, at least 95%, 96%, 97%, 98%, 99%, or 100% (w/w) pure. A "separated" compound refers to a compound that is removed from at least 90% of at least one component of a sample from which the compound was obtained. Any compound described herein can be provided as an isolated or separated compound.

The terms "subject," "individual," and "patient" are used interchangeably herein to refer to a mammal being assessed for treatment and/or being treated. In some embodiments, the mammal is a human. The terms "subject," "individual," and "patient" encompass, without limitation, individuals having a disease. Subjects may be human, but also include other mammals, particularly those mammals useful as laboratory models for human disease, e.g., mice, rats, etc.

The term "sample" with reference to a patient encompasses blood and other liquid samples of biological origin, solid tissue samples such as a biopsy specimen or tissue cultures or cells derived therefrom and the progeny thereof. The term also encompasses samples that have been manipulated in any way after their procurement, such as by treatment with reagents; washed; or enrichment for certain cell populations, such as diseased cells. The definition also includes samples that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's diseased cell, e.g., a sample comprising polynucleotides and/or polypeptides that is obtained from a patient's diseased cell (e.g., a cell lysate or other cell extract comprising polynucleotides and/or polypeptides); and a sample comprising diseased cells from a patient. A biological sample comprising a diseased cell from a patient can also include non-diseased cells.

The term "diagnosis" is used herein to refer to the identification of a molecular or pathological state, disease or condition in a subject, individual, or patient.

The term "prognosis" is used herein to refer to the prediction of the likelihood of death or disease progression, including recurrence, spread, and drug resistance, in a subject, individual, or patient. The term "prediction" is used herein to refer to the act of foretelling or estimating, based on observation, experience, or scientific reasoning, the likelihood of a subject, individual, or patient experiencing a particular event or clinical outcome. In one example, a physician may attempt to predict the likelihood that a patient will survive.

As used herein, the terms "treatment," "treating," and the like, refer to administering an agent, or carrying out a procedure, for the purposes of obtaining an effect on or in a subject, individual, or patient. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of cancer in a mammal, particularly in a human, and includes: (a) inhibiting the disease, i.e., arresting its development; and (b) relieving the disease or its symptoms, i.e., causing regression of the disease or its symptoms.

Treating may refer to any indicia of success in the treatment or amelioration or prevention of a disease, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of engineered cells to prevent or delay, to alleviate, or to arrest or inhibit development of the symptoms or conditions associated with disease or other diseases. The term "therapeutic effect" refers to the reduction, elimination, or prevention of the disease, symptoms of the disease, or side effects of the disease in the subject.

As used herein, a "therapeutically effective amount" refers to that amount of the therapeutic agent sufficient to treat or manage a disease or disorder. A therapeutically effective amount may refer to the amount of therapeutic agent sufficient to delay or minimize the onset of disease, e.g., to delay or minimize the growth and spread of cancer. A therapeutically effective amount may also refer to the amount of the therapeutic agent that provides a therapeutic benefit in the treatment or management of a disease. Further, a therapeutically effective amount with respect to a therapeutic agent of the invention means the amount of therapeutic agent alone, or in combination with other therapies, that provides a therapeutic benefit in the treatment or management of a disease.

As used herein, the term "dosing regimen" refers to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

"In combination with", "combination therapy" and "combination products" refer, in certain embodiments, to the concurrent administration to a patient of the engineered proteins and cells described herein in combination with additional therapies, e.g. surgery, radiation, chemotherapy, and the like. When administered in combination, each component can be administered at the same time or sequentially in any order at different points in time. Thus, each component can be administered separately but sufficiently closely in time so as to provide the desired therapeutic effect.

"Concomitant administration" means administration of one or more components, such as engineered proteins and cells, known therapeutic agents, etc. at such time that the combination will have a therapeutic effect. Such concomitant administration may involve concurrent (i.e. at the same time), prior, or subsequent administration of components. A person of ordinary skill in the art would have no difficulty determining the appropriate timing, sequence and dosages of administration.

The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder.

Chemotherapy may include Abitrexate (Methotrexate Injection), Abraxane (Paclitaxel Injection), Adcetris (Brentuximab Vedotin Injection), Adriamycin (Doxorubicin), Adrucil Injection (5-FU (fluorouracil)), Afinitor (Everolimus), Afinitor Disperz (Everolimus), Alimta (PEMET EXED), Alkeran Injection (Melphalan Injection), Alkeran Tablets (Melphalan), Aredia (Pamidronate), Arimidex (Anastrozole), Aromasin (Exemestane), Arranon (Nelarabine), Arzerra (Ofatumumab Injection), Avastin (Bevacizumab), Bexxar (Tositumomab), BiCNU (Carmustine), Blenoxane (Bleomycin), Bosulif (Bosutinib), Busulfex Injection (Busulfan Injection), Campath (Alemtuzumab), Camptosar (Irinotecan), Caprelsa (Vandetanib), Casodex (Bicalutamide), CeeNU (Lomustine), CeeNU Dose Pack (Lomustine), Cerubidine (Daunorubicin), Clolar (Clofarabine Injection), Cometriq (Cabozantinib), Cosmegen (Dactinomycin), CytosarU (Cytarabine), Cytoxan (Cytoxan), Cytoxan Injection (Cyclophosphamide Injection), Dacogen (Decitabine), DaunoXome (Daunorubicin Lipid Complex Injection), Decadron (Dexamethasone), DepoCyt (Cytarabine Lipid Complex Injection), Dexamethasone Intensol (Dexamethasone), Dexpak Taperpak (Dexamethasone), Docefrez (Docetaxel), Doxil (Doxorubicin Lipid Complex Injection), Droxia (Hydroxyurea), DTIC (Decarbazine), Eligard (Leuprolide), Ellence (Ellence (epirubicin)), Eloxatin (Eloxatin (oxaliplatin)), Elspar (Asparaginase), Emcyt (Estramustine), Erbitux (Cetuximab), Erivedge (Vismodegib), Erwinaze (Asparaginase *Erwinia chrysanthemi*), Ethyol (Amifostine), Etopophos (Etoposide Injection), Eulexin (Flutamide), Fareston (Toremifene), Faslodex (Fulvestrant), Femara (Letrozole), Firmagon (Degarelix Injection), Fludara (Fludarabine), Folex (Methotrexate Injection), Folotyn (Pralatrexate Injection), FUDR (FUDR (floxuridine)), Gemzar (Gemcitabine), Gilotrif (Afatinib), Gleevec (Imatinib Mesylate), Gliadel Wafer (Carmustine wafer), Halaven (Eribulin Injection), Herceptin (Trastuzumab), Hexalen (Altretamine), Hycamtin (Topotecan), Hycamtin (Topotecan), Hydrea (Hydroxyurea), Iclusig (Ponatinib), Idamycin PFS (Idarubicin), Ifex (Ifosfamide), Inlyta (Axitinib), Intron A alfab (Interferon alfa-2a), Iressa (Gefitinib), Istodax (Romidepsin Injection), Ixempra (Ixabepilone Injection), Jakafi (Ruxolitinib), Jevtana (Cabazitaxel Injection), Kadcyla (Ado-trastuzumab Emtansine), Kyprolis (Carfilzomib), Leukeran (Chlorambucil), Leukine (Sargramostim), Leustatin (Cladribine), Lupron (Leuprolide), Lupron Depot (Leuprolide), Lupron DepotPED (Leuprolide), Lysodren (Mitotane), Marqibo Kit (Vincristine Lipid Complex Injection), Matulane (Procarbazine), Megace (Megestrol), Mekinist (Trametinib), Mesnex (Mesna), Mesnex (Mesna Injection), Metastron (Strontium-89 Chloride), Mexate (Methotrexate Injection), Mustargen (Mechlorethamine), Mutamycin (Mitomycin), Myleran (Busulfan), Mylotarg (Gemtuzumab Ozogamicin), Navelbine (Vinorelbine), Neosar Injection (Cyclophosphamide Injection), Neulasta (filgrastim), Neulasta (pegfilgrastim), Neupogen (filgrastim), Nexavar (Sorafenib), Nilandron (Nilandron (nilutamide)), Nipent (Pentostatin), Nolvadex (Tamoxifen), Novantrone (Mitoxantrone), Oncaspar (Pegaspargase), Oncovin (Vincristine), Ontak (Denileukin Diftitox), Onxol (Paclitaxel Injection), Panretin (Alitretinoin), Paraplatin (Carboplatin), Perjeta (Pertuzumab Injection), Platinol (Cisplatin), Platinol (Cisplatin Injection), PlatinolAQ (Cisplatin), PlatinolAQ (Cisplatin Injection), Pomalyst (Pomalidomide), Prednisone Intensol (Prednisone), Proleukin (Aldesleukin), Purinethol (Mercaptopurine), Reclast (Zoledronic acid), Revlimid (Lenalidomide), Rheumatrex (Methotrexate), Rituxan (Rituximab), RoferonA alfaa (Interferon alfa-2a), Rubex (Doxorubicin), Sandostatin (Octreotide), Sandostatin LAR Depot (Octreotide), Soltamox (Tamoxifen), Sprycel (Dasatinib), Sterapred (Prednisone), Sterapred DS (Prednisone), Stivarga (Regorafenib), Supprelin LA (Histrelin Implant), Sutent (Sunitinib), Sylatron (Peginterferon Alfa-2b Injection (Sylatron)), Synribo (Omacetaxine Injection), Tabloid (Thioguanine), Taflinar (Dabrafenib), Tarceva (Erlotinib), Targretin Capsules (Bexarotene), Tasigna (Decarbazine), Taxol (Paclitaxel Injection), Taxotere (Docetaxel), Temodar (Temozolomide), Temodar (Temozolomide Injection), Tepadina (Thiotepa), Thalomid (Thalidomide), TheraCys BCG (BCG), Thioplex (Thiotepa), TICE BCG (BCG), Toposar (Etoposide Injection), Torisel (Temsirolimus), Treanda (Bendamustine hydrochloride), Trelstar (Triptorelin Injection), Trexall (Methotrexate), Trisenox (Arsenic trioxide), Tykerb (lapatinib), Valstar (Valrubicin Intravesical), Vantas (Histrelin Implant), Vectibix (Panitumumab), Velban (Vinblastine), Velcade (Bortezomib), Vepesid (Etoposide), Vepesid (Etoposide Injection), Vesanoid (Tretinoin), Vidaza (Azacitidine), Vincasar PFS (Vincristine), Vincrex (Vincristine), Votrient (Pazopanib), Vumon (Teniposide), Wellcovorin IV (Leucovorin Injection), Xalkori (Crizotinib), Xeloda (Capecitabine), Xtandi (Enzalutamide), Yervoy (Ipilimumab Injection), Zaltrap (Ziv-aflibercept Injection), Zanosar (Streptozocin), Zelboraf (Vemurafenib), Zevalin (Ibritumomab Tiuxetan), Zoladex (Goserelin), Zolinza (Vorinostat), Zometa (Zoledronic acid), Zortress (Everolimus), Zytiga (Abiraterone), Nimotuzumab and immune checkpoint inhibitors such as nivolumab, pembrolizumab/MK-3475, pidilizumab and AMP-224 targeting PD-1; and BMS-935559, MEDI4736, MPDL3280A and MSB0010718C targeting PD-L1 and those targeting CTLA-4 such as ipilimumab.

Radiotherapy means the use of radiation, usually X-rays, to treat illness. X-rays were discovered in 1895 and since then radiation has been used in medicine for diagnosis and investigation (X-rays) and treatment (radiotherapy). Radiotherapy may be from outside the body as external radiotherapy, using X-rays, cobalt irradiation, electrons, and more rarely other particles such as protons. It may also be from within the body as internal radiotherapy, which uses radioactive metals or liquids (isotopes) to treat cancer.

Simultaneous administration typically means that both compounds enter the patient at precisely the same time. However, simultaneous administration also includes the possibility that the NEN and retinoic acid enter the patient at different times, but the difference in time is sufficiently miniscule that the first administered compound is not provided the time to take effect on the patient before entry of the second administered compound. Such delayed times typically correspond to less than 1 minute, and more typically, less than 30 seconds. In one example, wherein the compounds are in solution, simultaneous administration can be achieved by administering a solution containing the combination of compounds. In another example, simultaneous administration of separate solutions, one of which contains the NEN and the other of which contains retinoic acid, can be employed. In one example wherein the compounds are in solid form, simultaneous administration can be achieved by administering a composition containing the combination of compounds. Alternatively, simultaneous administration can be achieved by administering two separate compositions, one comprising the NEN and the other comprising retinoic acid.

In other embodiments, the NEN and retinoic acid are not administered simultaneously. In some embodiments, the NEN is administered before retinoic acid. In other embodiments, retinoic acid is administered before the NEN. In other embodiments, the first administered compound is provided time to take effect on the patient before the second administered compound is administered. Generally, the difference in time does not extend beyond the time for the first administered compound to complete its effect in the patient, or beyond the time the first administered compound is completely or substantially eliminated or deactivated in the patient.

In some embodiments, the retinoic acid is administered in a therapeutically effective amount or dosage. A "therapeutically effective amount" is an amount of retinoic acid that, when administered to a patient by itself, effectively treats neuroblastoma. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the compound that corresponds to a therapeutically effective amount is strongly dependent on the type of cancer, stage of the cancer, the age of the patient being treated, and other facts. In general, therapeutically effective amounts, e.g., retinoic acid, are known in the art.

In other embodiments, the retinoic acid is administered in a sub-therapeutically effective amount or dosage. A sub-therapeutically effective amount is an amount of that, when administered to a patient by itself, does not completely inhibit over time the biological activity of the intended target.

Whether administered in therapeutic or sub-therapeutic amounts, the combination of the NEN and retinoic acid should be effective in treating cancer, e.g. neuroblastoma. For example, a subtherapeutic amount of retinoic acid can be an effective amount if, when combined with an NEN, the combination is effective in the treatment of neuroblastoma.

In some embodiments, the combination of compounds exhibits a synergistic effect (i.e., greater than additive effect) in the treatment of neuroblastoma. The term "synergistic effect" refers to the action of two agents, such as, for example, an NEN and retinoic acid, producing an effect, for example, slowing the symptomatic progression of cancer, e.g. neuroblastoma, or symptoms thereof, which is greater than the simple addition of the effects of each drug administered alone.

Different dosage regimens can be used to treat cancer, e.g. neuroblastoma. In some embodiments, a daily dosage, such as any of the exemplary dosages described above, is administered once, twice, three times, or four times a day for three, four, five, six, seven, eight, nine, or ten days. Depending on the stage and severity of the cancer, a shorter treatment time (e.g., up to five days) can be employed along with a high dosage, or a longer treatment time (e.g., ten or more days, or weeks, or a month, or longer) can be employed along with a low dosage. In some embodiments, a once- or twice-daily dosage is administered every other day. In some embodiments, each dosage contains both an NEN and retinoic acid to be delivered as a single dosage, while in other embodiments each dosage contains an NEN or retinoic acid to be delivered as separate dosages.

The agents can be administered via any of the accepted modes of administration or agents known in the art. The compounds can be administered, for example, orally, nasally, parenterally (intravenous, intramuscular, or subcutaneous), topically, transdermally, intravaginally, intravesically, intracisternally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, preferably in unit dosage forms suitable for simple administration of precise dosages. A particular route of administration is oral, particularly one in which a convenient daily dosage regimen can be adjusted according to the degree of severity of the disease to be treated.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

Methods of Use

Methods are provided for treating or reducing primary or metastatic cancer, including without limitation juvenile chronic myelogenous leukemia (CML), neuroblastoma, including high risk neuroblastoma, recurrent cervical cancer, squamous cell head and neck cancer, and squamous cell skin carcinoma. In some embodiments the cancer is neuroblastoma. In some embodiments the neuroblastoma is high risk neuroblastoma. The cancer is treated in a regimen comprising contacting the targeted cells with a combination of (i) retinoic acid, e.g. isotretinoin; and (ii) NEN. Such methods include administering to a subject in need of treatment a therapeutically effective amount or an effective dose of the combined agents of the invention.

Effective doses of the combined agents of the present invention for the treatment of cancer vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage of each agent may range from about 0.0001 to 5000 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration daily, every other day, every third day, weekly, etc. Intervals can also be irregular as indicated by measuring blood levels of the therapeutic entity in the patient. Alternatively, therapeutic entities of the present invention can be administered as a sustained release formulation, in which case less frequent administration is required.

Chemotherapeutic agents that can be administered in combination with NEN treatment include, without limitation, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon.

Targeted therapeutics that can be administered in combination with NEN may include, without limitation, tyrosine-kinase inhibitors, such as Imatinib mesylate (Gleevec, also known as STI-571), Gefitinib (Iressa, also known as ZD1839), Erlotinib (marketed as Tarceva), Sorafenib (Nexavar), Sunitinib (Sutent), Dasatinib (Sprycel), Lapatinib (Tykerb), Nilotinib (Tasigna), and Bortezomib (Velcade); Janus kinase inhibitors, such as tofacitinib; ALK inhibitors, such as crizotinib; Bcl-2 inhibitors, such as obatoclax, venclexta, and gossypol; FLT3 inhibitors, such as midostaurin (Rydapt), IDH inhibitors, such as AG-221, PARP inhibitors, such as Iniparib and Olaparib; PI3K inhibitors, such as perifosine; VEGF Receptor 2 inhibitors, such as Apatinib; AN-152 (AEZS-108) doxorubicin linked to [D-Lys(6)]-LHRH; Braf inhibitors, such as vemurafenib, dabrafenib, and LGX818; MEK inhibitors, such as trametinib; CDK inhibitors, such as PD-0332991 and LEE011; Hsp90 inhibitors, such as salinomycin; and/or small molecule drug conjugates, such as Vintafolide; serine/threonine kinase inhibitors, such as Temsirolimus (Torisel), Everolimus (Afinitor), Vemurafenib (Zelboraf), Trametinib (Mekinist), and Dabrafenib (Tafinlar).

A combination NEN may be administered in combination with an immunomodulator, such as a cytokine, a lymphokine, a monokine, a stem cell growth factor, a lymphotoxin (LT), a hematopoietic factor, a colony stimulating factor (CSF), an interferon (IFN), parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, a transforming growth factor (TGF), such as TGF-α or TGF-β, insulin-like growth factor (IGF), erythropoietin, thrombopoietin, a tumor necrosis factor (TNF) such as TNF-α or TNF-β, a mullerian-inhibiting substance, mouse gonadotropin-associated peptide, inhibin, activin, vascular endothelial growth factor, integrin, granulocyte-colony stimulating factor (G-CSF), granulocyte macrophage-colony stimulating factor (GM-CSF), an interferon such as interferon-α, interferon-β, or interferon-γ, S1 factor, an interleukin (IL) such as IL-1, IL-1cc, IL-2, IL-3, IL-4, IL-5, IL-6, IL-7, IL-8, IL-9, IL-10, IL-11, IL-12, IL-13, IL-14, IL-15, IL-16, IL-17, IL-18 IL-21 or IL-25, LIF, kit-ligand, FLT-3, angiostatin, thrombospondin, endostatin, and LT. Tumor specific monoclonal antibodies may also be administered in combination with NEN.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Compositions can be administered by parenteral, topical, intravenous, intratumoral, oral, subcutaneous, intraarterial, intracranial, intraperitoneal, intranasal or intramuscular means. A typical route of administration is oral, although other routes can be equally effective.

Typically, compositions are prepared as tablets, gel capsules, liquid solutions, suspensions, etc.; solid forms suitable for solution in, or suspension in, liquid vehicles prior to injection can also be prepared. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the combined agents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the active agents and formulations thereof, of the invention and instructions for use. The kit can further contain a least one additional reagent, e.g. a chemotherapeutic drug, ESA, etc. Kits typically include a label indicating the intended use of the contents of the kit. The term label includes any writing, or recorded material supplied on or with the kit, or which otherwise accompanies the kit.

The compositions can be administered for therapeutic treatment. Compositions are administered to a patient in an amount sufficient to substantially ablate targeted cells, as described above. An amount adequate to accomplish this is defined as a "therapeutically effective dose.", which may provide for an improvement in overall survival rates. Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Reprogramming the Neuroblastoma Epigenome with a Mitochondrial Uncoupler

Growing evidence points to the critical role of dysregulated epigenetics in promoting cancer progression. In general, the cancer epigenome displays global hypomethylation and CpG island hypermethylation. Particularly, CpG islands hypermethylation in promoter region leads to the silencing of tumor suppressors, cell differentiation markers associated with poor prognosis in cancer patients, and therapeutic resistance.

Unlike genetic mutations, epigenetic changes are reversible. Thus, CpG island hypermethylation has become an attractive target for cancer therapy. The DNA methyltransferase inhibitors (DNMTi) azacitidine and decitabine have shown promising effect in clinical trials and have been approved by the FDA and EMA to treat hematopoietic malignancies.

DNA demethylation in mammals is achieved through TET enzyme-mediated sequential oxidation of 5-methylcytosine (5-mC) to 5-hydroxymethylcytosine (5-hmC), 5-formylcytosine (5-fC) and then 5-carboxylcytosine (5-caC), followed by thymine DNA glycosylase (TDG)-mediated excision of 5-fC and 5-caC coupled with base excision repair. This multi-step DNA demethylation process requires the co-substrate α-ketoglutarate (α-KG), a tricarboxylic acid (TCA) cycle intermediate that can be generated from glucose or glutamine. However, under hypoxia, α-KG is reduced and converted to 2-hydroxyglutarate (2-HG) as an oncometabolite due to a reduced $NAD^+/NADH$ ratio, thus inhibiting TET. Based on these discoveries, we hypothesized that DNA hypermethylation would be reversed by increasing the intracellular $NAD^+/NADH$ ratio, thus, restoring the redox homoeostasis. Consequently, the aberrant metabolic and epigenetic phenotypes of cancer cells would be corrected.

The electron transport chain (ETC) is the major site for cells to regenerate $NAD^+$ from NADH. Mitochondrial uncouplers facilitate proton influx across the mitochondrial inner membrane without generating ATP, leading to activation of the electron transport chain (ETC). We hypothesized that ETC activation by mitochondrial uncoupler would increases the $NAD^+/NADH$ ratio, leading to an increase of the αKG/2HG ratio. In this study, we used one mitochondrial uncoupler, niclosamide ethanolamine (NEN), to reprogram the metabolism and epigenetic landscape of cancer cells. We found that NEN treatment increases the intracellular NAD$^+$/NADH ratio and αKG/2HG ratio. This metabolic reprogramming reduces DNA methylation in promoter region and activates neuroblastoma differentiation program. N-Myc, an oncogenic transcription factor often amplified in neuroblastoma (NB) and is associated with worse patient survival, is downregulated by NEN treatment. Importantly, NEN treatment reduces 2HG production, HIF levels and HIF transcriptional targets expression under hypoxia. Furthermore, NEN treatment inhibits reductive carboxylation, a key metabolic pathway that converts α-KG to citrate to support cancer cell growth upon ETC inhibition. Together, these results uncover a new role of mitochondrial uncoupling as an epigenetic intervention that promotes DNA demethylation and inhibit neuroblastoma growth.

Mitochondrial uncoupling increased intracellular α-KG and α-KG/2-HG ratio. Mitochondrial uncoupling is a process that dissipates the proton gradient across the inner mitochondrial membrane, activating the ETC to promote NADH oxidation. Niclosamide ethanolamine (NEN) is a salt form of the FDA-approved mitochondrial uncoupler drug niclosamide with an excellent safety profile. As expected, NEN treatment increased ADP/ATP and AMP/ATP ratios (FIG. 10a, b). Importantly, NEN treatment increased intracellular NAD$^+$/NADH ratio in both SK-N-BE(2) and NB16 cells (FIG. 1a, b). In addition, the pyruvate/lactate ratio, determined by the NAD$^+$/NADH ratio, was also increased upon NEN treatment, indicating inhibition of the Warburg effect (FIG. 1a, b). Furthermore, NEN treatment did not cause oxidative stress in our experimental setting, based on the observation that NEN did not reduce the glutathione (GSH)/glutathione disulfide (GSSG) ratio in SK-N-BE(2) or NB16 cells (FIG. 10a, b).

Figure 10:
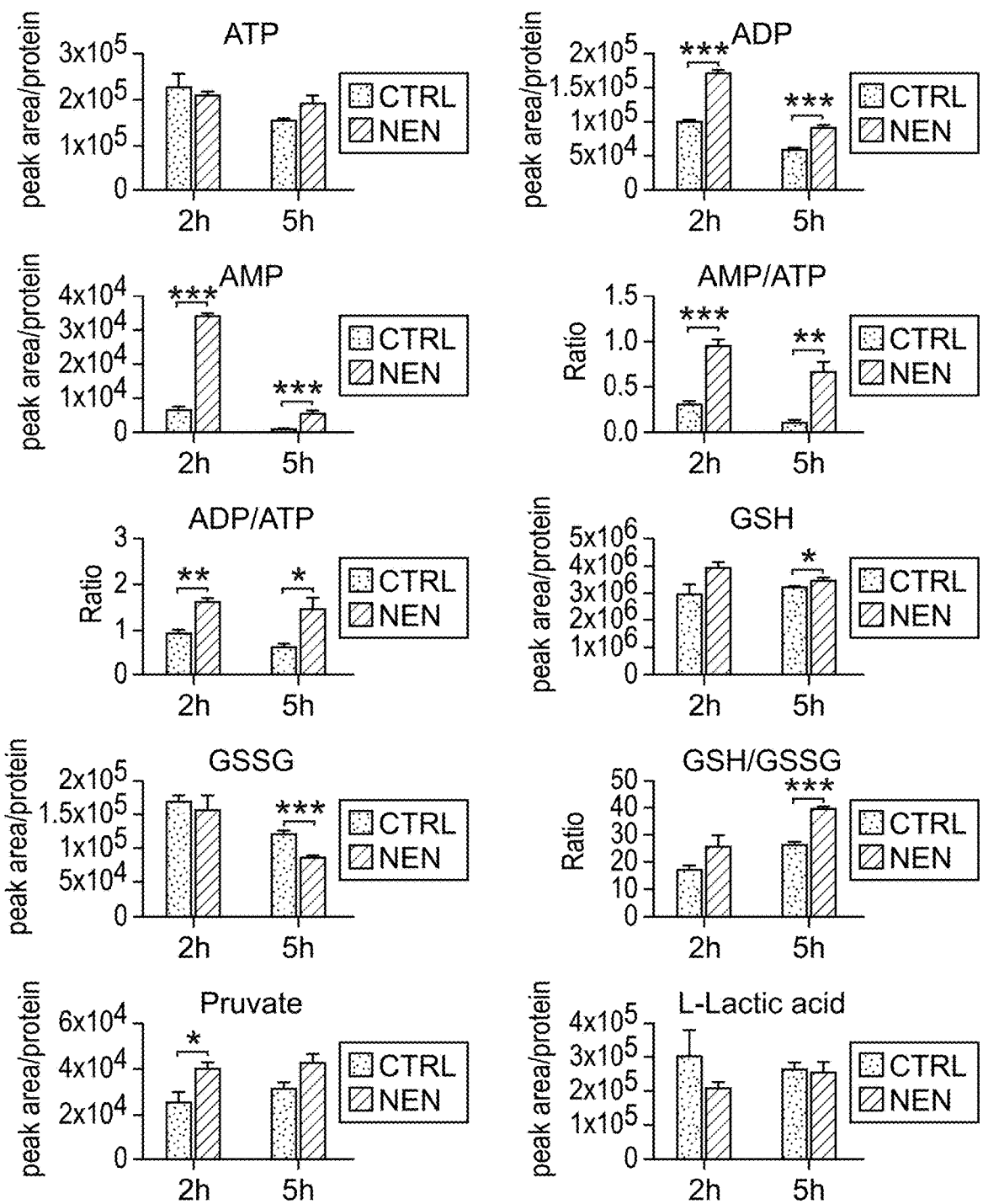
FIG. 10a-FIG. 10b. The metabolic profiling upon NEN treatment. Relative intracellular metabolite levels of the same samples in FIGS. 1a and b. Data represent mean±SEM (n=3, biologically repeats). Representative of at least two independent experiments. *P<0.05, P<0.01, *P<0.001. Two-sided Student's t-test.
Figure 10:
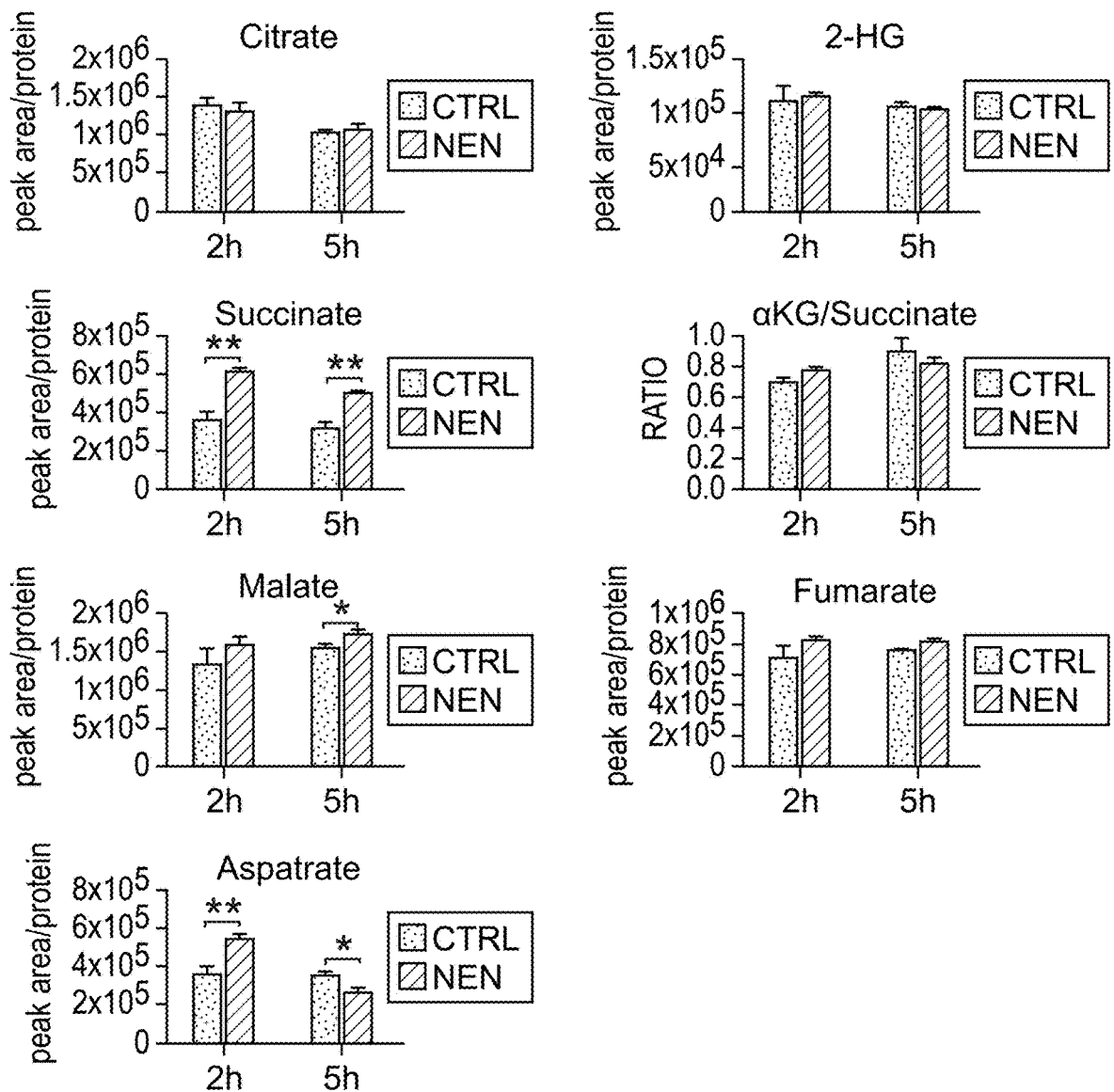
Figure 10:
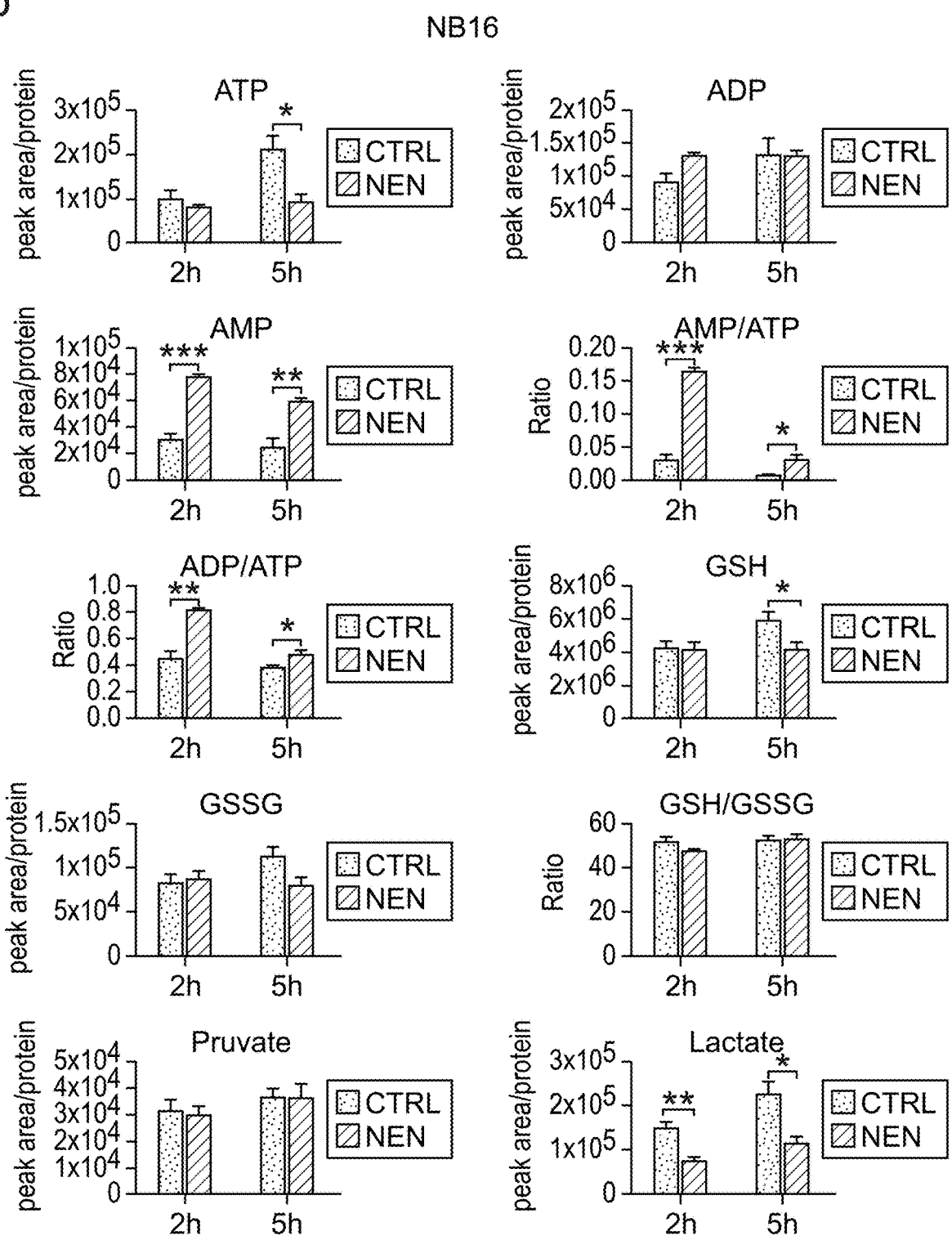
Figure 10:
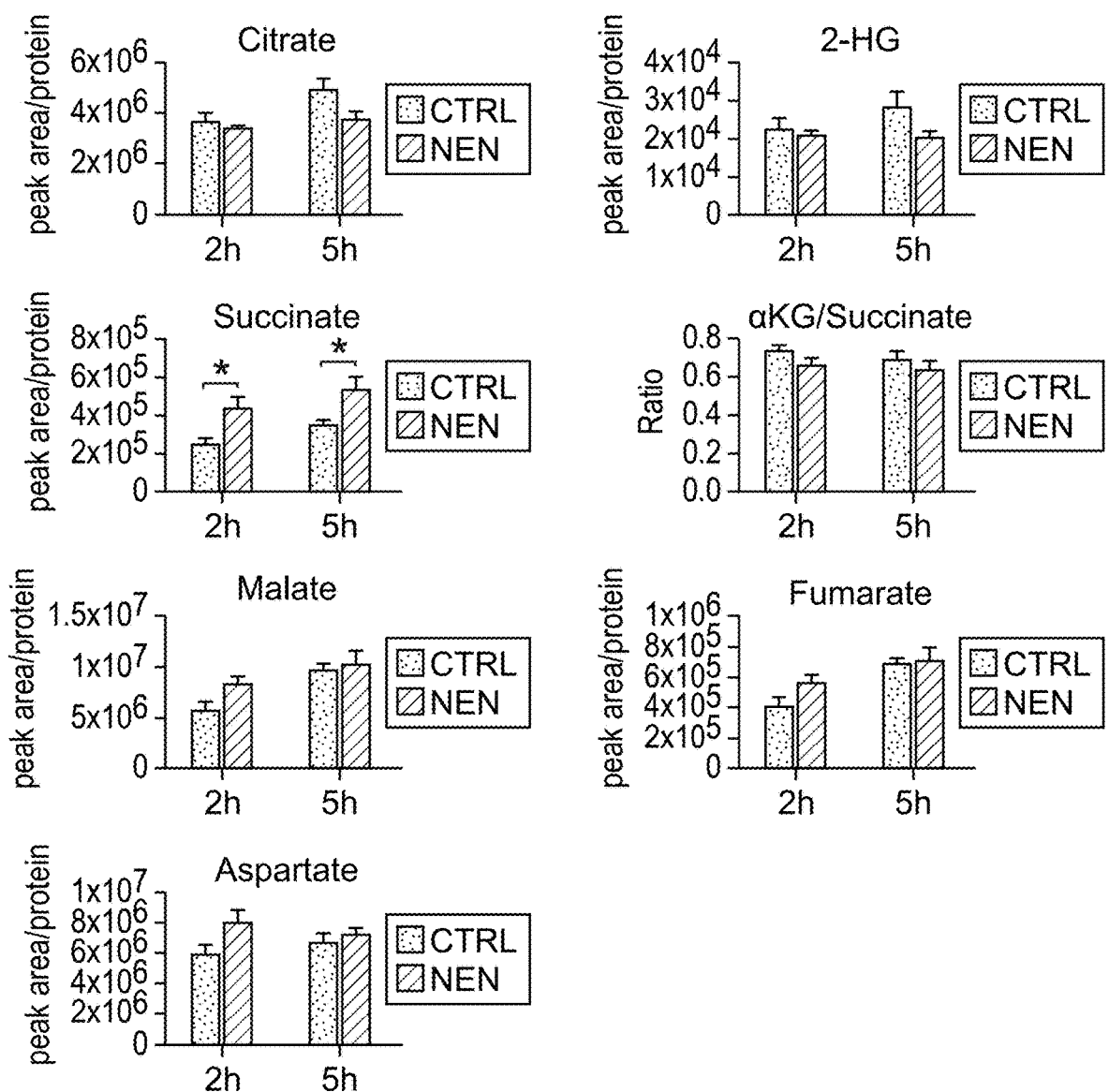

Because multiple key reactions in TCA cycle use NAD$^+$ as an electron acceptor, a high NAD$^+$/NADH ratio is the major driving force for TCA cycle (FIG. 1c). We next examined how mitochondrial uncoupling regulates TCA cycle metabolite levels. As the product of the first step of TCA cycle, citrate was not affected by NEN treatment (FIG. 10). Surprisingly, intracellular α-KG levels increased significantly in both cell lines after NEN treatment (FIG. 1a, b). Succinate also accumulated under NEN treatment while the αKG/succinate ratio stayed unchanged (FIG. 10a, b), and no significant increase of either fumarate or malate was observed after NEN treatment (FIG. 10a, b). Aspartate, which is derived from oxaloacetate, also accumulated after NEN treatment (FIG. 10a, b). Because glutamine and glutamate provide the carbon backbone to generate α-KG, we wondered whether the increased α-KG originated from glutamine. NEN treatment significantly reduced the intracellular glutamine and glutamate levels, suggesting the acceleration of glutaminolysis by mitochondrial uncoupling (FIG. 1d).

To determine how mitochondrial uncoupling alters the glutamine flux into TCA cycle, we carried out [U-$^{13}$C$_5$]-glutamine tracing assay (FIG. 1c). Surprisingly, in SK-N-BE(2) cells, no significant increase of m+5 α-KG was observed. However, the labelling percentage of m+3 (2$^{nd}$ cycle) and m+½ (3$^{rd}$ cycle) α-KG significantly increased upon NEN treatment (FIG. 1d,e). Also, the labelling abundance of m+2(2$^{nd}$ cycle) and m+½ (3$^{rd}$ cycle) succinate and aspartate (from oxaloacetate) significantly increased under NEN treatment (FIG. 11a), suggesting that NEN treatment accelerates the of TCA cycle flux in the oxidative direction.

Figure 11:
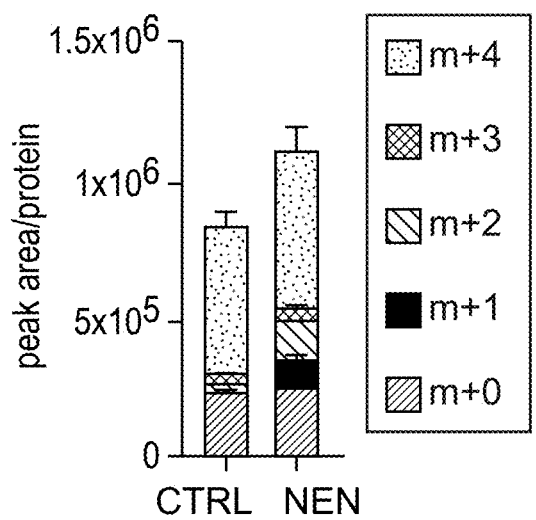
Figure 11:
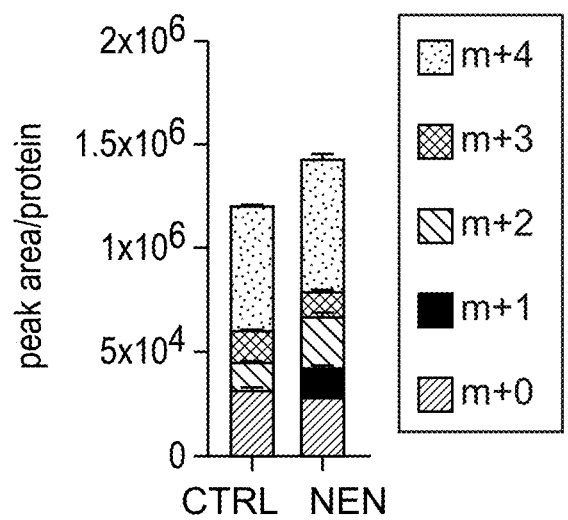
Figure 11:
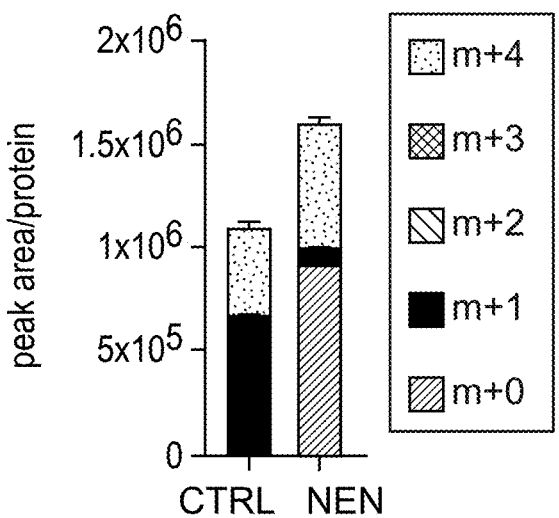
Figure 11:
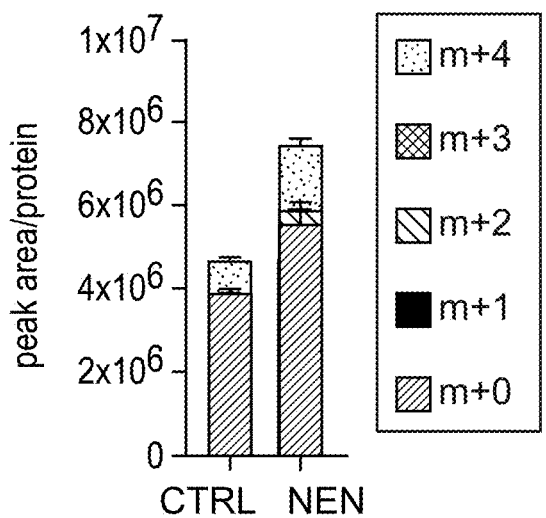
Figure 12:
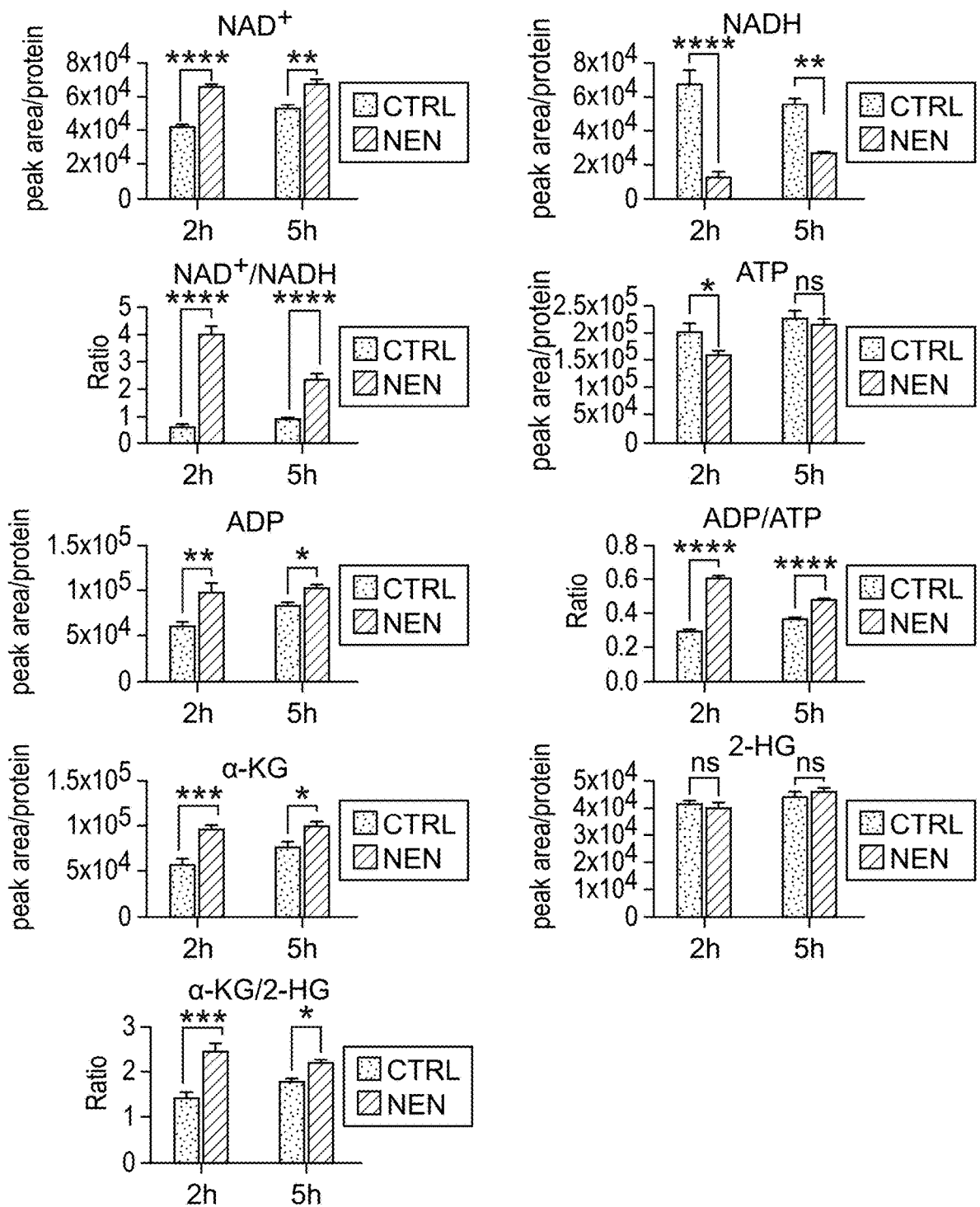
FIG. 12a-FIG. 12c. The metabolic reprograming effect of NEN on other cancer cell types. Relative intracellular metabolite level or ratios were measured using LC/MS in (FIG. 12a) Ovcar3 cells, (FIG. 12b) H29 and (FIG. 12c) H82 cells. Cells were treated with DMSO or 1 μM NEN for 2 h or 5 h. Data represent mean±SEM (n=3, biologically repeats). Representative of at least two independent experiments. *P<0.05 P<0.01 and *P<0.001. Two-sided Student's t-test.
Figure 12:
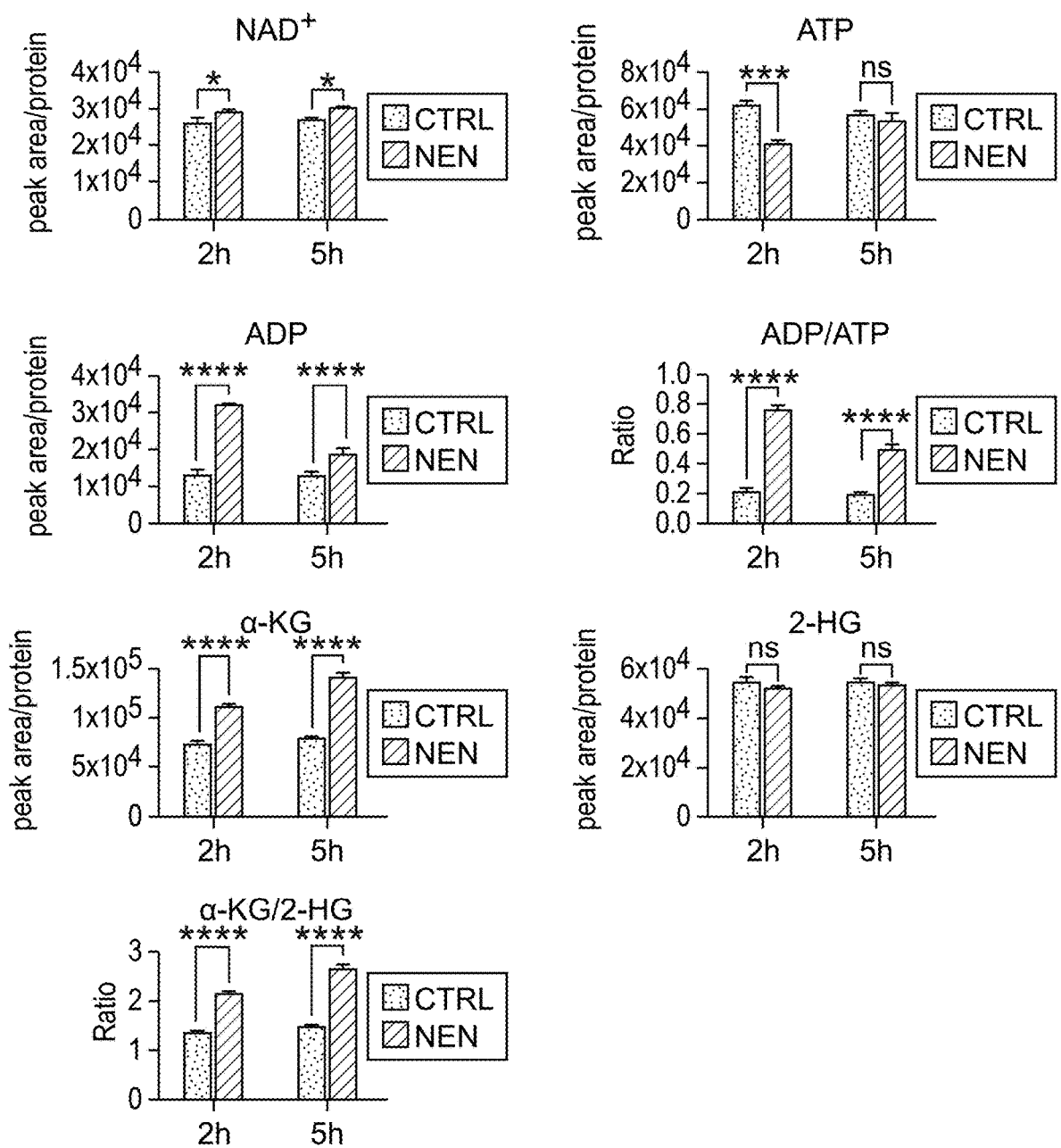
Figure 12:
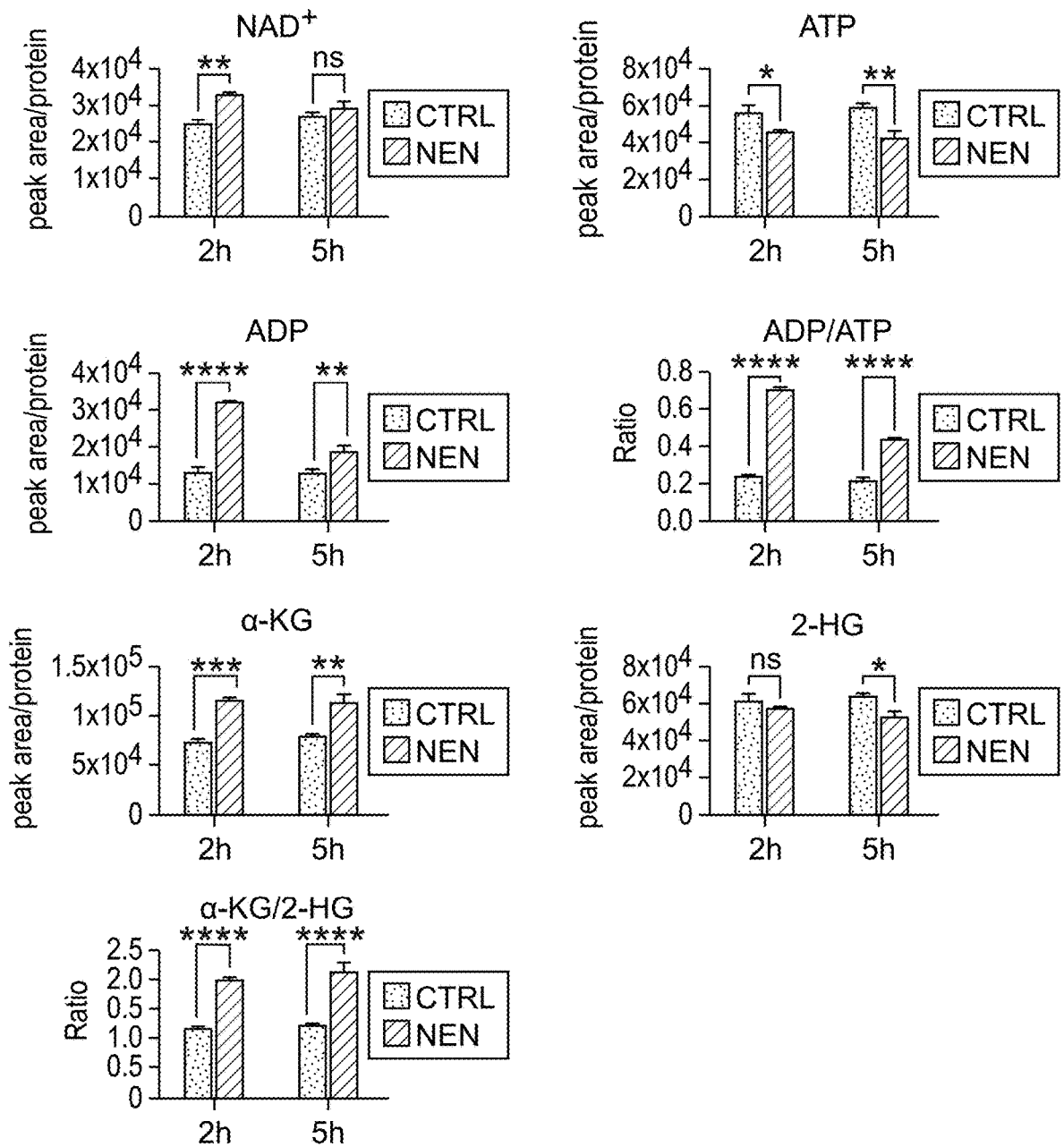

Importantly, the m+5 labelling abundance of 2-HG was significantly decreased by NEN treatment in SK-N-BE(2) cells (FIG. 1e). The ratio of m+5 α-KG/m+5 2-HG decreased under NEN treatment (FIG. 1e), indicating that NEN inhibits the conversion of α-KG to 2-HG. In NB16 cells, no significant reduction of m+5 2-HG was observed, possibly due to the lower 2-HG generation in this cell line (FIG. 1e). The increased m+5 and m+3 labeling from glutamine accounted for the α-KG increase (FIG. 1e), and was associated with increased m+4 succinate and m+4 aspartate (FIG. 11b). We also tested the metabolic reprograming effect of NEN on other cancer cell lines, including an ovarian cancer cell line OVCAR3, and two lung cancer cell lines H29 and H82. All the cell lines showed similar metabolic reprograming effects, featured by the increased ADP/ATP ratio and α-KG/2-HG ratio, indicating that this is a universal metabolic reprogramming effect shared by multiple cancer types (FIG. 12). Together, these data suggest that NEN treatment upregulates cellular α-KG through two potential mechanisms: accelerating glutaminolysis and blocking the conversion of α-KG to 2-HG.

Figure 2:
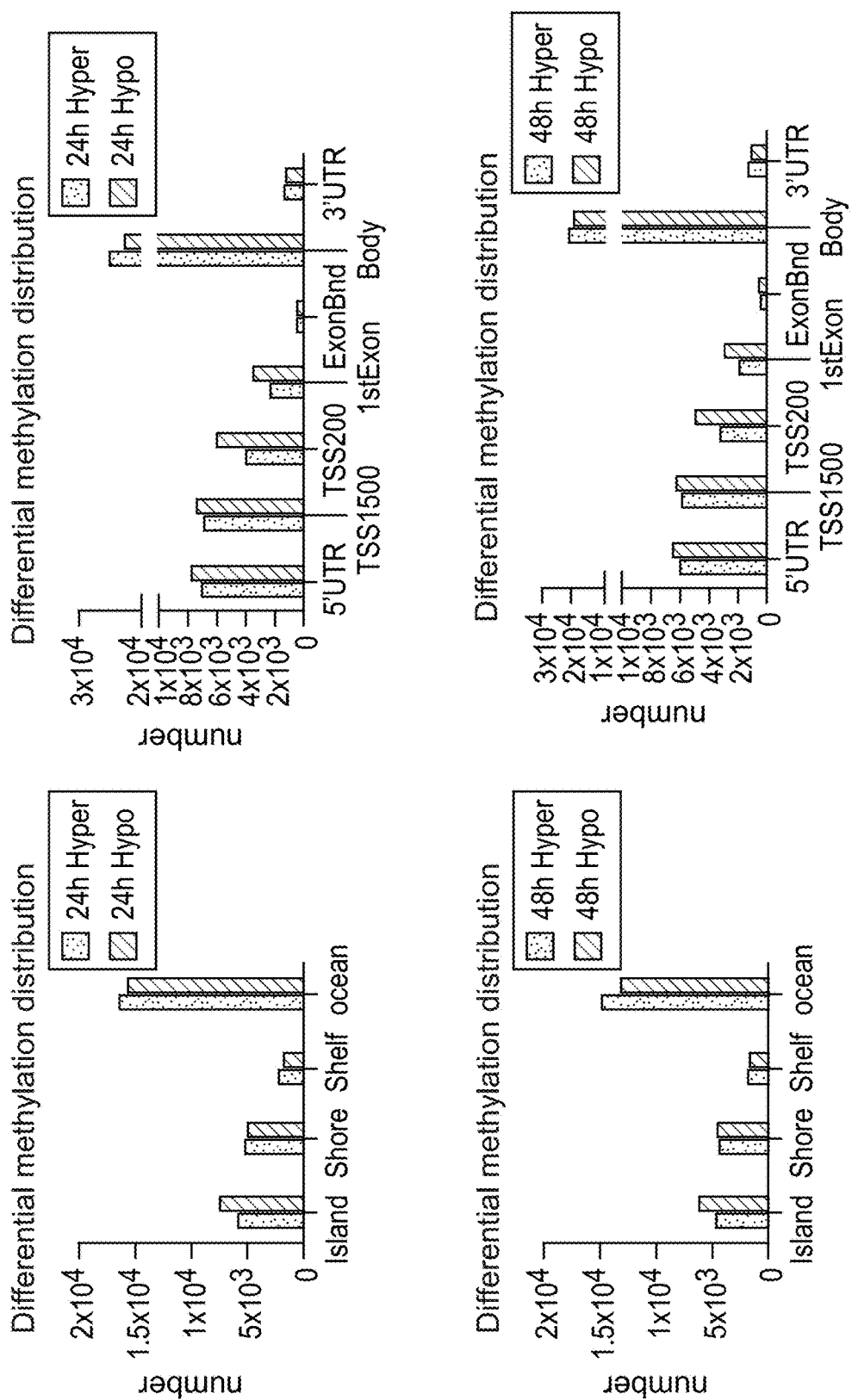
FIG. 2a-FIG. 2c. Mitochondrial uncoupling remodels the epigenetic landscape in neuroblastoma cells.
Figure 2:
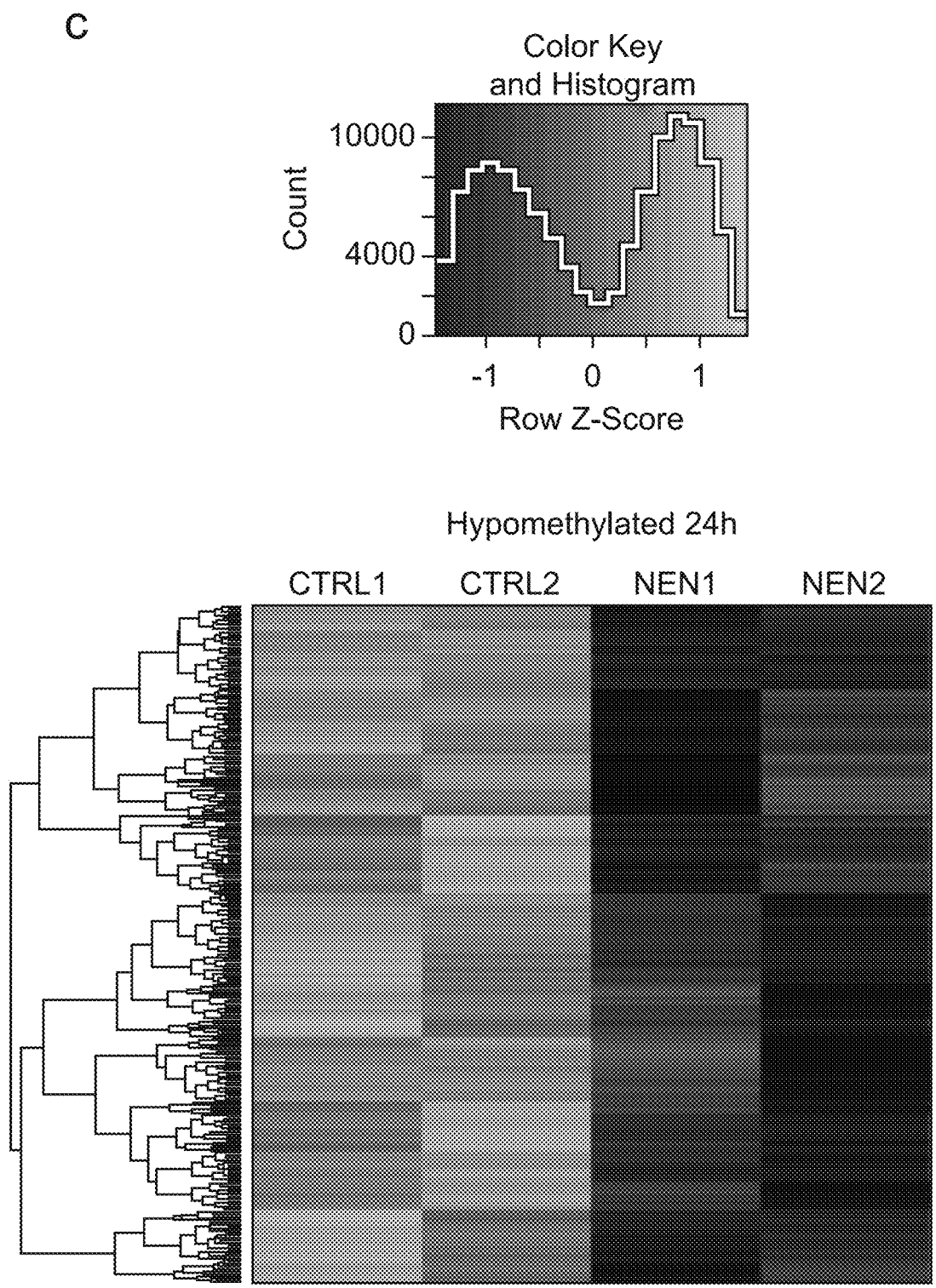
Figure 2:
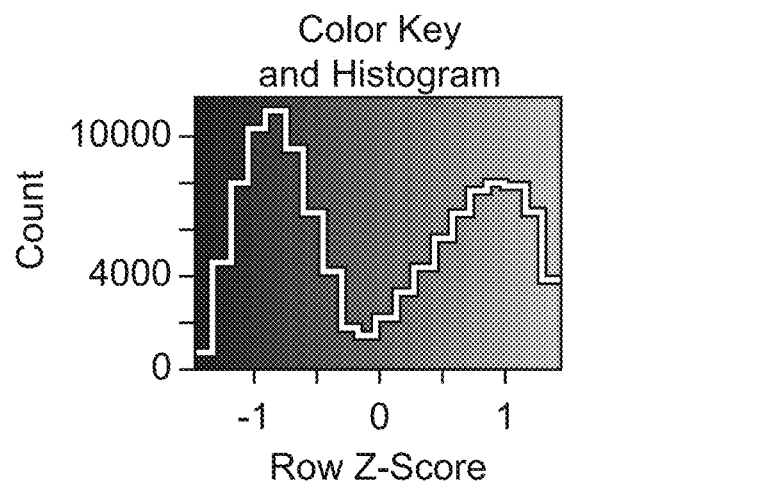
Figure 2:
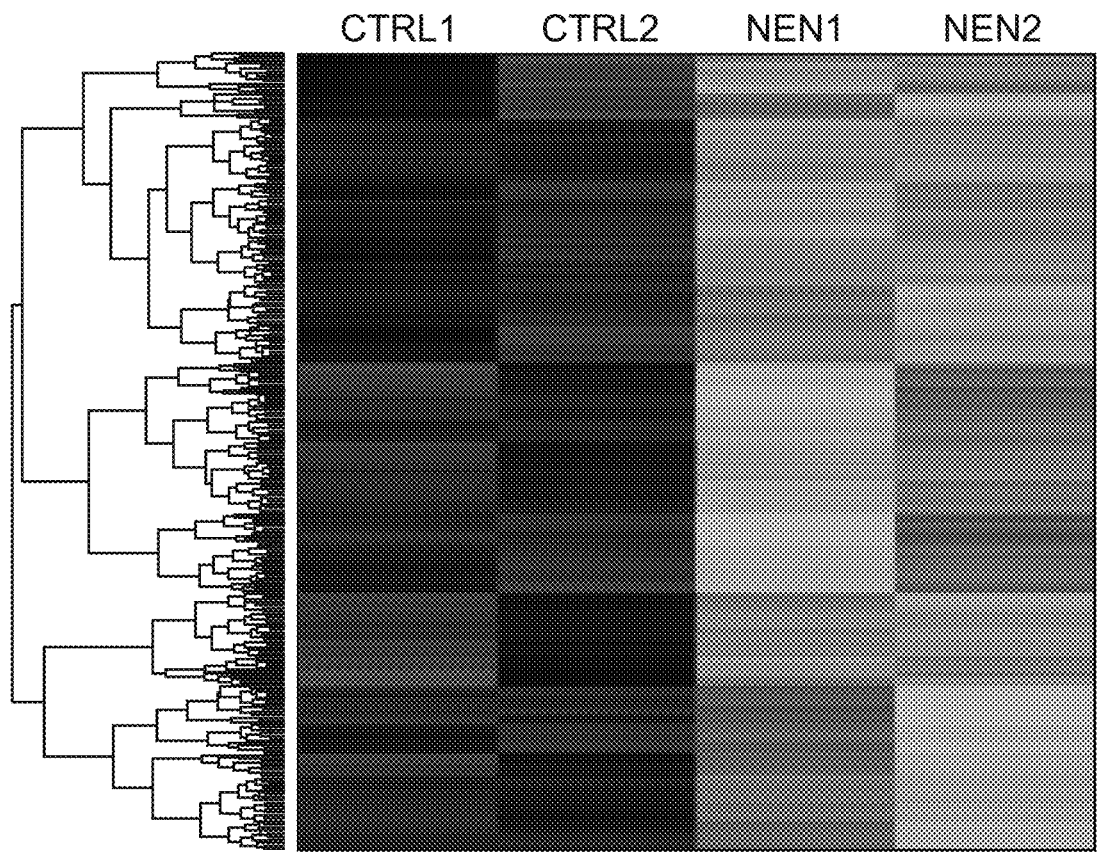

Mitochondrial uncoupling remodels the epigenetic landscape in neuroblastoma cells. The epigenetic landscape is tightly connected with metabolic state. Thus, we wonder whether NEN treatment alters the global or locus-specific DNA methylation. To capture the dynamic changes of global DNA methylation, we used LC-MS based analysis to quantify the ratio of 5-methyl-deoxycytidine (5mdc) to deoxycytidine (dc) in cells treated with NEN or a DNMT inhibitor 5-Azacytidine (5-Aza) at various time points. Intriguingly, while 5-Aza reduced global methylation, NEN treatment slightly increased global DNA methylation (FIG. 2a). Next, illumina Infinium® Methylation EPIC array was used to study the locus-specific DNA methylation pattern. Genomic annotation of differentially methylated sites upon NEN treatment were categorized according to their genomic location. We found that NEN treatment generates more hypomethylated sites than hyper-methylated sites in CpG islands, while in 'shelf' and 'shore' regions, it shows the opposite trend (FIG. 2b). In addition, NEN treatment generates more hypomethylated sites than hypermethylated sites in regions close to transcription start sites (TSS) especially within TSS200 and 1$^{st}$ exon (FIG. 2b). In contrast, NEN treatment generates more hypermethylated sites than hypomethylated sites in the gene body and 3' UTR region (FIG. 2b). The hypomethylated and hypermethylated sites are presented as a heatmap (FIG. 2c).

Figure 3:
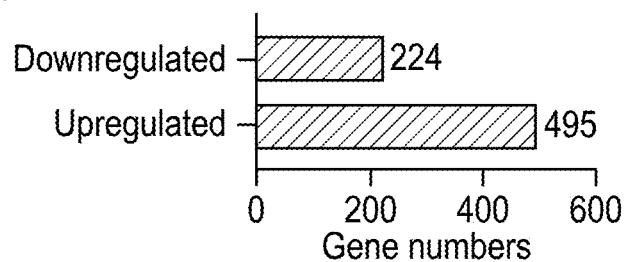
FIG. 3a-FIG. 3j. NEN promote neuroblastoma differentiation.
Figure 3:
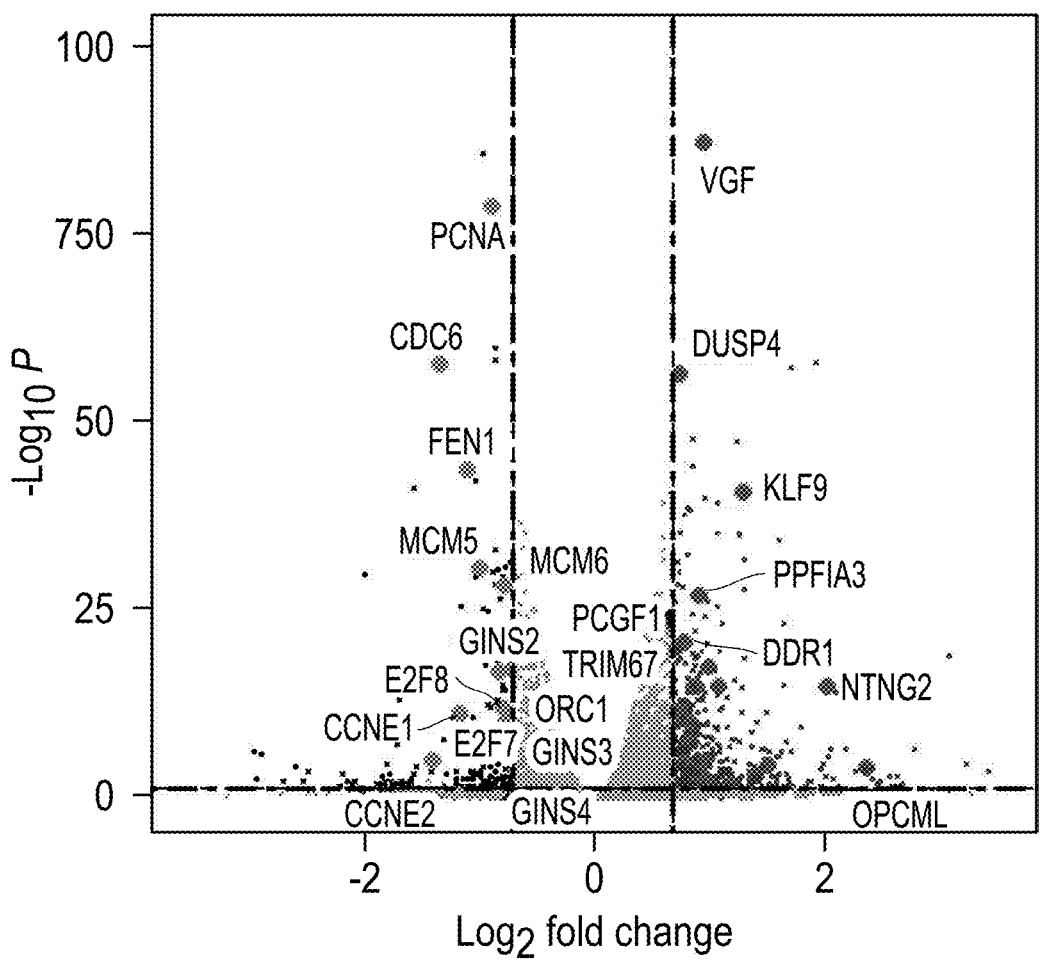
Figure 3:
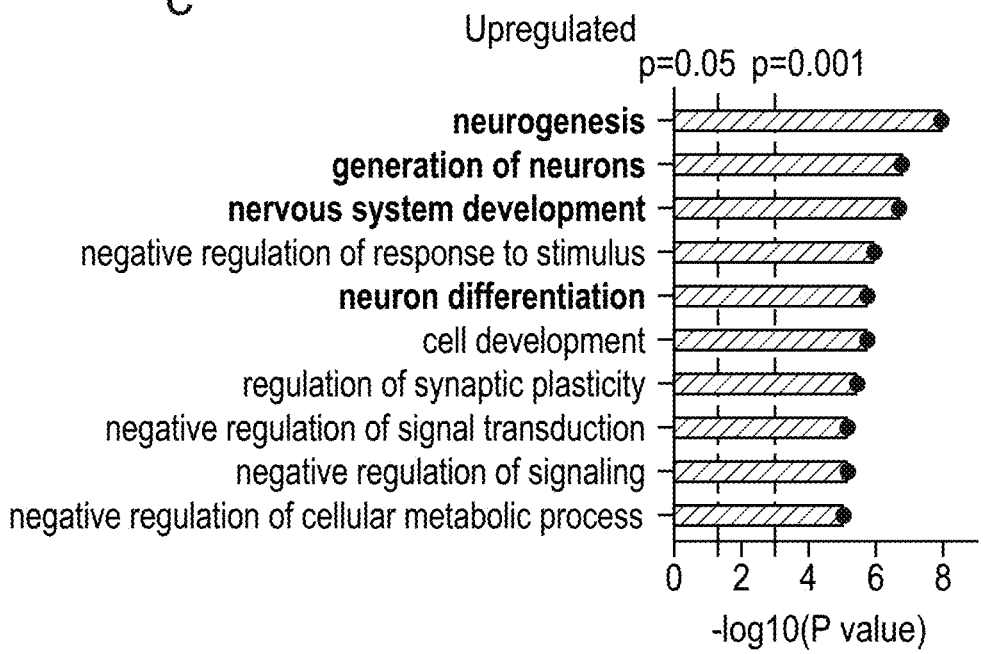
Figure 3:
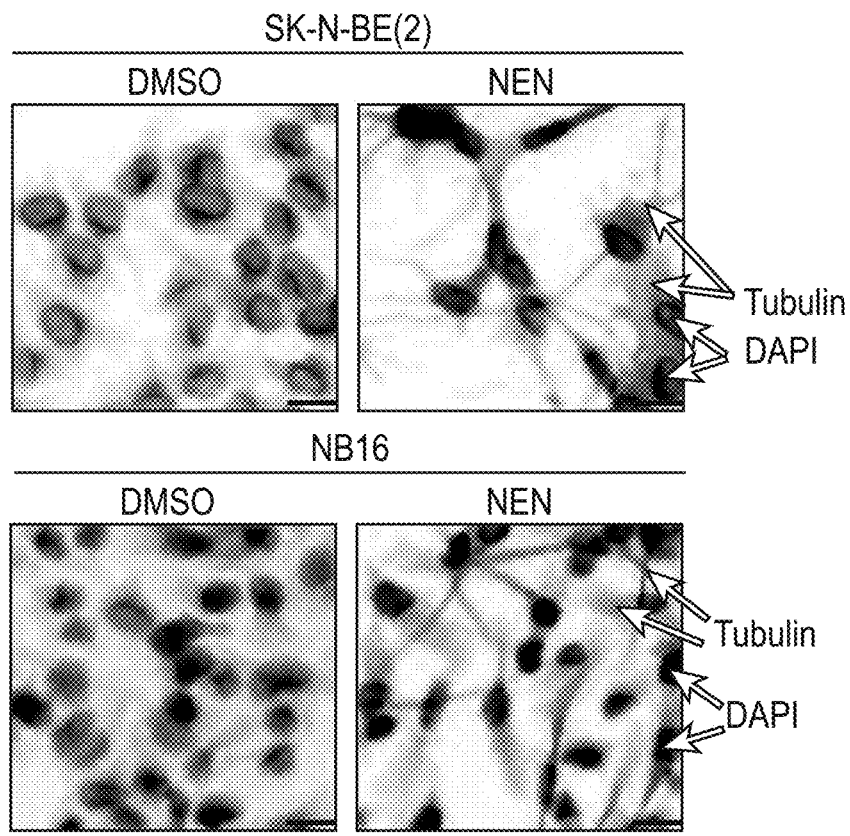
Figure 3:
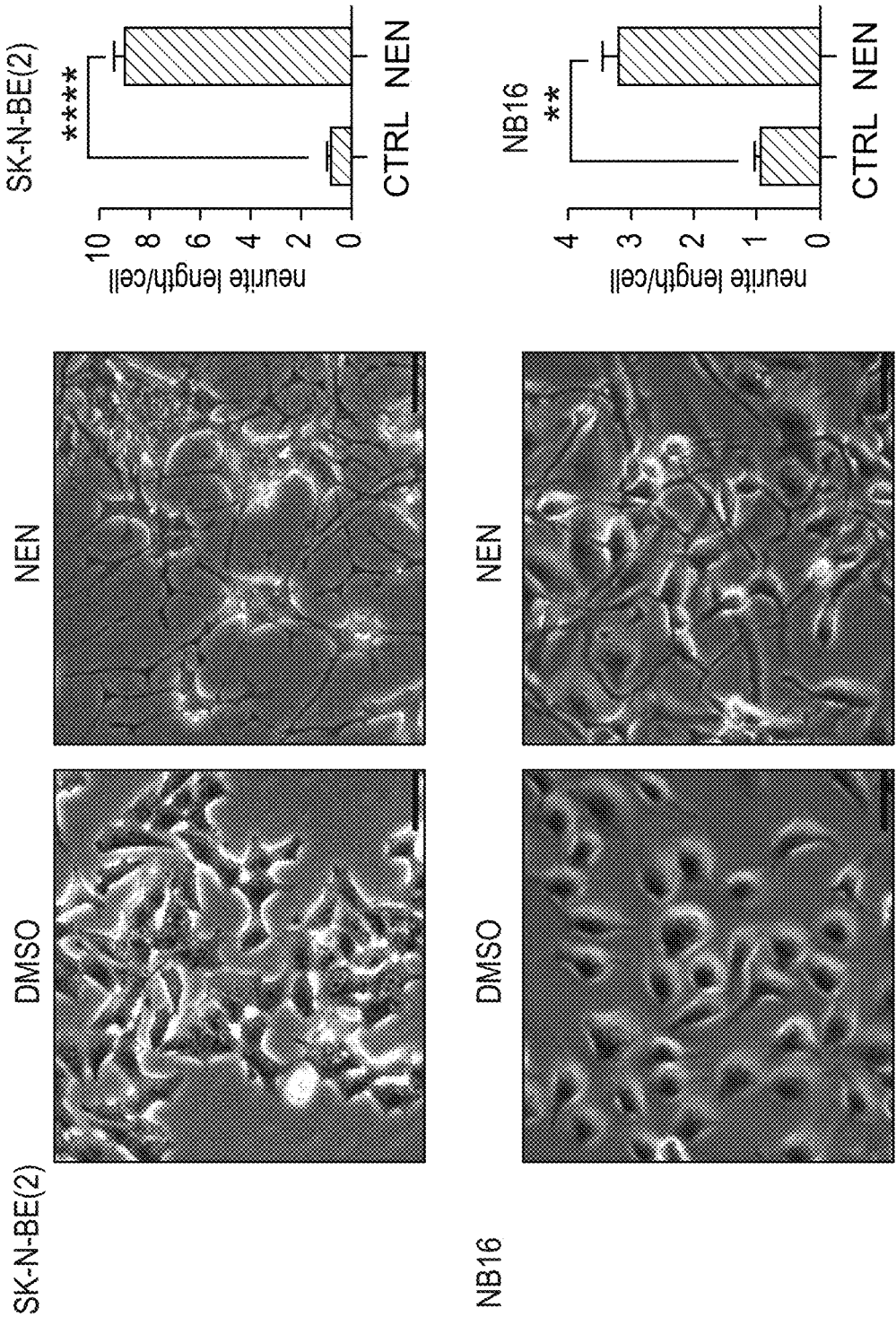
Figure 3:
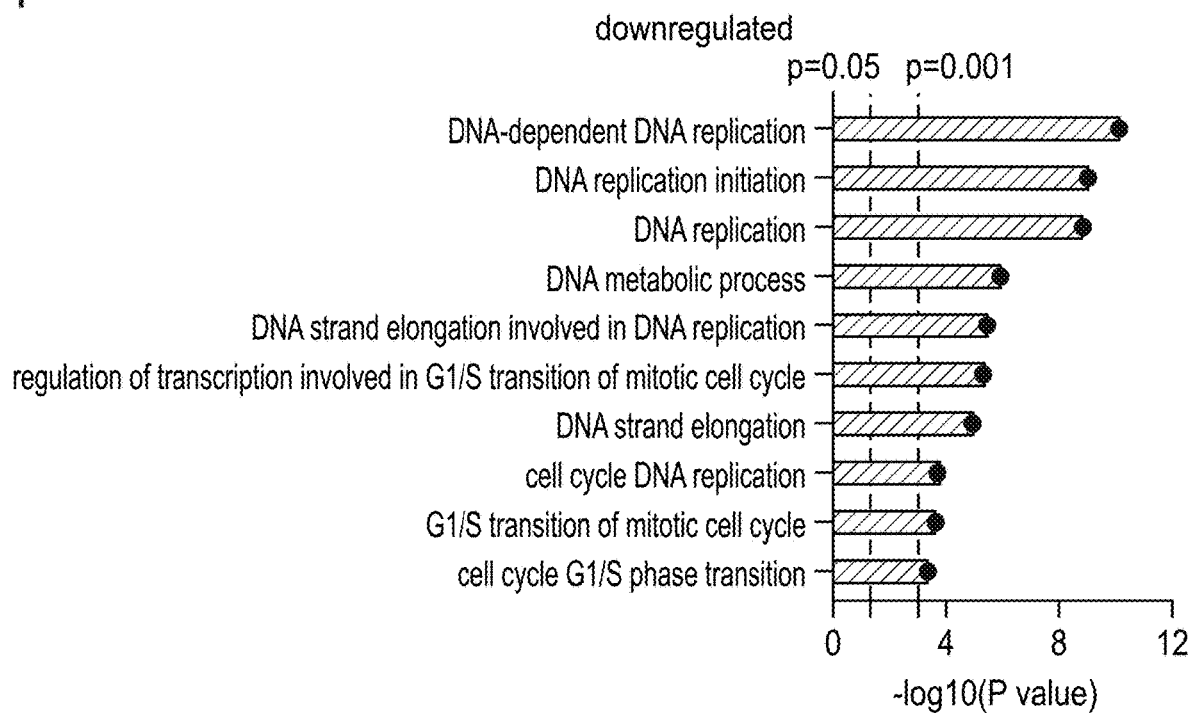
Figure 3:
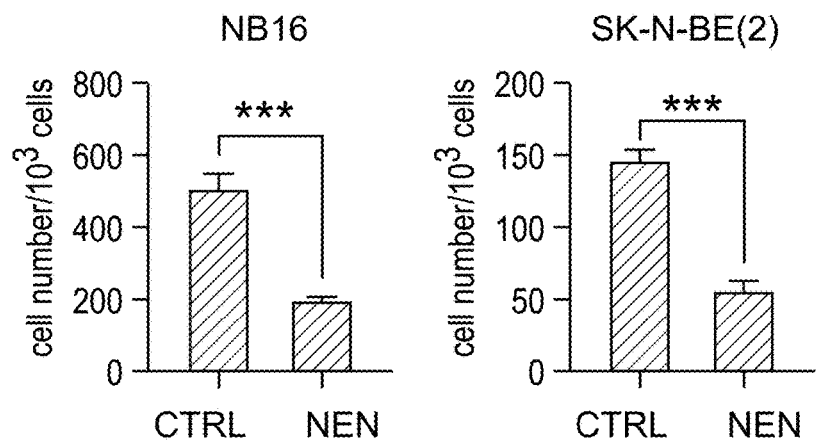
Figure 3:
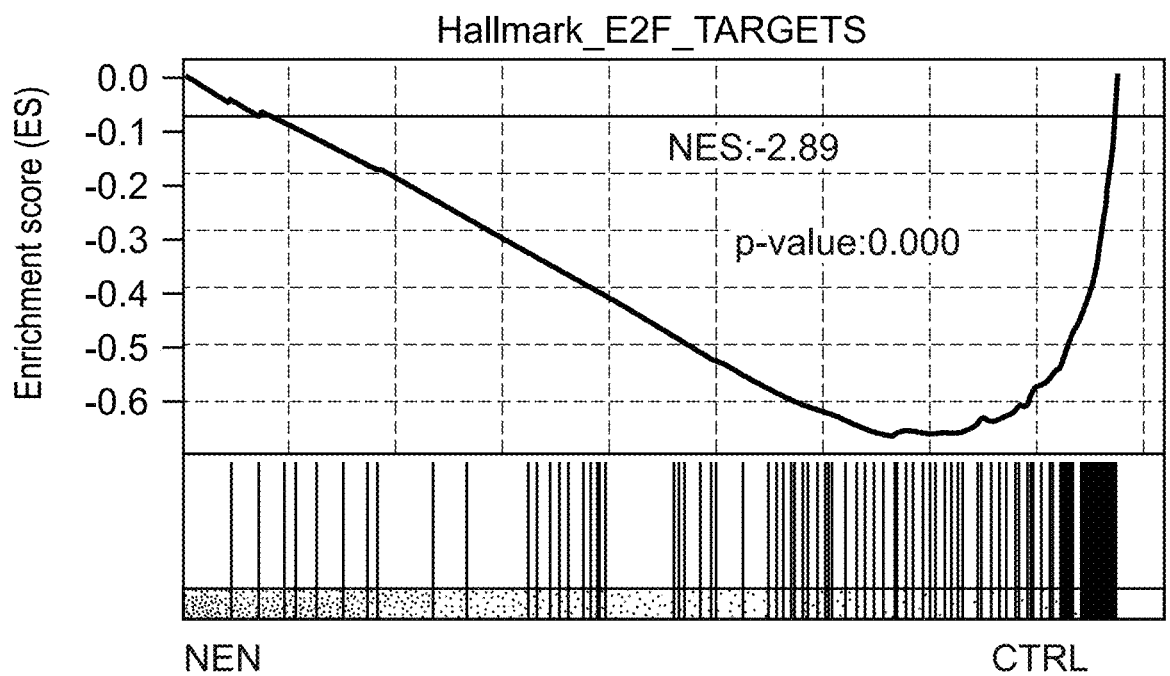
Figure 3:
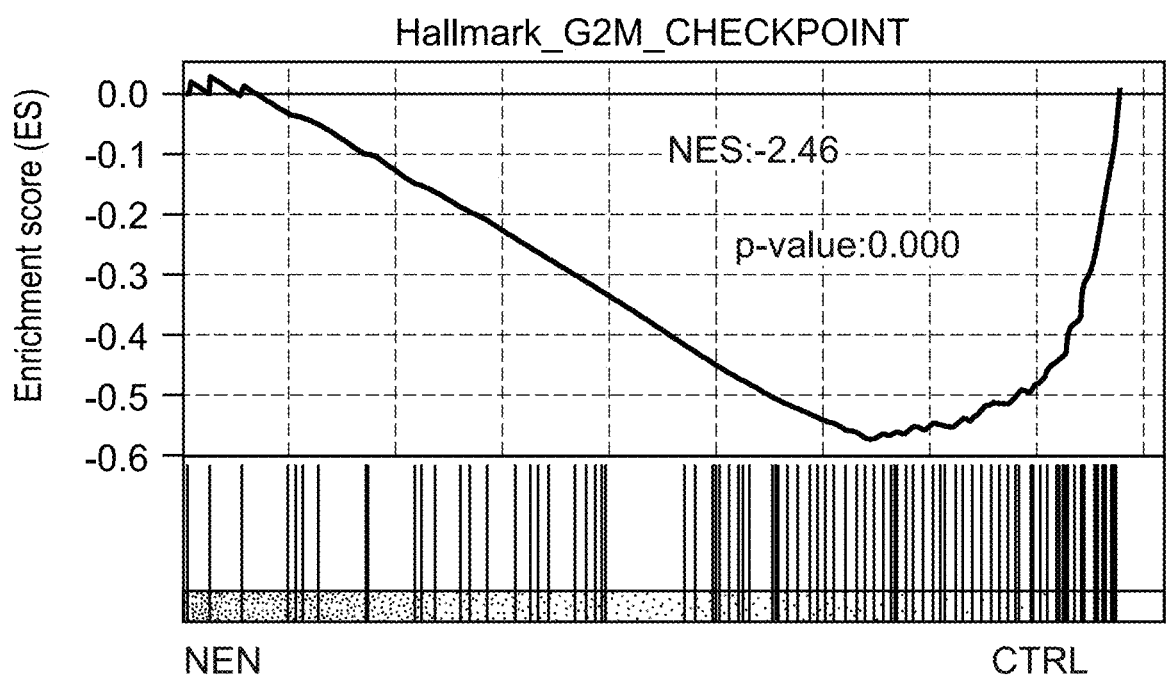
Figure 3:
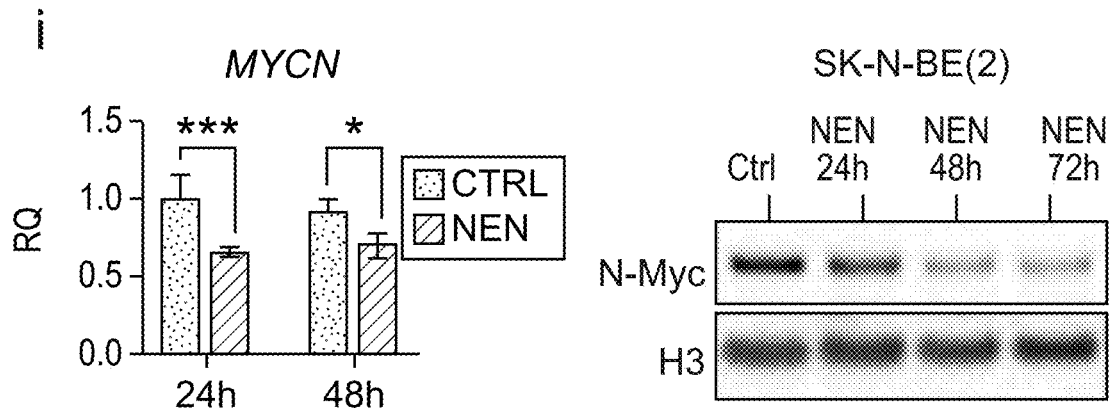
Figure 3:
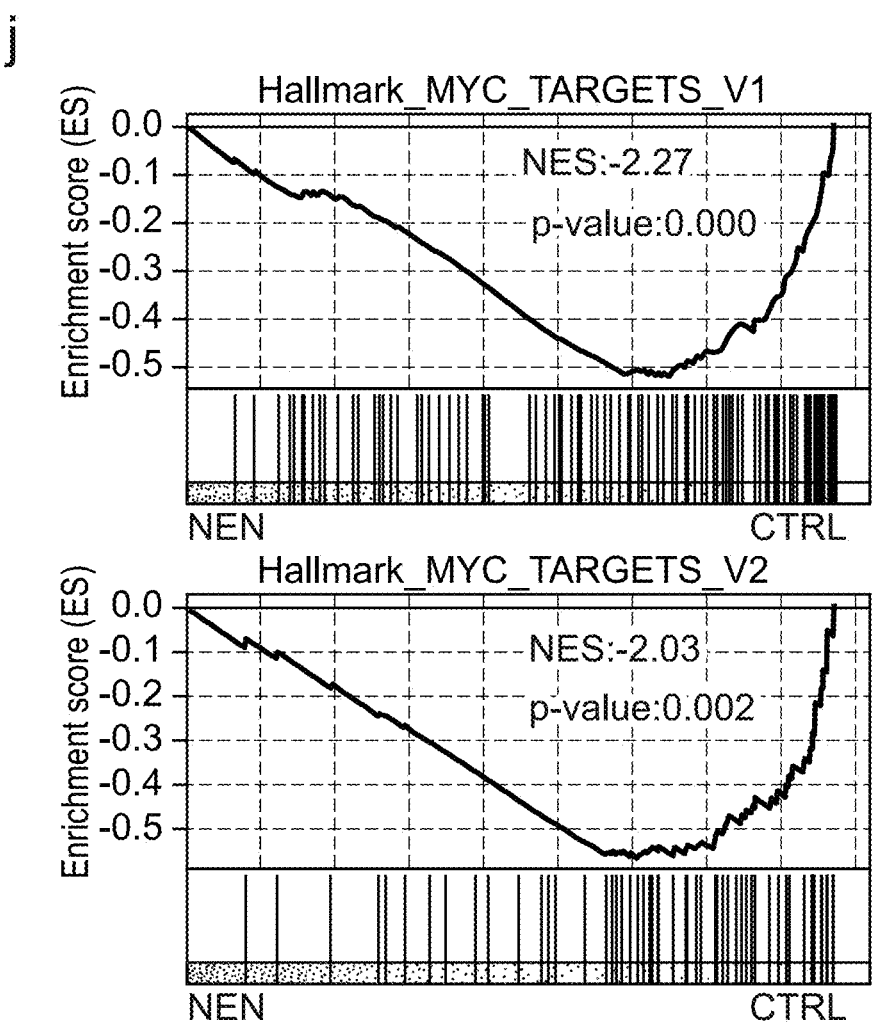

Mitochondrial uncoupling promotes neuroblastoma cell differentiation. To investigate how NEN treatment alters the global gene expression profile, we performed RNA-seq in SK-N-BE(2) cells treated with DMSO or NEN for 16 h. Corresponding to the DNA demethylation effect of NEN, 495 genes were significantly upregulated while 224 genes were downregulated by NEN treatment with a sleuth q-value<0.05 and fold change estimate b>abs(ln(2)) (FIG. 3a). The distribution of gene expression in the RNA seq were presented in volcano plot (FIG. 3b). The upregulated genes were enriched in multiple pathways including neurogenesis, nervous system development and neuron differentiation (FIG. 3c). Consistent with the pathway enrichment result, NEN treatment induced neuron differentiation morphology change in both SK-NE-BE(2) and NB16 cells, as determined by the neurite length measurement and immunofluorescence staining against neuron differentiation marker β-tubulin III (FIGS. 3d and e). In contrast, the NEN-downregulated genes were enriched in pathways involved in DNA replication and cell cycle progression (FIG. 3f). As expected, NEN treatment significantly inhibited cell proliferation (FIG. 3g). In addition, Gene Set Enrichment Analysis (GSEA) of the RNA-seq results showed that NEN treatment significantly deviated from two important cell division hallmark "E2F-TARGETS" and "G2M_CHECKPOINT" when compared to control (CTRL) treatment (FIG. 3h), indicating downregulation of cell division-related genes. Intriguingly, it was reported that E2Fs transcriptionally upregulates MYCN, the key oncogenic factor that is amplified in neuroblastoma and associated with poor patient outcome. NEN treatment significantly reduced the mRNA and protein level of N-Myc (FIG. 3i). Consistent with the reduced N-Myc protein levels, GESA analysis showed that NEN treatment significantly deviated from hallmark "MYC_TARGETS_V1" and "MYC_TARGETS_V2" when compared to control (CTRL) treatment (FIG. 3j), indicating that NEN reduced the expression N-Myc targeted genes.

Figure 4:
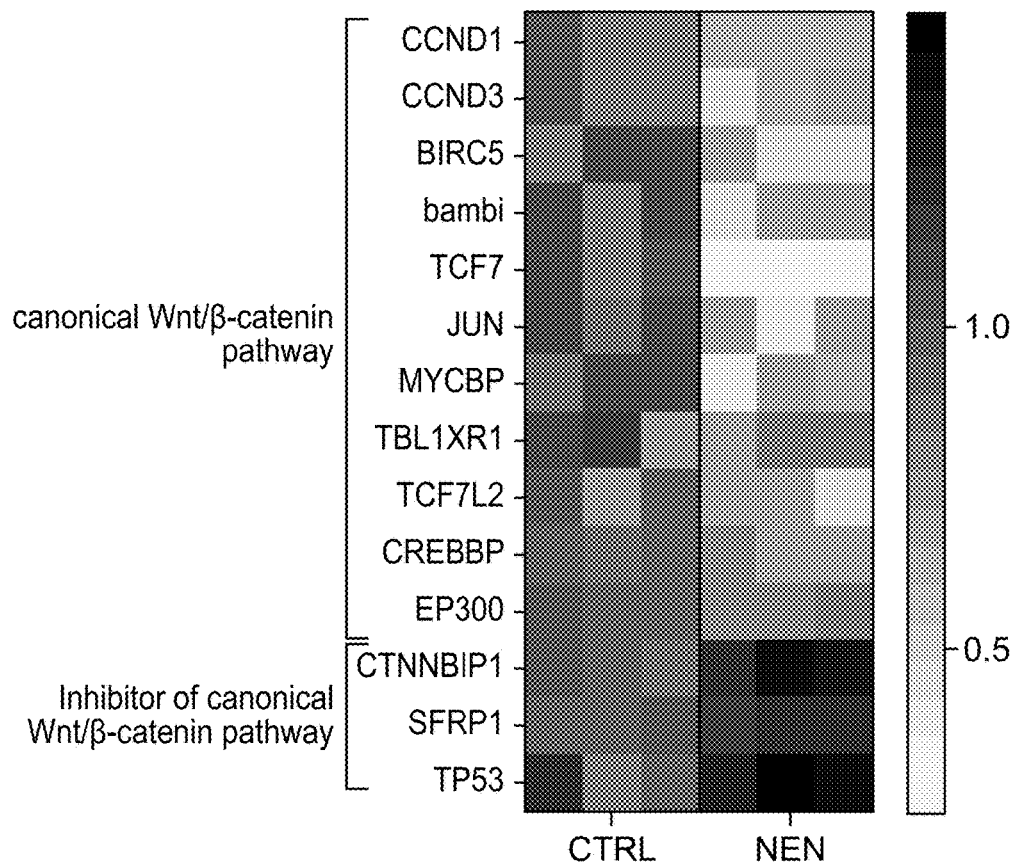
FIG. 4a-FIG. 4e. Mitochondrial uncoupling activated the p53 pathway and inhibited the Wnt/β-catenin pathway.
Figure 4:
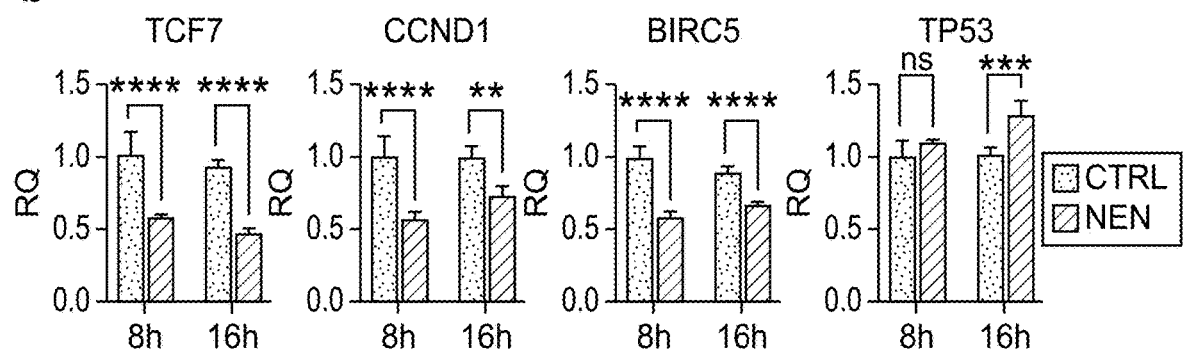
Figure 4:
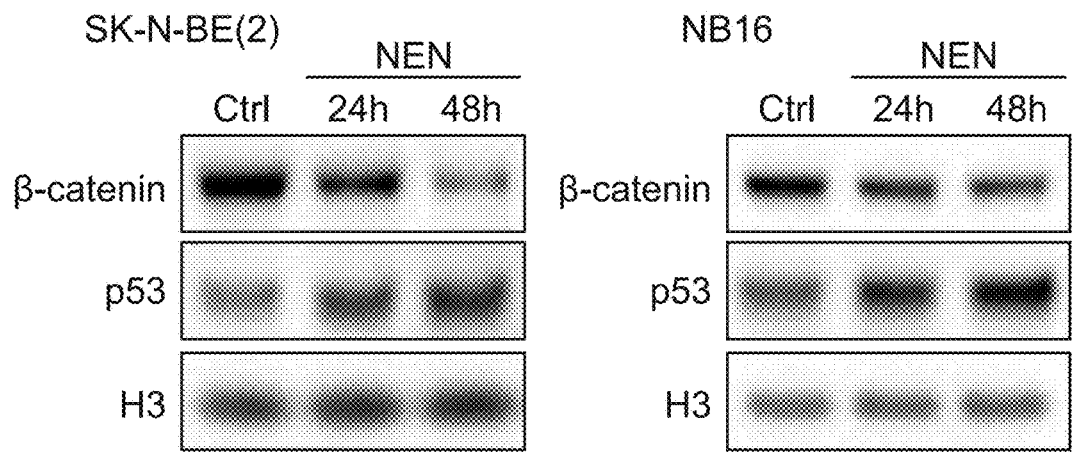
Figure 4:
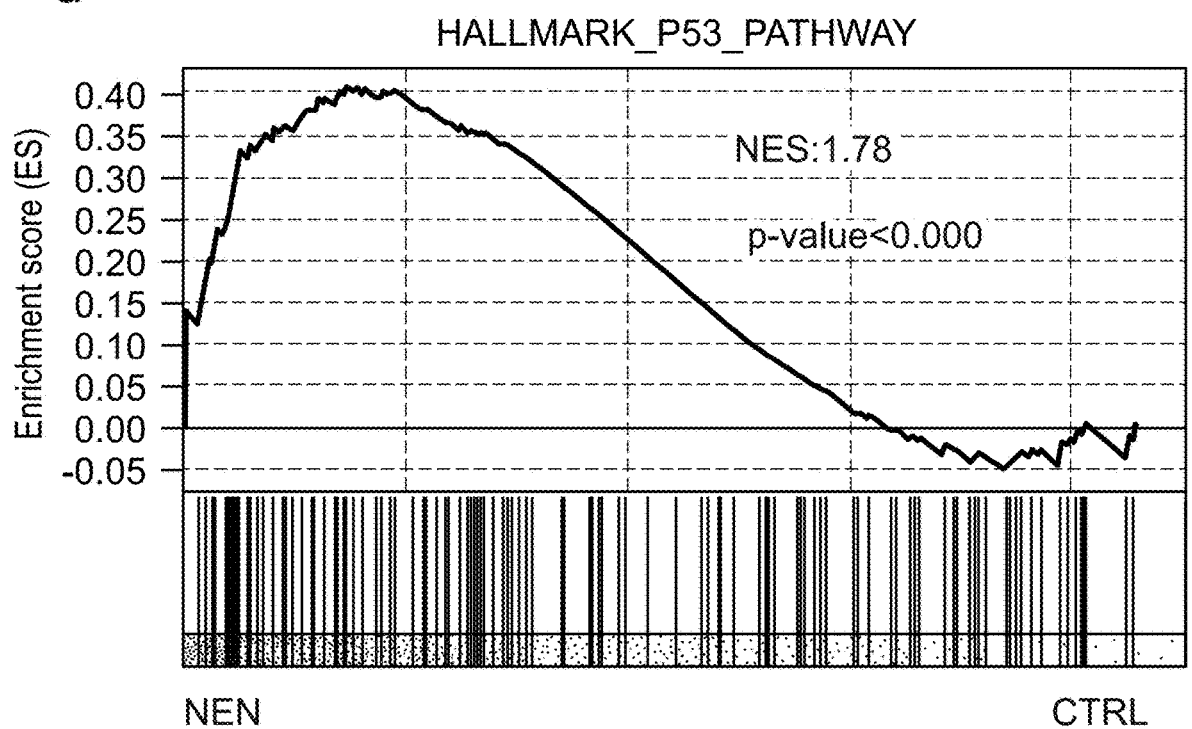
Figure 4:
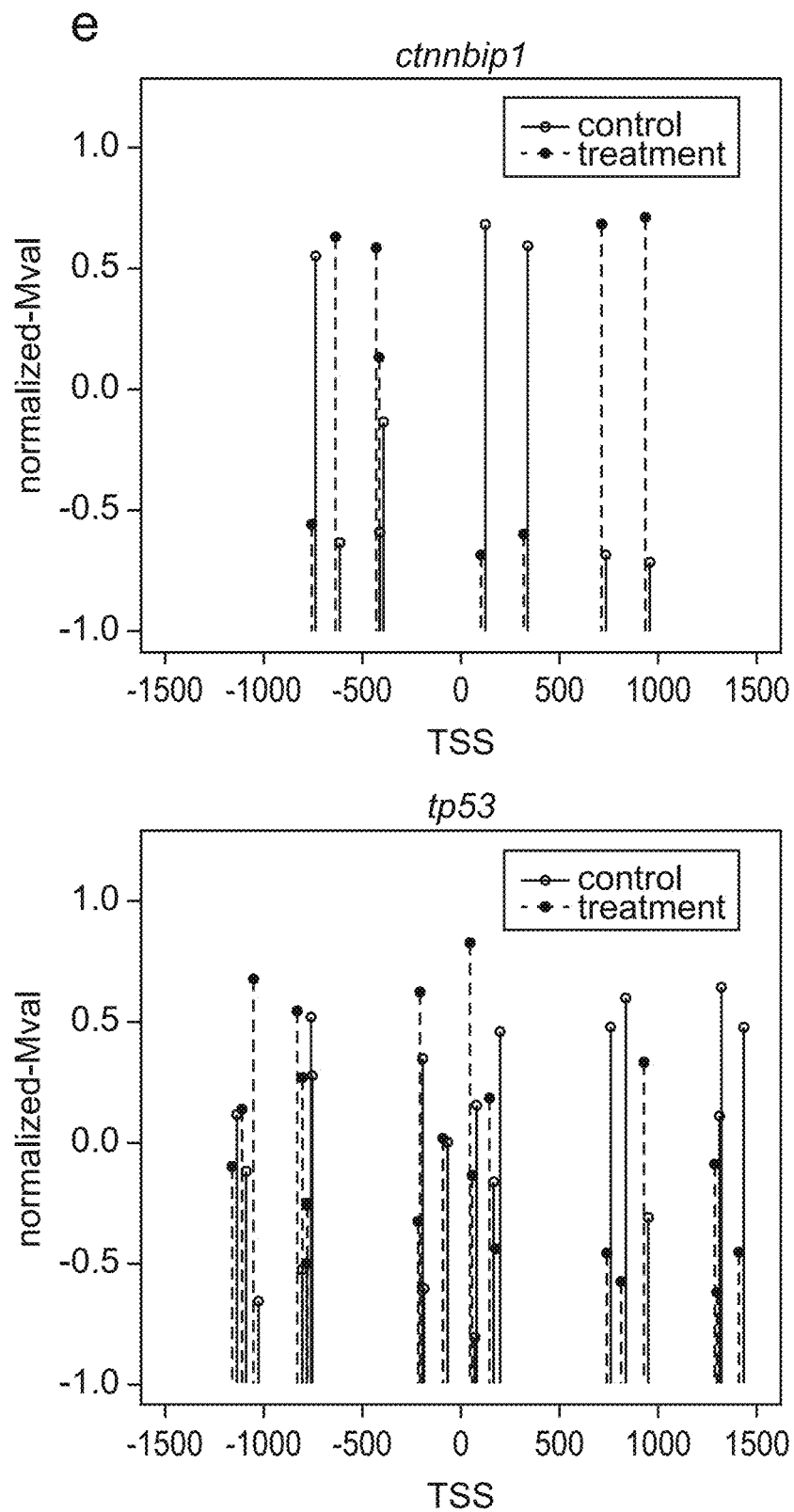

Mitochondrial uncoupling activated the p53 pathway and inhibited the Wnt/β-catenin pathway. Previous report showed that α-KG could activate p53 and inhibit Wnt/β-catenin pathway. Thus, we wondered whether NEN treatment also modulates these two pathways. As expected, NEN treatment reduced the expression of canonical Wnt/β-catenin target genes and upregulated the gene expression of inhibitor of Wnt/β-catenin pathway including TP53 according to the RNA-seq data (FIG. 4a). We validated these results using RT-qPCR (FIG. 4b). Consistent to gene expression changes, NEN treatment reduced the expression of β-catenin and increased the expression of p53 (FIG. 4c). GESA analysis showed that NEN treatment significantly increased p53 pathway gene expression (FIG. 4d). In addition, DNA methylation levels of multiple CpG sites in the promoter region of p53 and CTNNBIP1 were also upregulated/downregulated (FIG. 4e).

Figure 5:
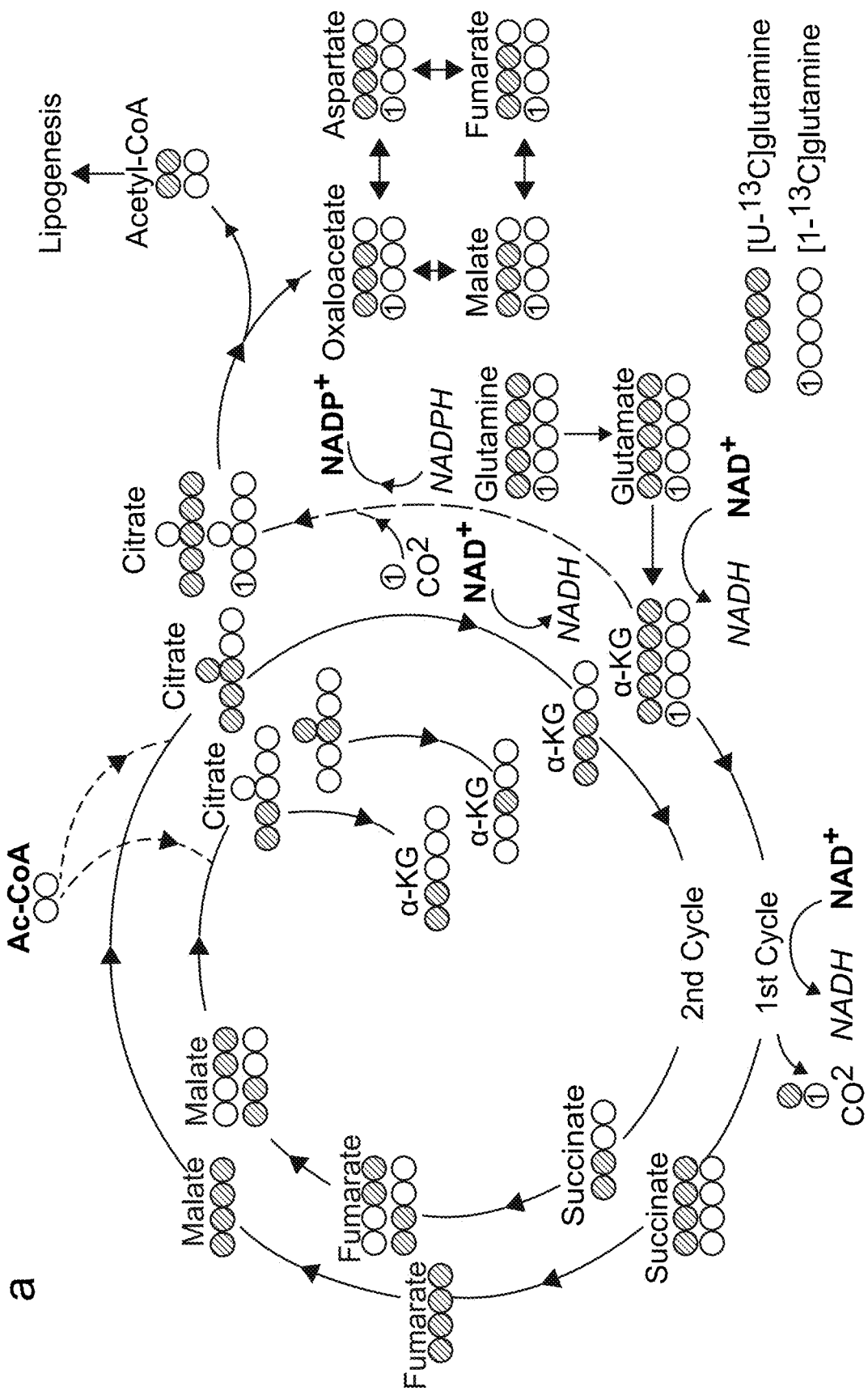
Figure 5:
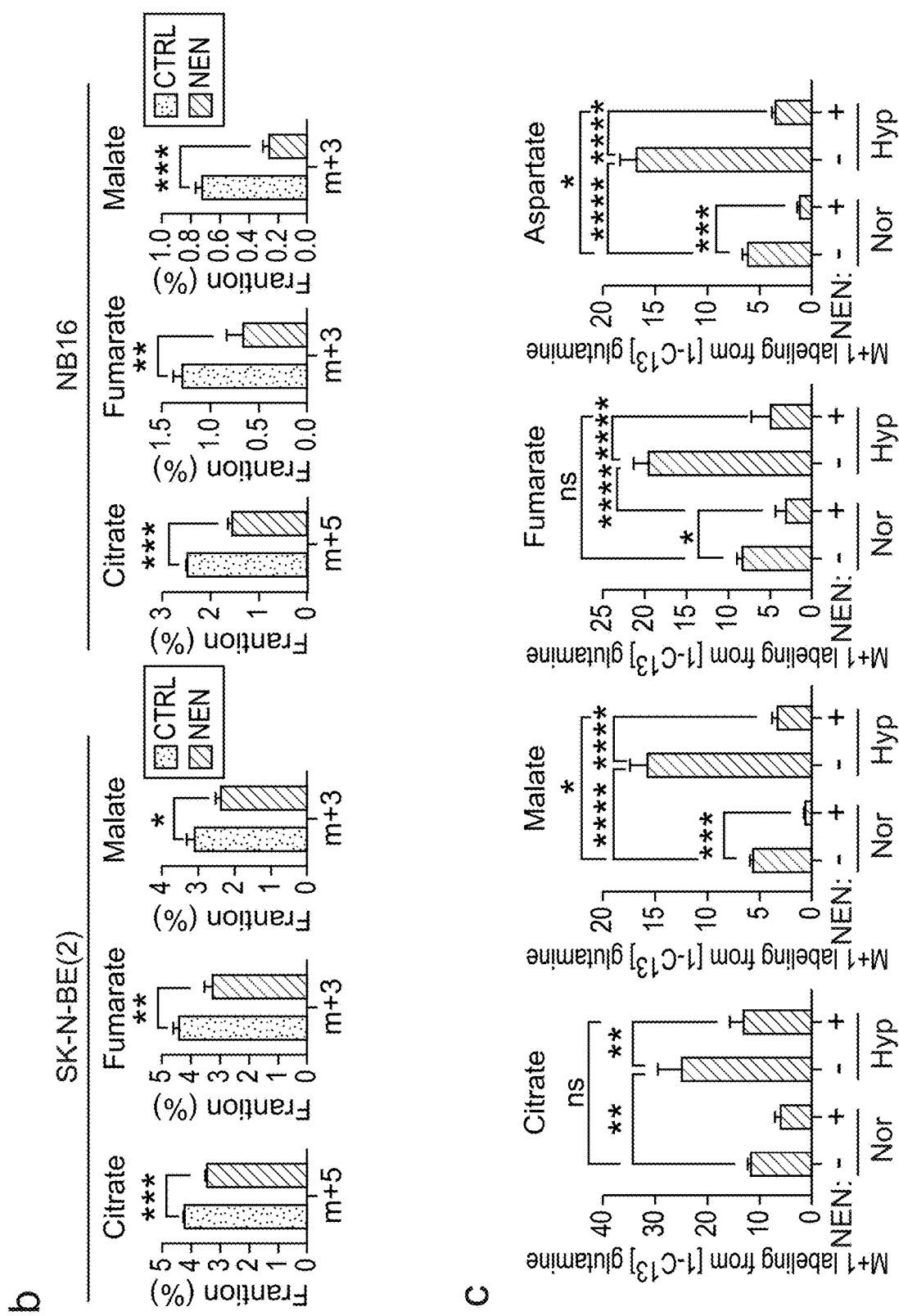

Mitochondrial uncoupling inhibits reductive carboxylation. Cancer cells under hypoxia or carrying mutations that suppress mitochondrial function display reductive carboxylation, a reaction that converts α-KG to citrate to provide acetyl-CoA for lipid synthesis (FIG. 5a). In the U-$^{13}C_5$-glutamine tracing assay, we found that NEN treatment significantly inhibited reductive carboxylation flux, as determined by the decreased labelling faction of m+5 citrate, m+3 fumarate, and m+3 malate (FIG. 5b). We next tested whether mitochondrial uncoupling could also reverse reductive carboxylation under hypoxia. When [1-$^{13}$C]-glutamine is used as a tracer, labelling carbon will only be detected in metabolites from the reductive carboxylation pathway (m+1 citrate, m+1 fumarate, m+1 malate, and m+1 aspartate) (FIG. 5a). NEN treatment not only reduced basal reductive carboxylation flux under normoxia, but also fully repressed hypoxia-induced reductive carboxylation flux (FIG. 5c), indicating that the mitochondrial uncoupler NEN is an effective inhibitor of reductive carboxylation.

Figure 6:
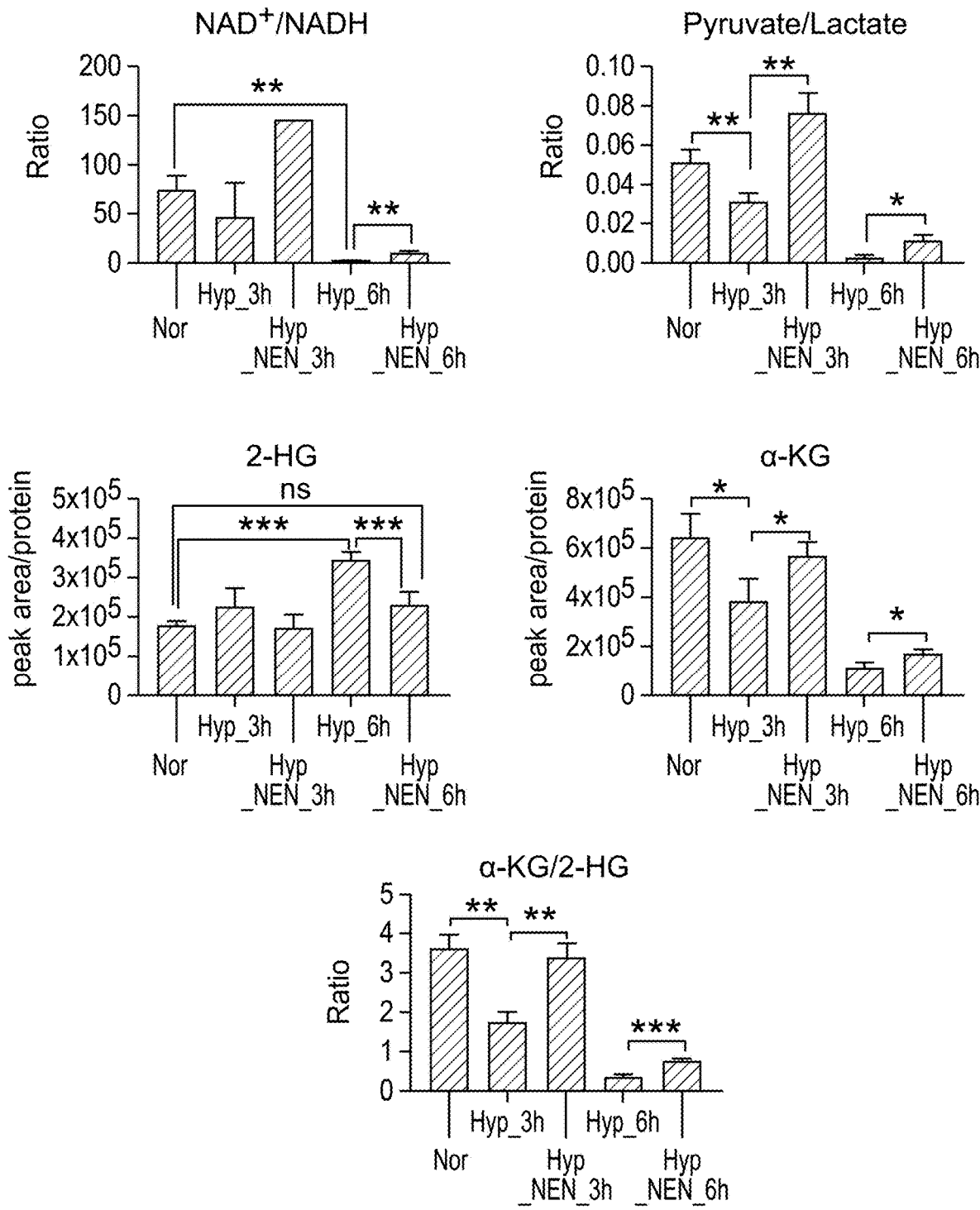
FIG. 6a-FIG. 6d. NEN inhibit 2-HG generation and DNA hypermethylation under hypoxia.
Figure 6:
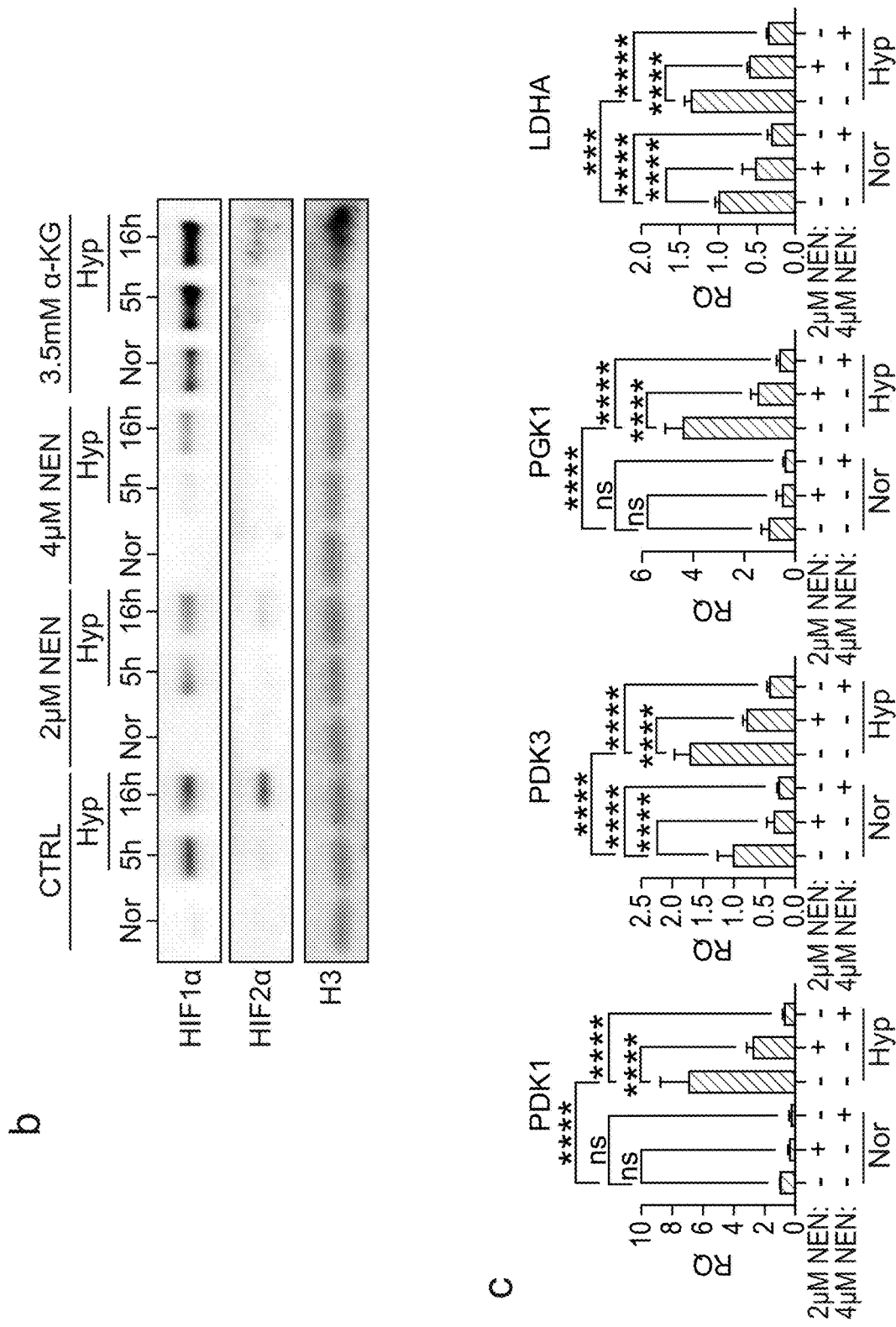
Figure 6:
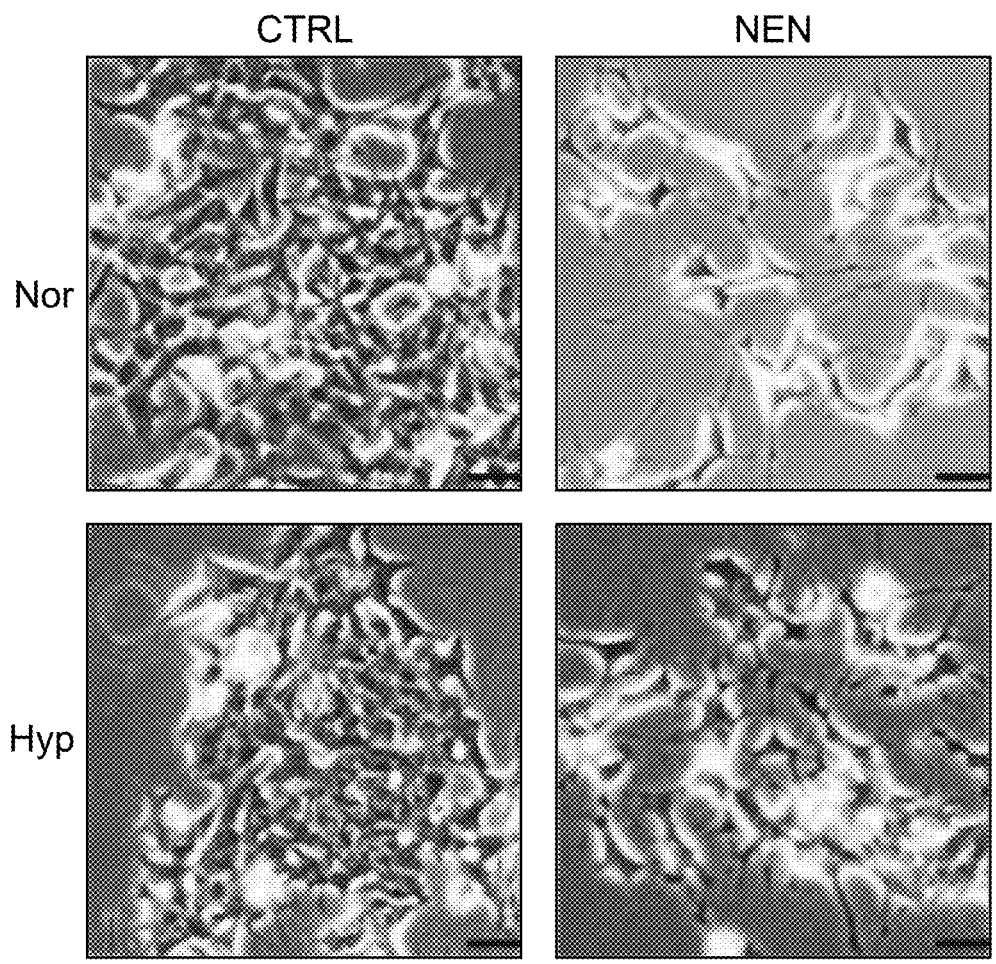
Figure 6:
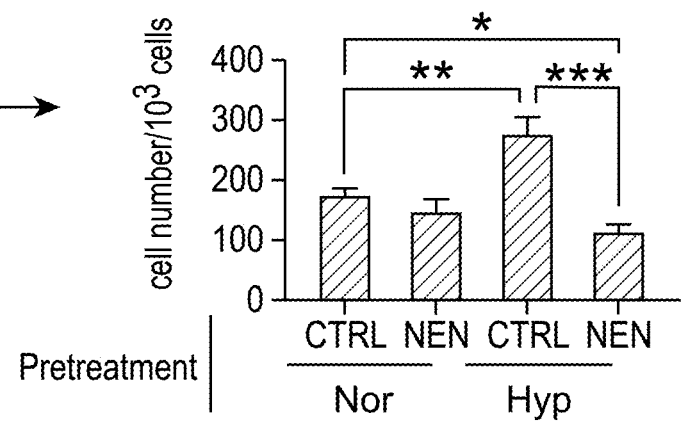

Mitochondrial uncoupling inhibits 2-HG generation and DNA hypermethylation under hypoxia. Clinically, tumor hypoxia is a significant obstacle to treatment because hypoxic tumor cells are more resistant to radiation and chemotherapy. Under hypoxia, due to reduced NAD$^+$/NADH ratio, α-KG is reduced and converted to L-2-HG, which may repress α-KG-dependent dioxygenase, including TET DNA demethylase. We found that NEN treatment could partially restore NAD$^+$/NADH and pyruvate/lactate ratios under hypoxia (FIG. 6a). Importantly, NEN treatment partially restored α-KG and significantly reduced 2-HG levels under hypoxia (FIG. 6a). Intriguingly, we found that NEN treatment but not α-KG inhibited the accumulation of HIF1α and HIF2a protein (FIG. 6b) and reduced expression of HIF target genes such as pdk1, pdk3, pgk1 and Idha (FIG. 6c). In addition, α-KG enhanced the accumulation of HIF1α in both normoxia and hypoxia condition, possibly because supplemented α-KG was converted to 2-HG (FIG. 6b). Importantly, we found that 4 days hypoxia pretreatment increased cell proliferation when the cells were replated under normoxia condition (with no treatment). However, when cells were pretreated under hypoxia with NEN, this gain of proliferation advantage from hypoxia pretreatment was blocked (FIG. 6d).

Figure 7:
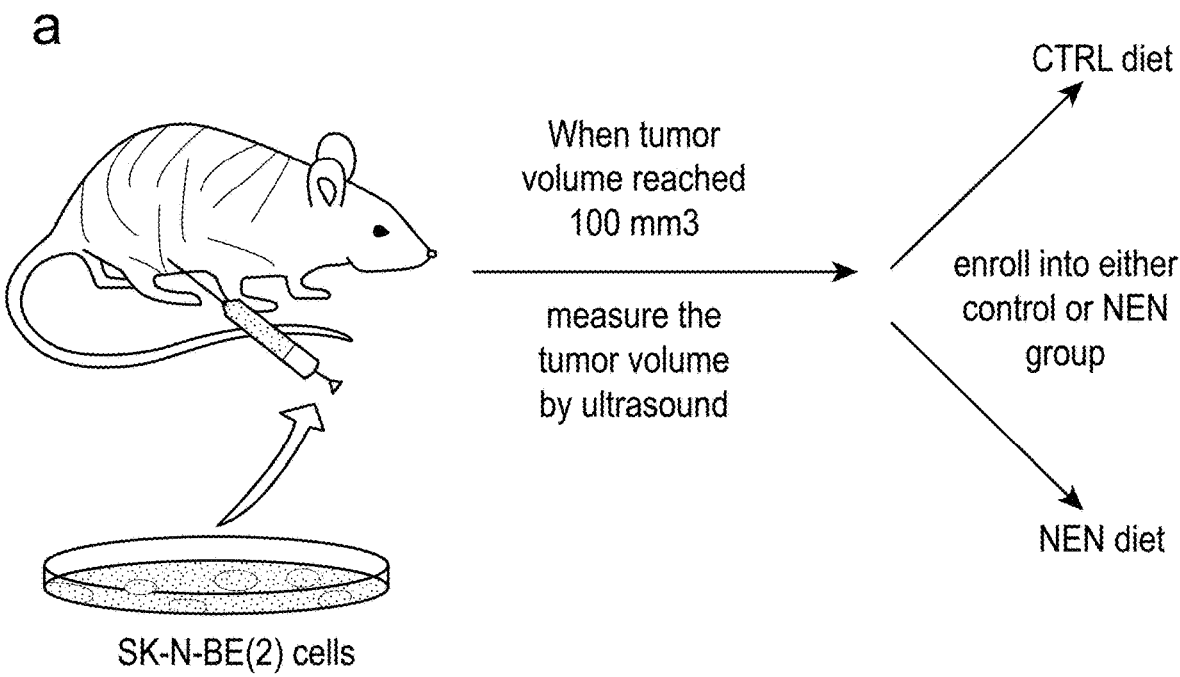
FIG. 7a-FIG. 7f. NEN show anti-tumor effect in vivo.
Figure 7:
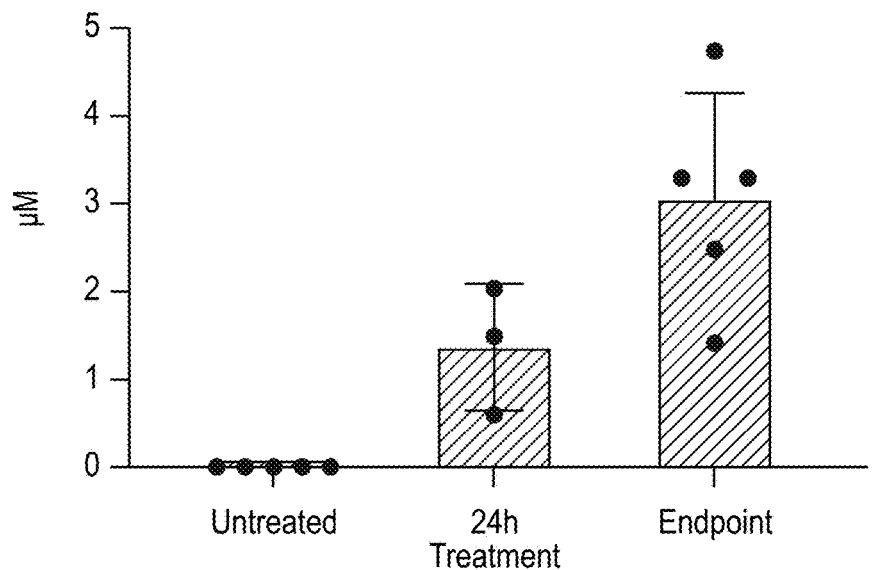
Figure 7:
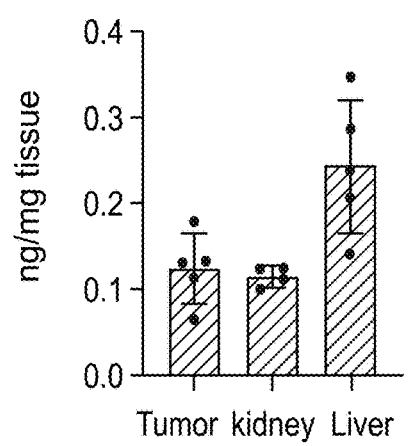
Figure 7:
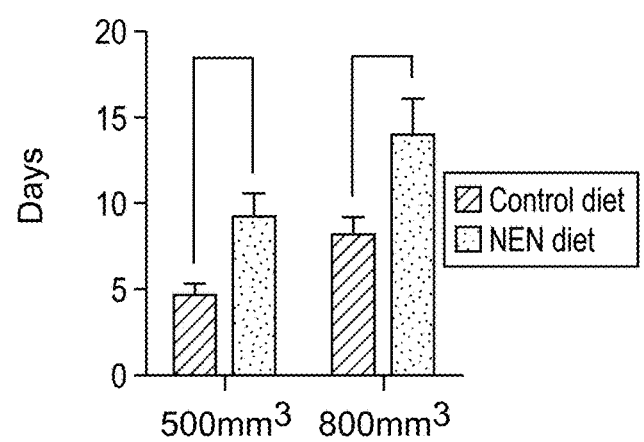
Figure 7:
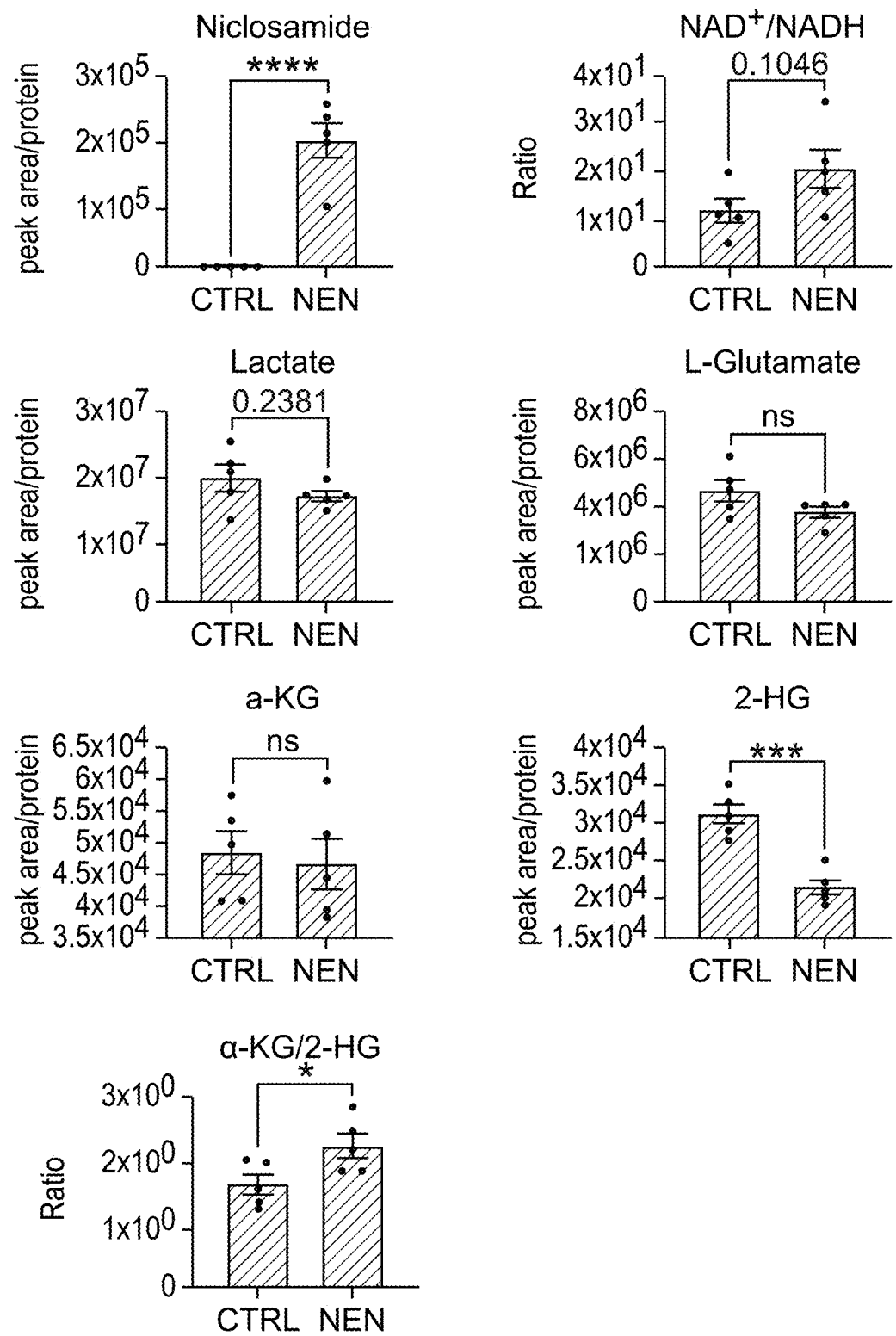
Figure 13:
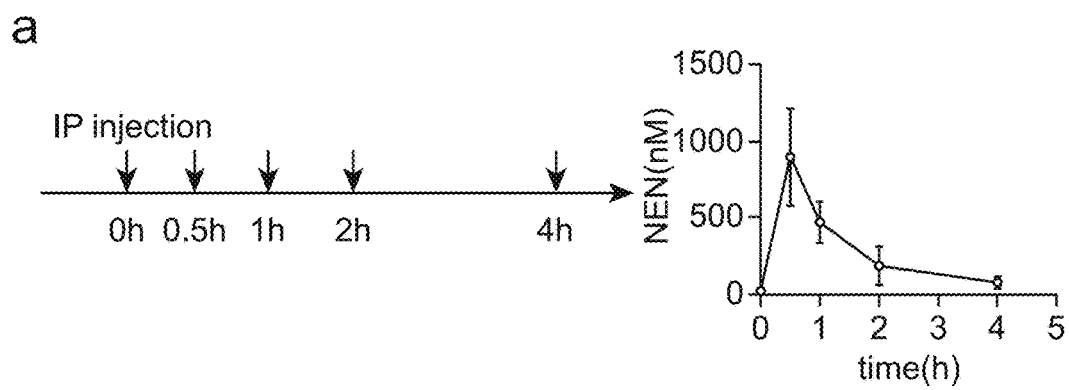
FIG. 13a. Prognosis analysis of neuroblastoma databases.

NEN supplementation inhibits growth of orthotropic neuroblastoma in vivo. Next, we examined whether NEN has anti-growth effect in vivo using an orthotopic neuroblastoma xenograft model. Because intraperitoneal injection of NEN shows poor plasma pharmacokinetics (FIG. 13a), we used a diet that contains 2000 ppm NEN for treatment delivery (FIG. 7a). LC/MS analysis indicated that dietary NEN supplementation led to abundant NEN accumulation in plasma (1-3 μM) (FIG. 7b). The NEN accumulation in xenograft tumors is comparable to levels found in the kidney, although lower than levels in the liver (FIG. 7c). NEN supplementation significantly slowed tumor growth as compared to control group (FIG. 7d). In addition, NEN treatment increased NAD$^+$/NADH and slightly reduced lactate level in the tumor (FIG. 7e). Importantly, 2-HG level was reduced and the α-KG/2-HG ratio were increased in the tumor under NEN treatment tumor (FIG. 7e). Furthermore, tumor cells from NEN-treated group had much fewer enlarged prominent nucleoli (FIG. 7f), which indicates active ribosome biogenesis and worse prognosis in NB patients. Importantly, N-Myc and β-catenin protein expression was significantly reduced in the NEN-treated xenografts (FIG. 7f). This is consistent with our in vitro observation (FIGS. 3i and 4c).

Figure 8:
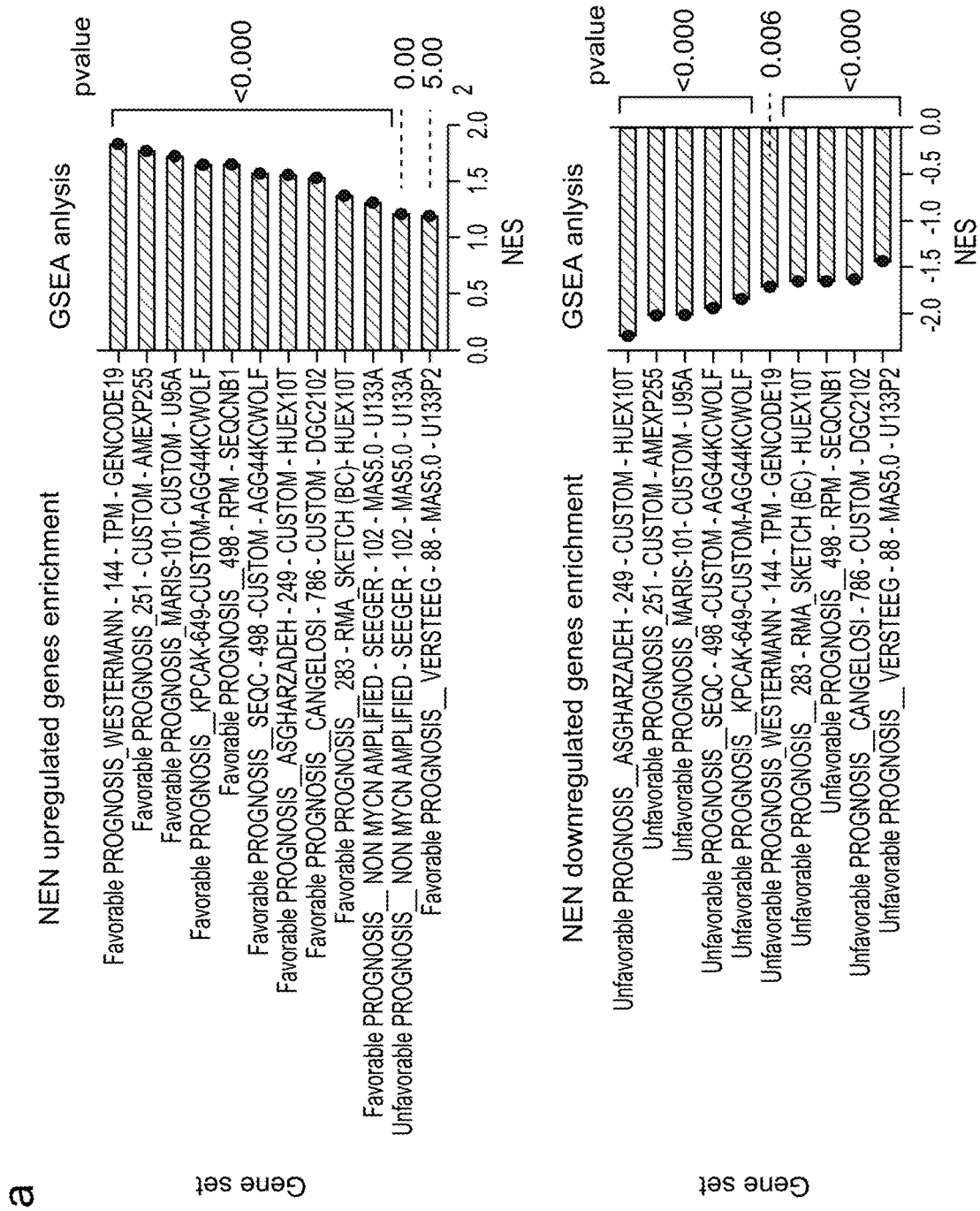
FIG. 8a-FIG. 8d. NEN showed favorable prognosis potential.
Figure 8:
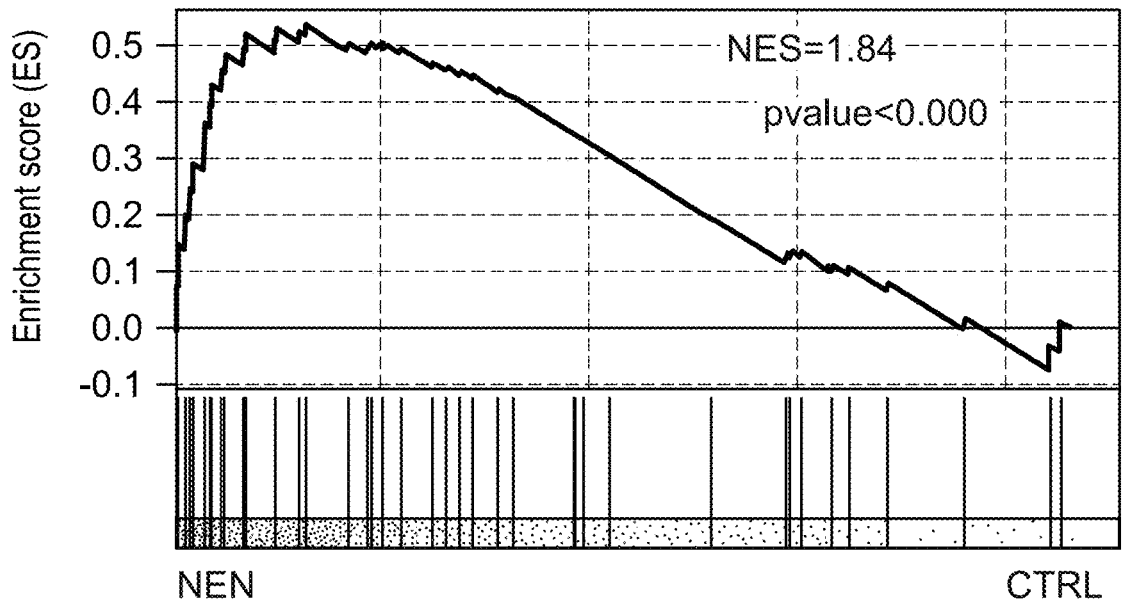
Figure 8:
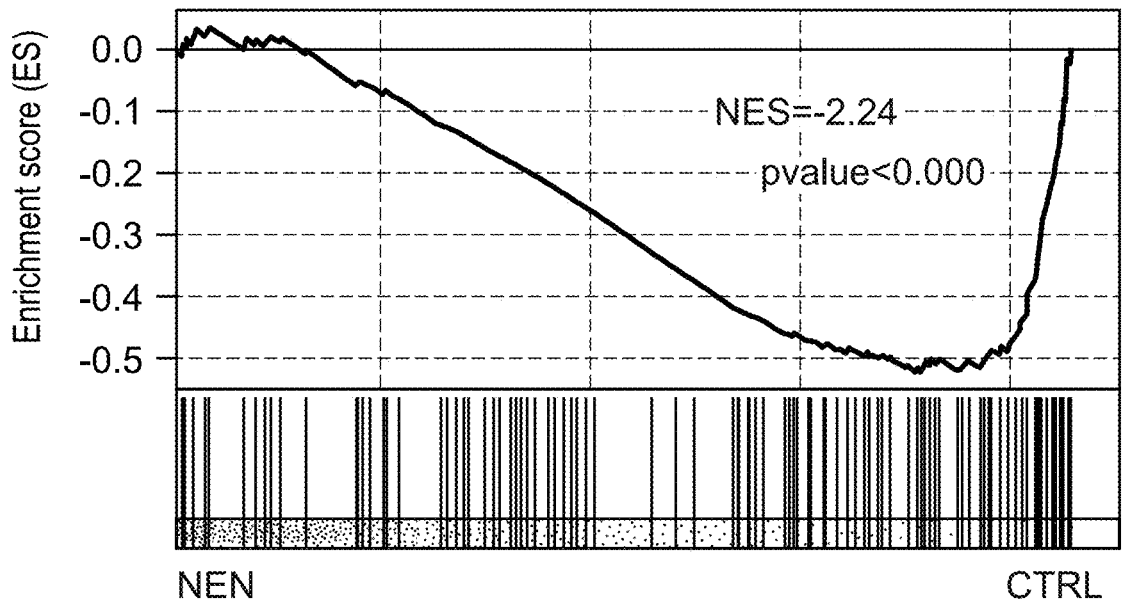
Figure 8:
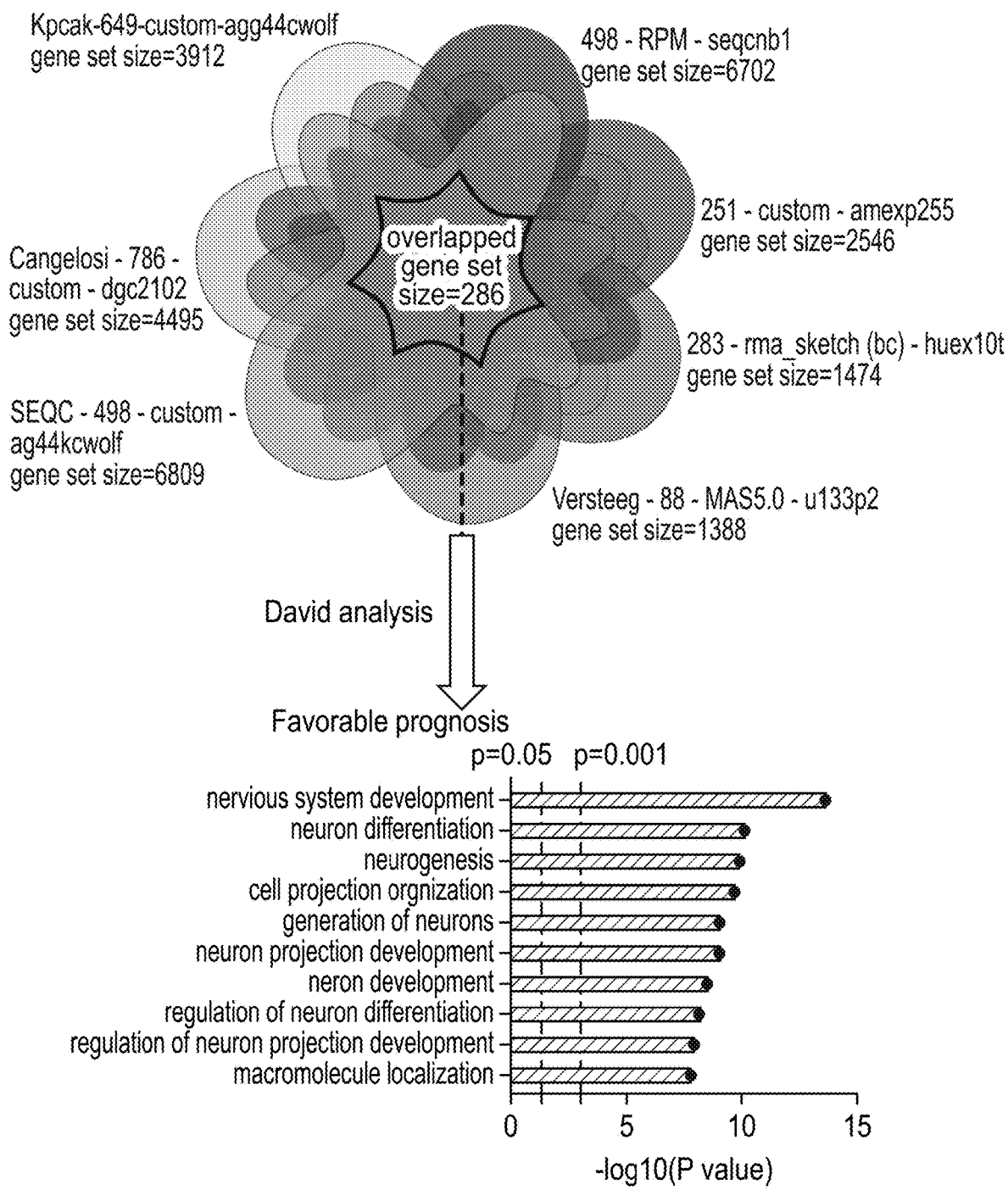
Figure 8:
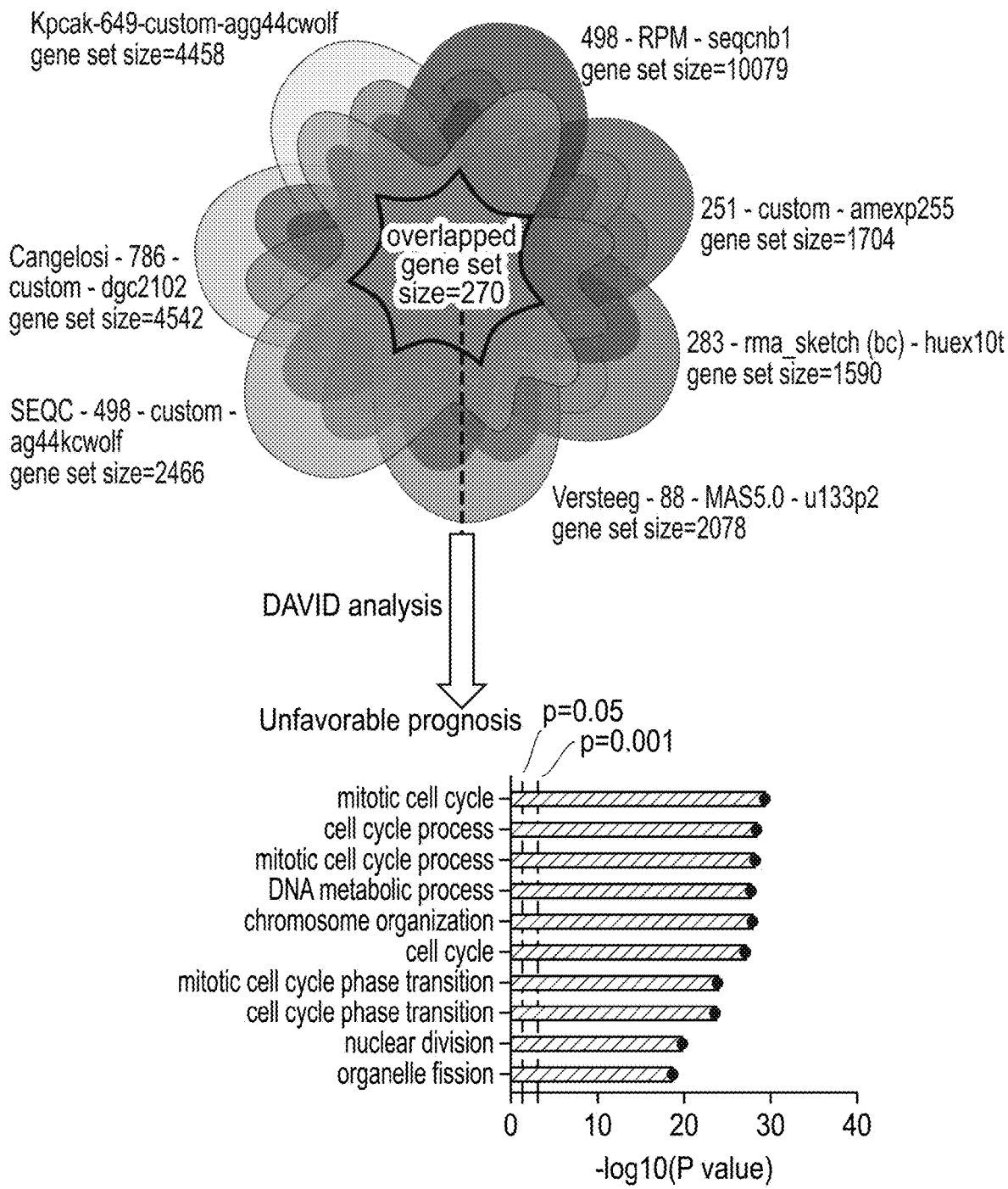

NEN-induced gene expression changes indicate favorable prognosis in neuroblastoma patients. To further explore the clinical relevance of NEN-induced gene expression profile changes, we integrated the gene expression signature of RNA-seq result from the NEN treatment experiment, and 11 neuroblastoma patient gene expression profiles from the R2 database. Using the datasets from R2 database, we generated gene sets that indicated favorable prognosis or unfavorable prognosis from the 11 neuroblastoma patient studies (The p-value of Kaplan-Meier analysis of each gene is less than 0.05). Consequently, these gene sets were defined as pathways for GSEA analysis. Surprisingly, NEN-upregulated genes are enriched in all the favorable prognosis gene sets except one (FIG. 8a, b). In contrast, NEN-downregulated genes are enriched in unfavorable prognosis gene sets (FIG. 8a, b). The only exception is that NEN-upregulated genes are enriched in an unfavorable prognosis gene set derived from N-Myc non-amplification neuroblastomas. A potential explanation for this discrepancy is that the RNA-seq data was generated from SK-N-BE(2) cells, which are N-Myc-amplified (FIG. 3i). In addition, we constructed sets of overlapped genes from 7 gene sets that contain more than 1000 genes; namely, an overlapped "favorable prognosis gene set" with 286 genes and an overlapped "unfavorable prognosis gene set" with 270 genes (FIG. 8c, d). These two genes set were submitted to pathway enrichment through online Database for Annotation, Visualization and Integrated Discovery (DAVID) analysis. The overlapped favorable prognosis gene sets were enriched for multiple neuron differentiation terms while the overlapped unfavorable prognosis gene sets were enriched for cell-cycle related terms (FIG. 8c, d). Together these data show that NEN treatment reprograms the transcriptome to a gene expression profile that is associated with favorable prognosis in patients with N-Myc-amplified neuroblastoma.

Figure 14:
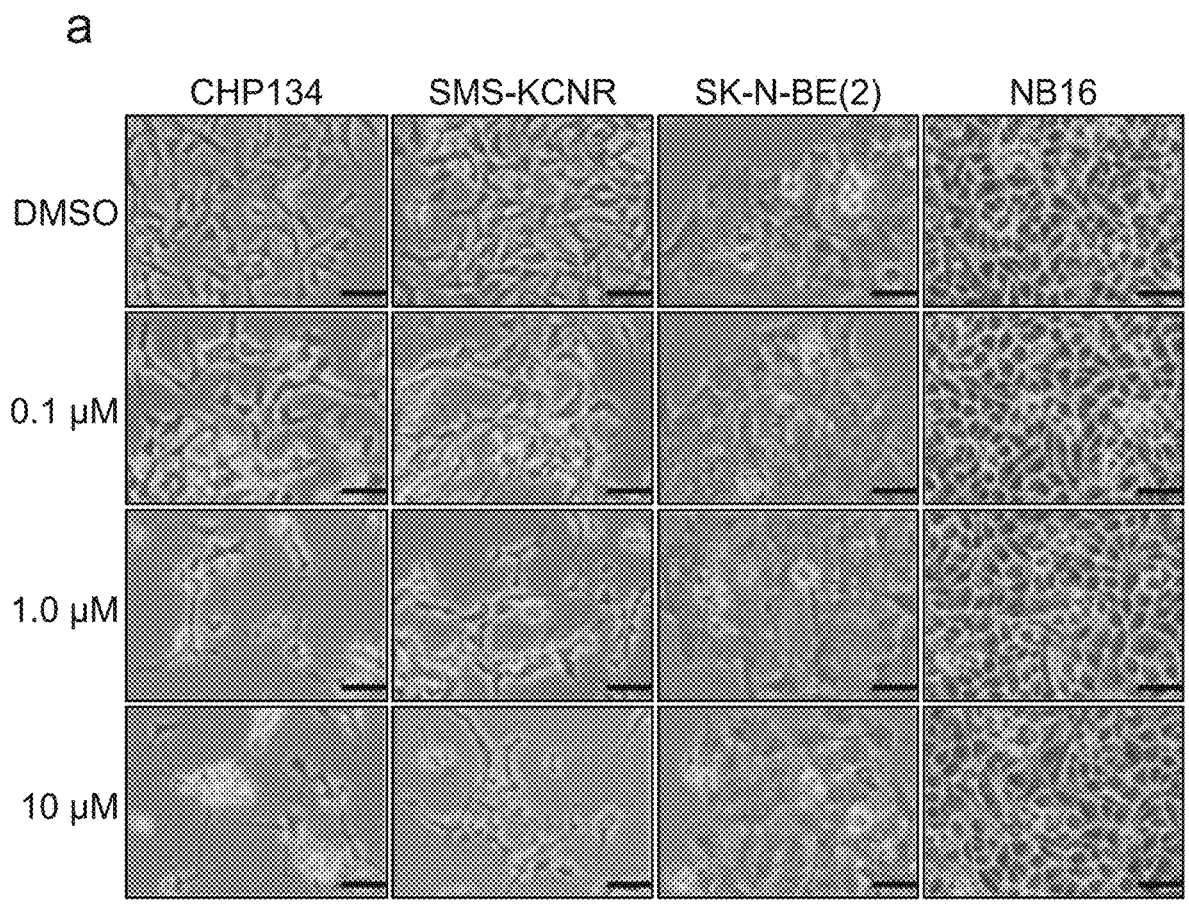
FIG. 14a-FIG. 14b. Certain neuroblastomas cell lines carry intrinsic RA-resistance.
Figure 14:
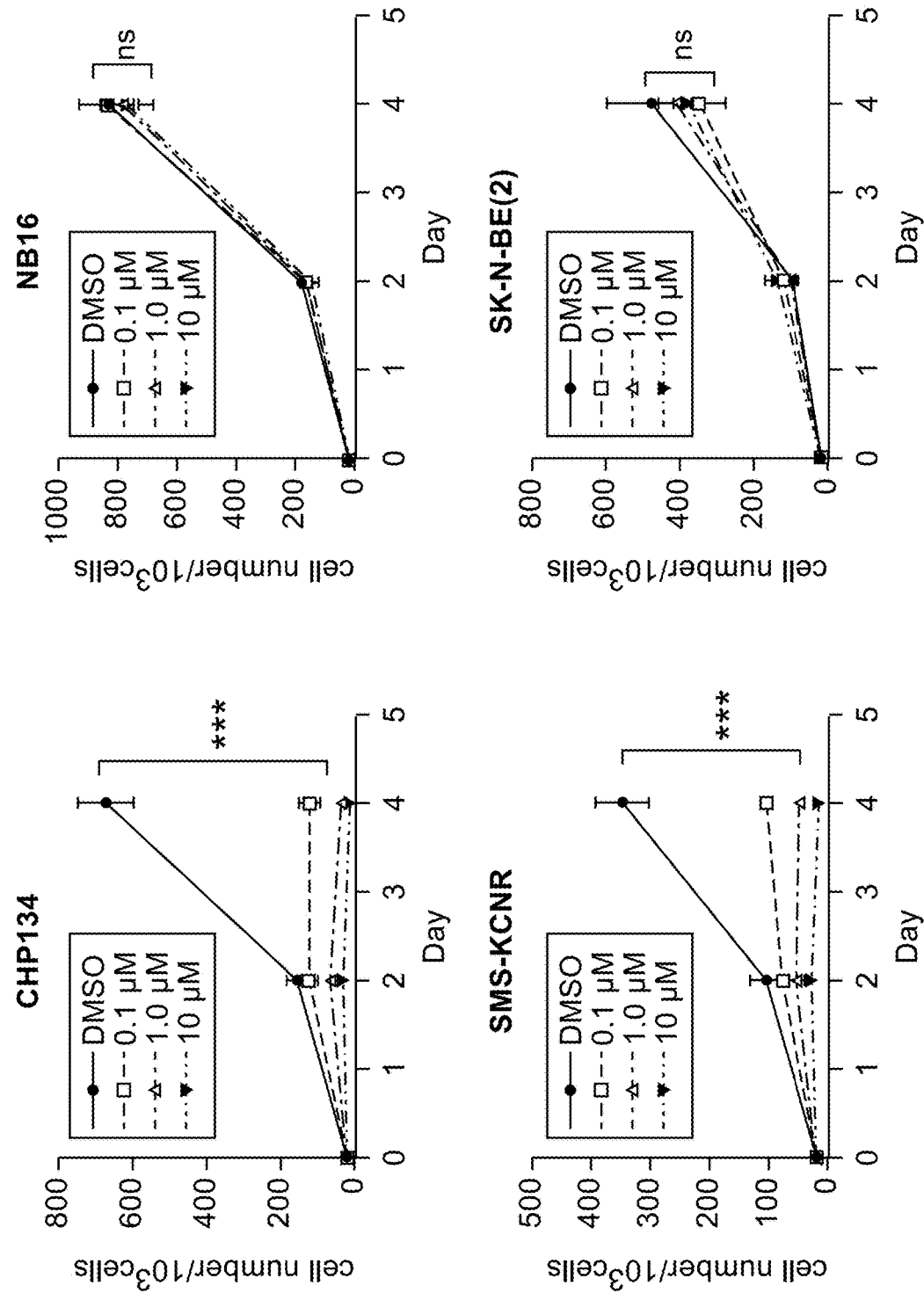
Figure 14:
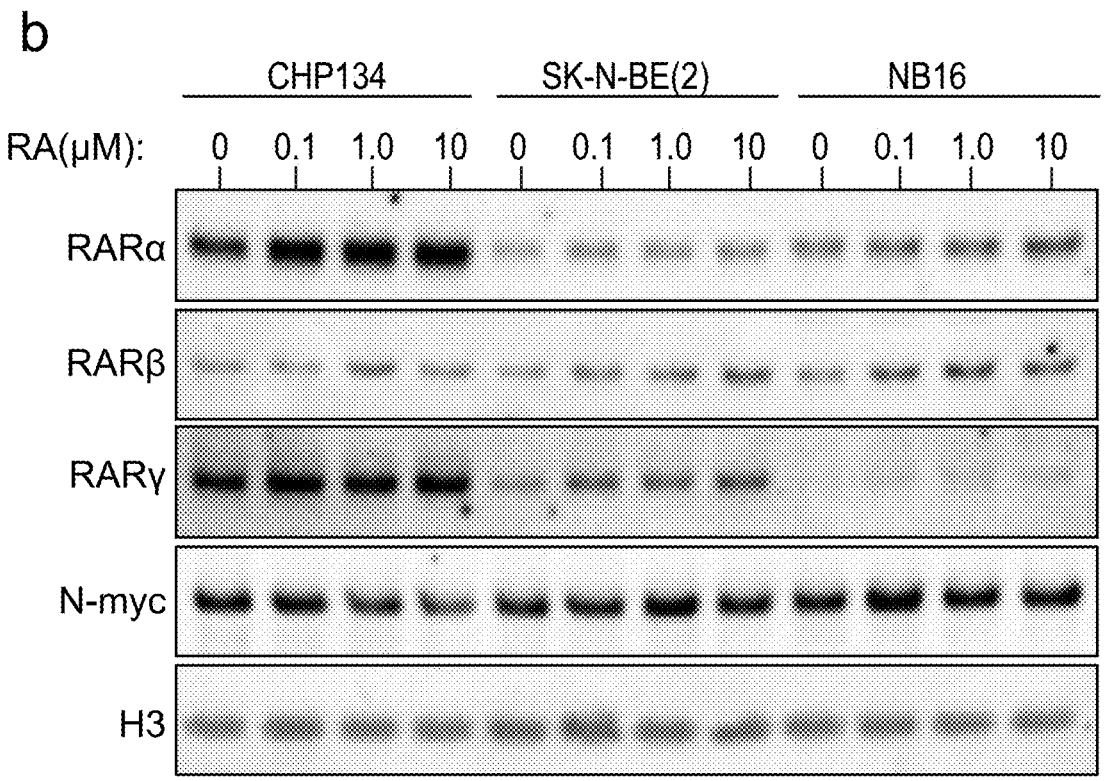

NEN treatment sensitizes the RA-resistant neuroblastoma cells to RA-induced differentiation. DNA hypermethylation of specific CpG islands in promoter region leads to silencing of tumor suppressors and cell differentiation markers, causing cell dedifferentiation and therapy resistance in many cancer types, including neuroblastoma. Retinoic acid (RA) induces neuroblastoma cell differentiation. Despite the significant response observed in vitro, no significant therapeutic responses were observed in clinical trials testing RA as a single agent in NB patients, suggesting NB cells develop resistance to RA treatment. We characterized our NB cell line collection into RA-sensitive and RA-resistant cell lines according to cell proliferation data and morphology change. RA treatment significantly induced neuron differentiation morphology in RA-sensitive cell lines CHP134 and SMS-KCNR (FIG. 14a), associated with proliferation arrest (FIG. 14b), while the RA-resistant cell lines SK-N-BE(2) and NB16 cells did not show differentiation morphology or proliferation arrest upon RA treatment (FIG. 14a, b). In addition, the RA-resistant SK-N-BE2 and NB16 cells not only have lower basal expression of RA receptors (RAR), but also less induction of RARα and RARγ upon RA treatment. (FIG. 14c).

Figure 9:
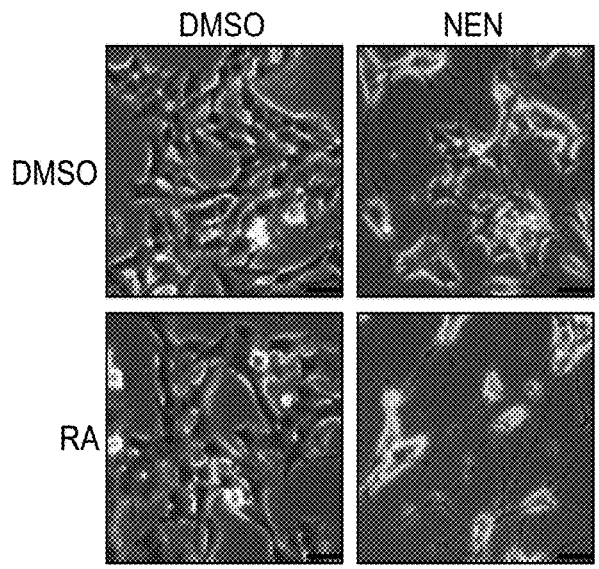
FIG. 9a-FIG. 9f. NEN sensitized neuroblastoma cells to RA-induced differentiation.
Figure 9:
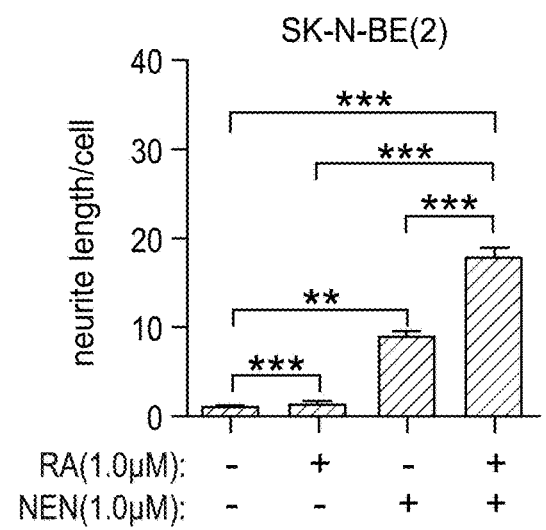
Figure 9:
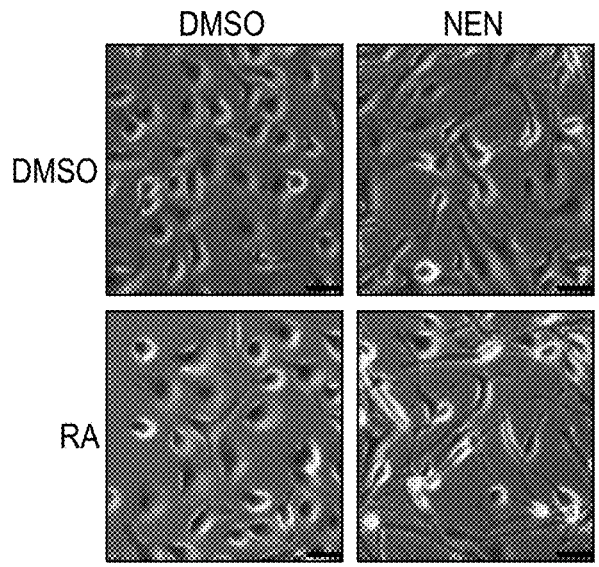
Figure 9:
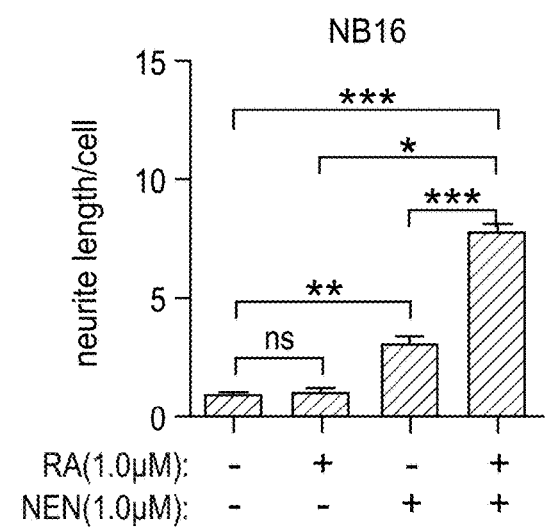
Figure 9:
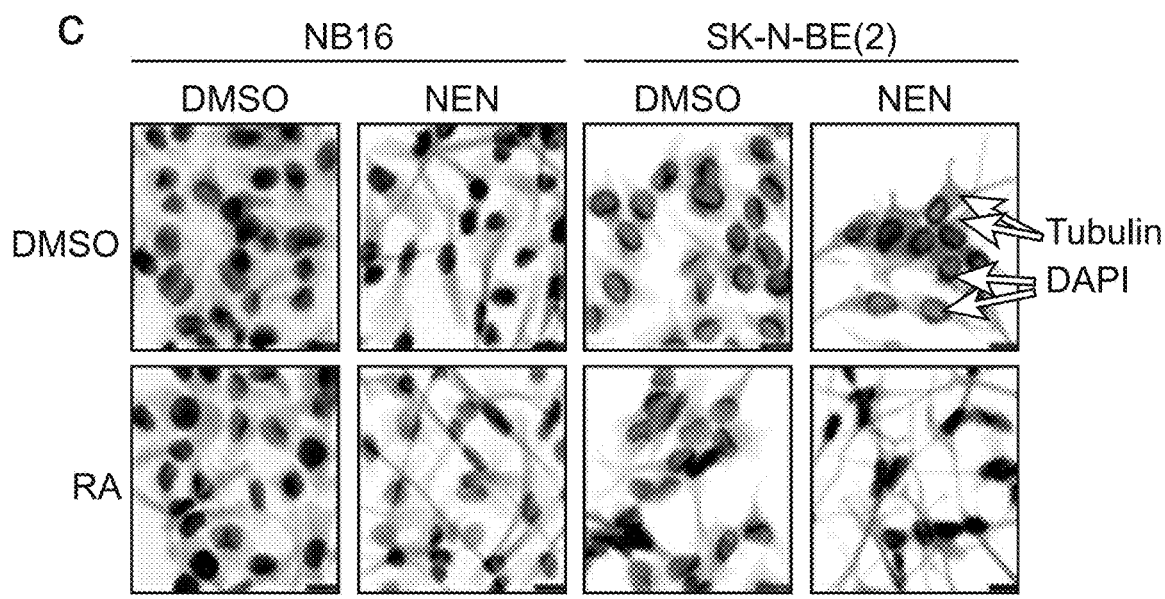
Figure 9:
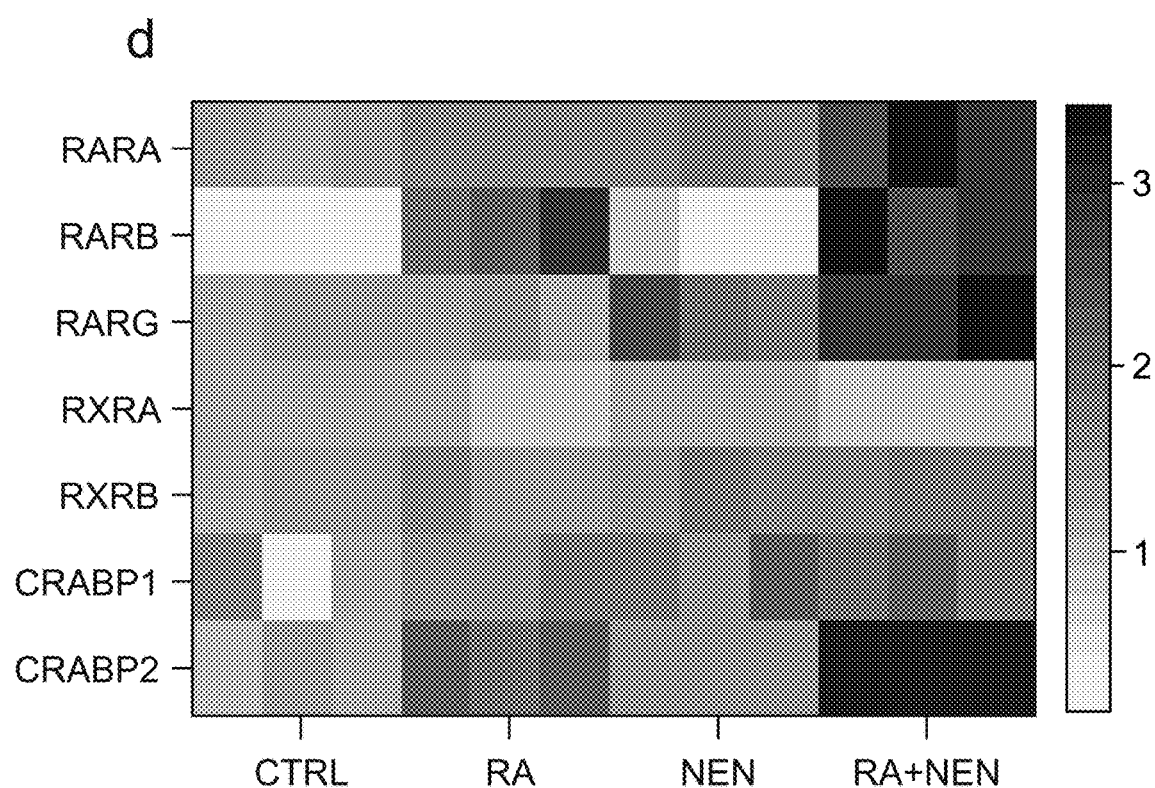
Figure 9:
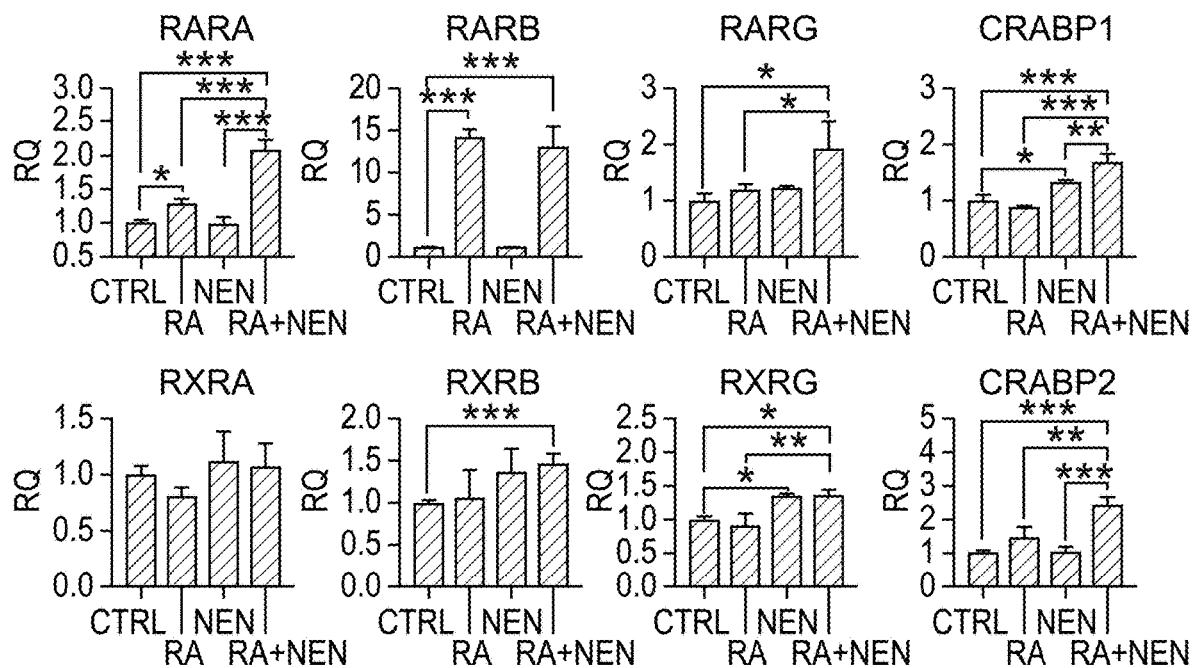
Figure 15:
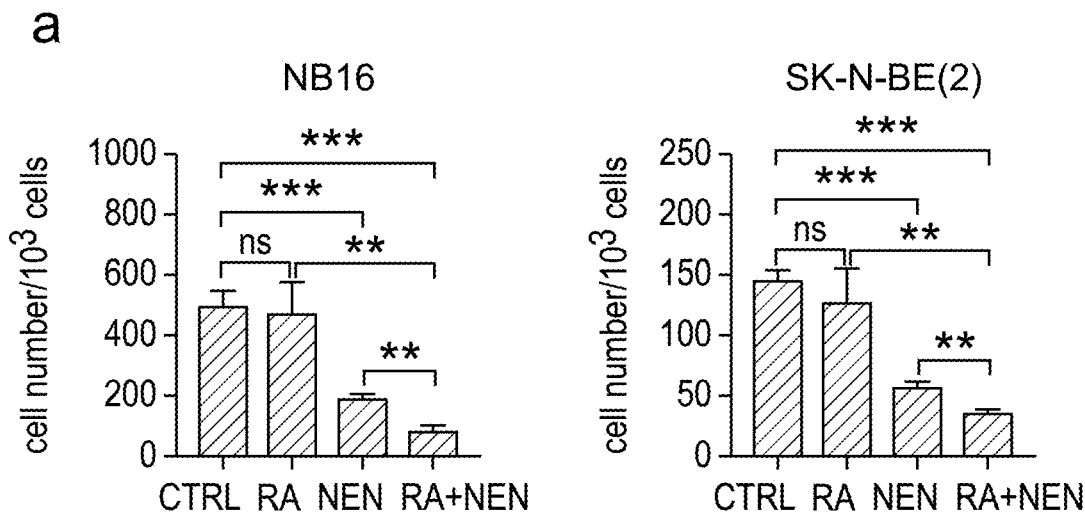
FIG. 15a-FIG. 15f. The synergistic effect of RA and NEN in inducing differentiation.
Figure 15:
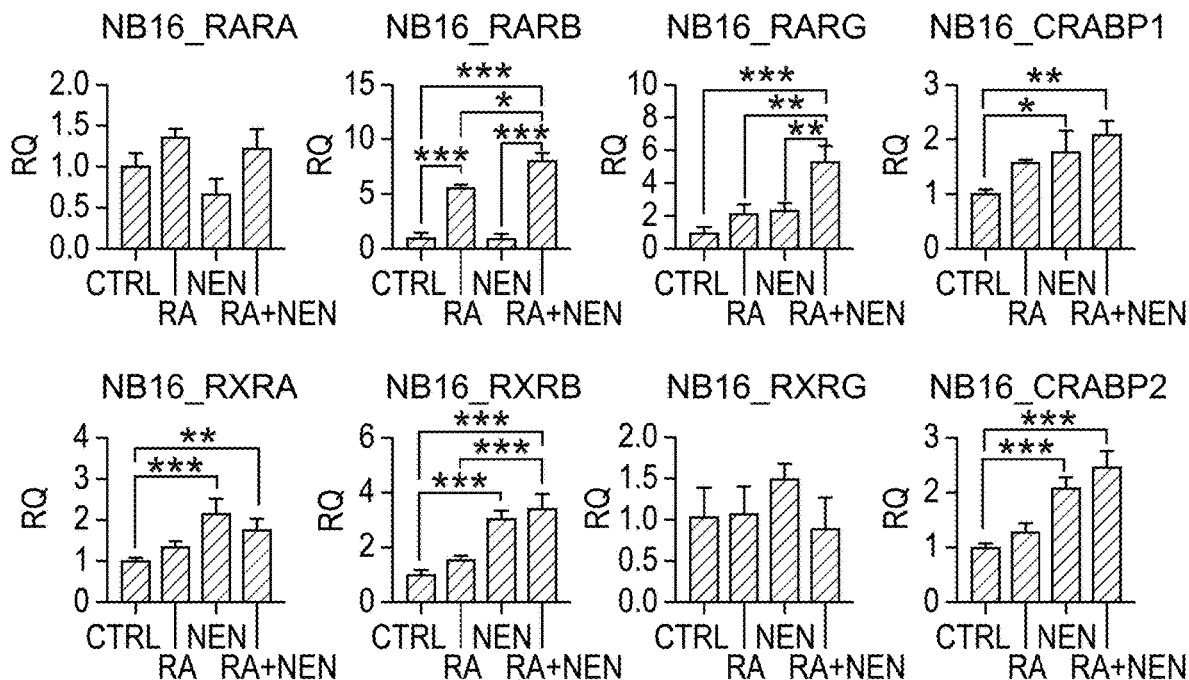
Figure 15:
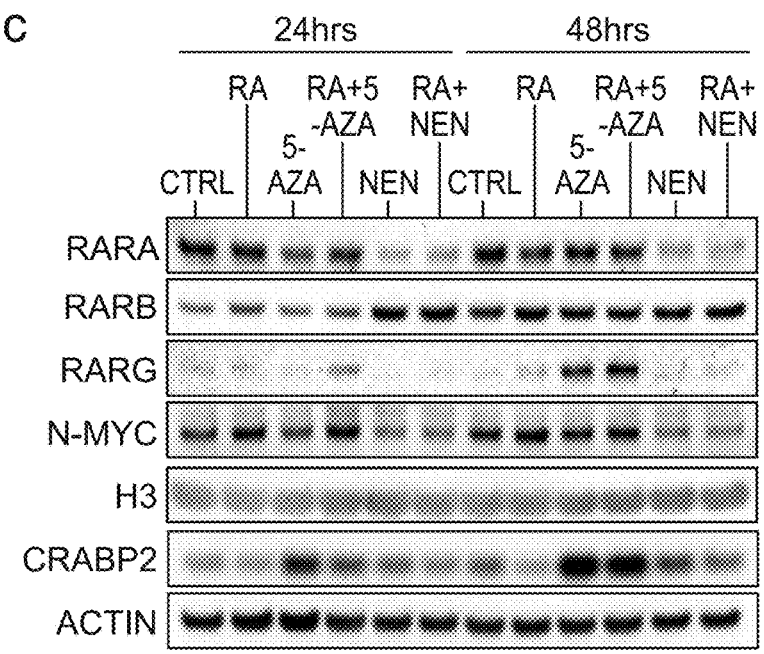
Figure 15:
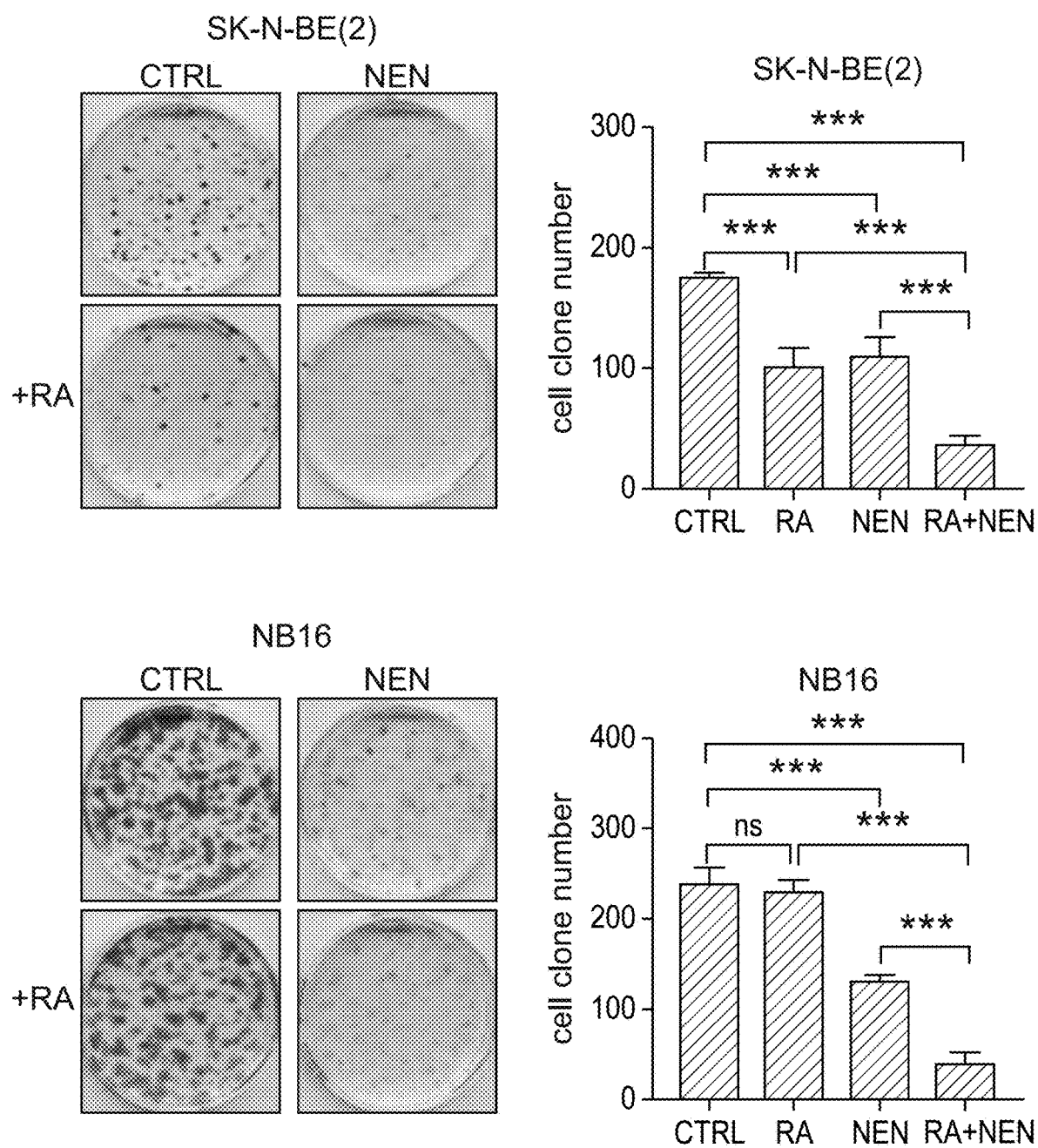
Figure 15:
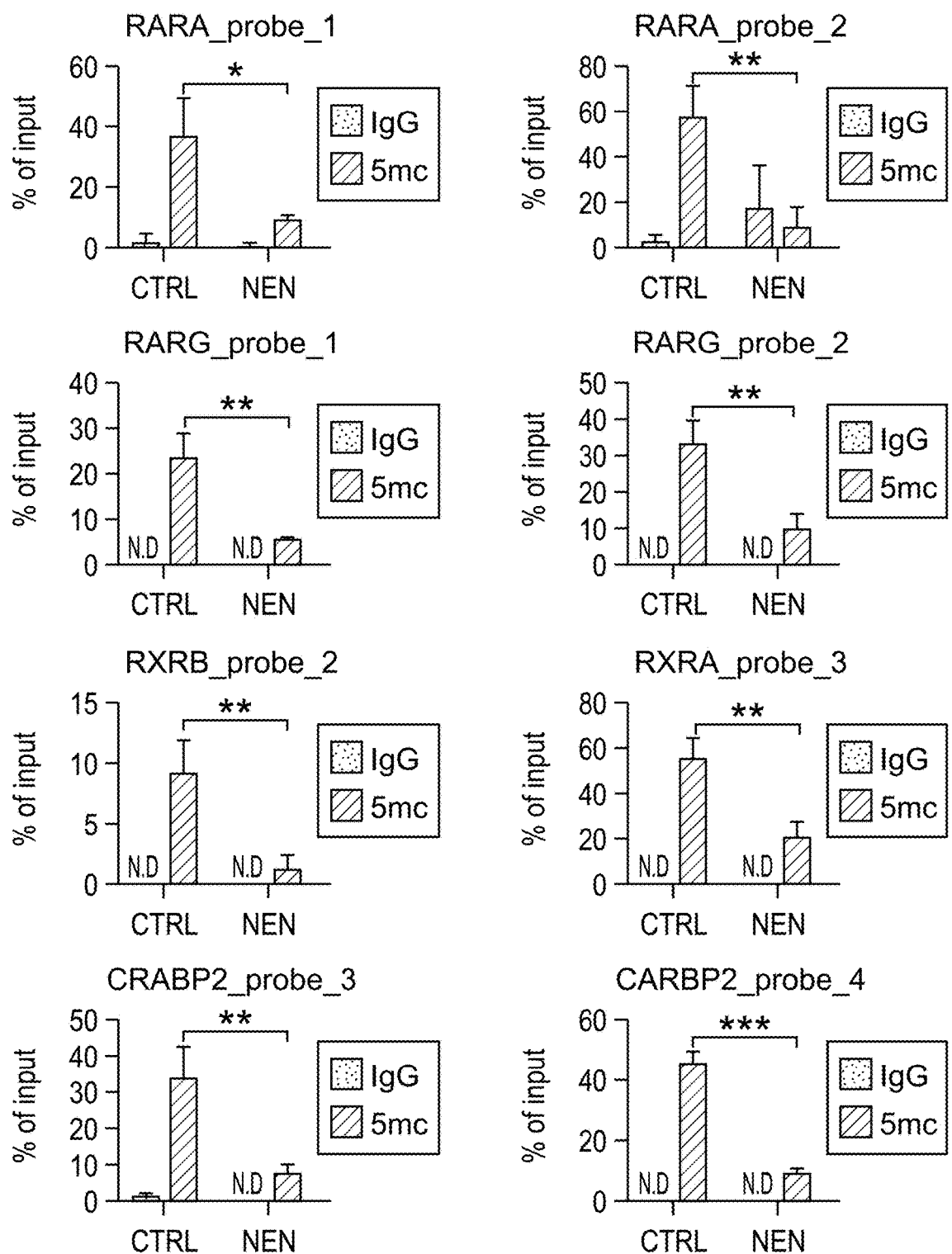
Figure 15:
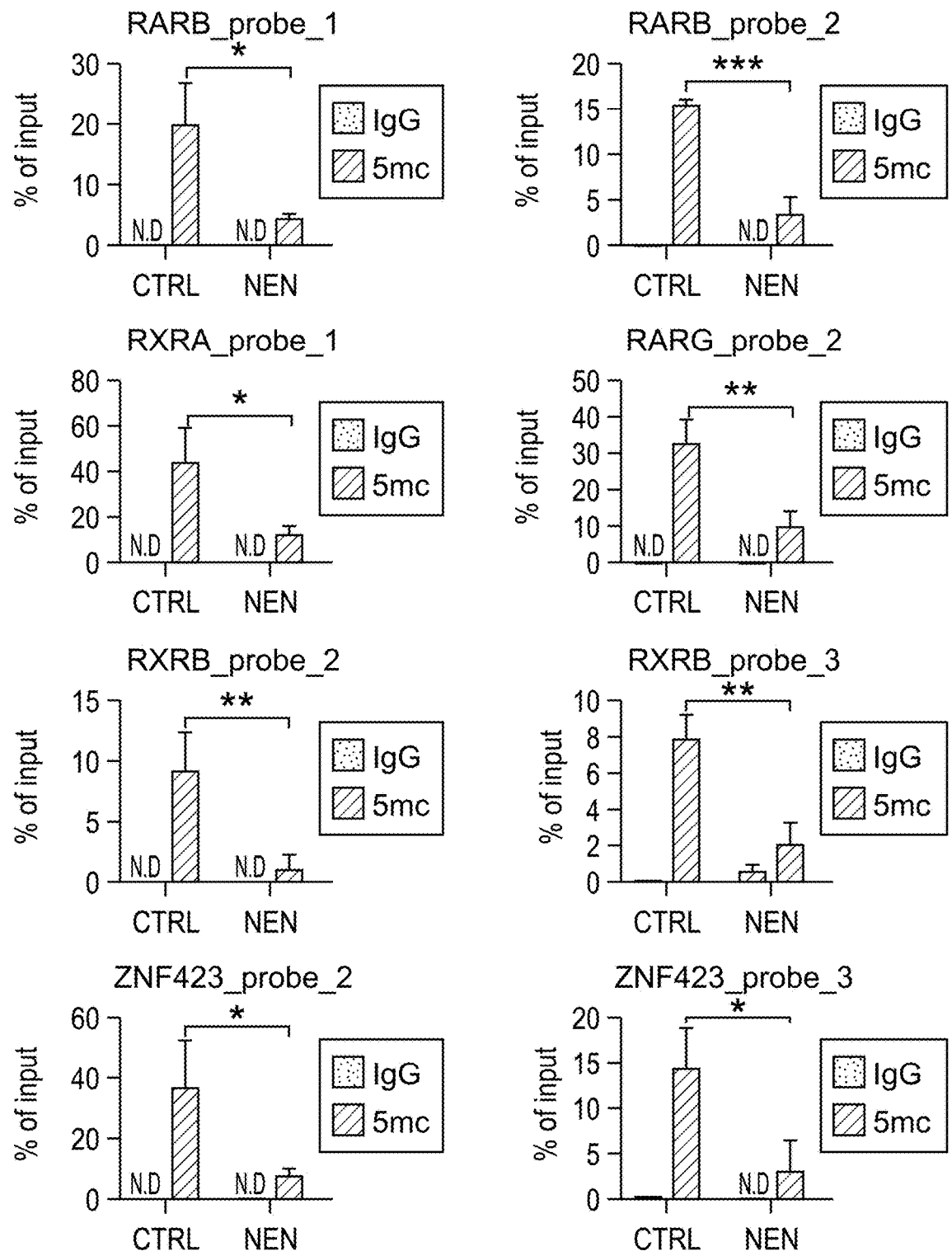
Figure 15:
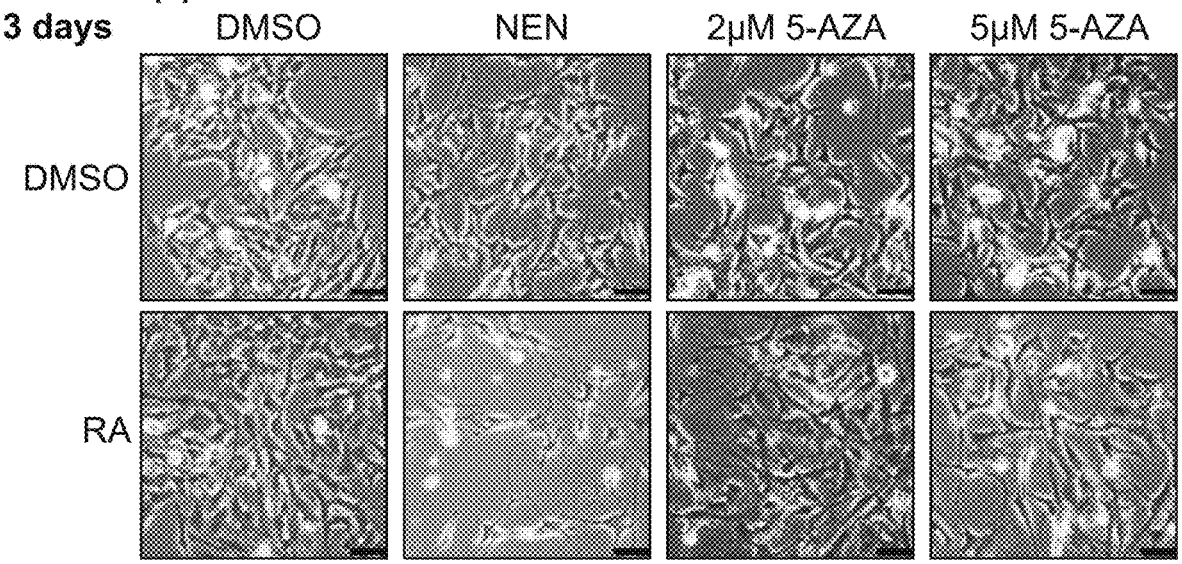
Figure 15:
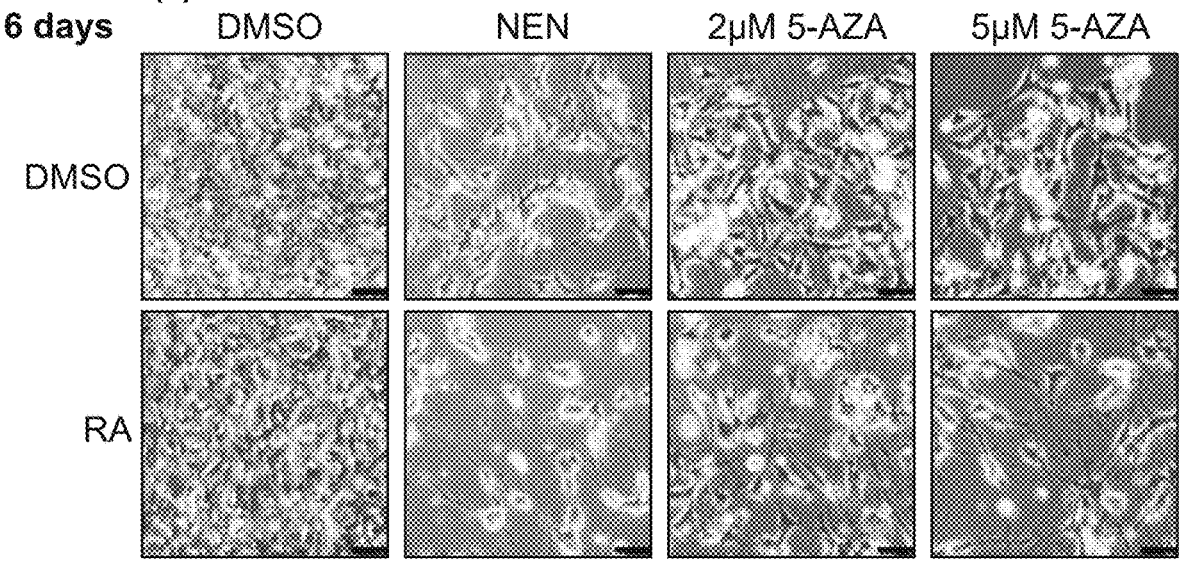

DNMTi treatment induces NB cell differentiation. Particularly, DNMTi treatment promotes RA-induced differentiation in RA-resistant NB cells. Based on these findings, we hypothesize that NEN promotes differentiation in RA-resistant NB cells. We found that NEN alone induced neuron differentiation morphology, and this effect was more profound when combine with RA, judging by the neurite length and immunofluorescence staining against neuron specific β-tubulin III (FIG. 9a, b, c). In addition, NEN treatment enhanced the RA-dependent proliferation arrest effect (FIG. 15a). Furthermore, NEN treatment had a strong synergistic effect with RA on inhibition of clonogenicity (FIG. 15d). Consistent to the observation that NEN restored differentiation morphology when combined with RA, RNA sequencing profiling showed that NEN significantly enhanced the genes expression in RAR signaling induced by RA (FIG. 9d). The gene expression changes were validated using qRT-PCR (FIG. 9e).

In addition, results of methylated DNA Immunoprecipitation (MeDIP)-qRT-PCR assay demonstrated that NEN treatment reduced the methylation on promoter region of genes in RAR signaling (FIG. 15e). Also, NEN treatment alone increased the protein level of RARγ, which was further upregulated when combine with RA in SK-N-BE(2) cells (FIG. 9f). As a DNMTi, 5-Aza also enhanced the RA-induced expressions of RARγ and CRABP2 (FIG. 9f) and induced differentiation with RA (FIG. 15f), which indicating the restoration of RA signaling by NEN depend on DNA demethylation.

Since Otto H. Warburg discovered that tumor cells have a high glucose consumption rate and produce large amounts of lactate in 1920s, oncologists have been interested in how tumor cells alters metabolic pathways to obtain advantages during cancer progression. In one of Warburg's milestone reviews, he proposed that the cause of the Warburg effect was injury of respiration and as a consequence, cell dedifferentiation. However, the underlying mechanism was unclear due to the field's limited understanding of metabolic control of epigenetics.

Inhibition of respiration is essentially the inhibition of the ETC, whose function is to oxidizes cellular NADH to $NAD^+$. ETC inhibition leads to reduction of $NAD^+$/NADH ratio. Low $NAD^+$/NADH ratio not only drives lactate production from pyruvate to enhance the Warburg effect, but also disrupts TCA cycle flux, promoting reduction of α-KG to form L-2-HG. Similar to the D-2-HG produced from tumors carrying IDH1/2 mutation, L-2-HG also inhibits α-KG-dependent deoxygenases, including TET enzymes and JMJDs, leading to DNA and histone hypermethylation. It was shown that this hypermethylation phenotype blocks cell differentiation, promoting tumor progression.

Here we demonstrated that treatment using a mitochondrial uncoupler NEN effectively increased cellular α-KG levels in neuroblastoma cells to promote differentiation. NEN treatment increased $NAD^+$/NADH ratio, which not only drives accelerated glutaminolysis to upregulate α-KG, but also blocks the conversion of α-KG to 2-HG. Together these data indicate that ETC activity is essential to cell differentiation. Surprisingly, even under hypoxia, NEN treatment is still effective in restoring α-KG and reducing 2-HG levels, suggesting that NEN supplementation has an advantage in demethylation in vivo over α-KG supplementation.

N-myc is the major oncogene amplified in NB. High N-myc expression is one key prognosis marker indicating poor survival in neuroblastoma patients. N-myc is down-regulated upon induction of differentiation in neuroblastoma cells, suggesting a negative correlation between N-myc amplification and NB cell differentiation. Here we shown that mitochondrial uncoupler treatment can diminish the 'undruggable' N-Myc expression, highlighting the therapeutic potential in high grade neuroblastoma patients.

ETC inhibition not only promotes 2-HG production to reprogram the epigenome, but also induces reductive carboxylation flux. The citrate generated from α-KG provide acetyl-CoA for lipid synthesis, which is important for cell proliferation. Our data demonstrated not only that NEN treatment reversed this process, but it also increased cellular α-KG levels, suggesting that in addition to promoting proliferation by helping lipid synthesis, another important consequence of reductive carboxylation is to decrease intracellular α-KG levels and induce DNA hypermethylation.

In addition to αKG upregulation, mitochondrial uncoupler treatment caused global metabolic reprograming, including increasing $NAD^+$/NADH ratio, AMP/ATP ratio, etc. These metabolic changes may further alter other signaling pathways that depends on $NAD^+$ or ATP to remodel epigenetics and change cell fate.

In summary, we have shown that NEN, a single agent, has extensive anti-tumor effects both in vitro and in vivo, by its ability to activate ETC. Upon ETC inhibition, altered metabolism causes global changes to epigenetic modification and signaling pathway rather than affecting a single gene or pathway. Thus, activating ETC with mitochondrial uncouplers is an effective way of reversing this process and restoring the global metabolome and epigenome, which ultimately redirects the tumor cell into a differentiated state.

Materials and Methods

Cell lines and culture. CHP134, SK-N-BE(2) and NB16 cells were obtained from Dr. John M. Maris' laboratory (Children's Hospital of Philadelphia). SMS-KCNR cells were obtained from Dr. C. Patrick Reynolds' laboratory (Texas Tech University Health Sciences Center). Certificate of analysis is available from each group. Ovarian cancer cell line OVCAR3 was from Dr. Erinn Rankin's laboratory (Stanford University), and lung cancer cell lines H29 and H82 was from Dr. Julien Sage's laboratory (Stanford University). All cell lines were cultured in DMEM/F12 medium (Caisson Labs, DFL15) supplemented with 1% Penicillin-Streptomycin (Gibco, 15140122), 10% FBS (Sigma, F0926) and extra 1 mM glutamine (Gibco, 25030081).

Protein extraction and immunoblot. Cells were washed with ice-cold PBS buffer (Invitrogen, 20012050) and lysed with harvest buffer (10 mM Hepes pH 7.9, 50 mM NaCl, 500 mM sucrose, 0.1 mM EDTA and 0.5% Triton X-100) supplemented with 1% Halt inhibitors (Thermo Scientific™, 78443) for 10 minutes. Cell lysate was centrifuged at 3000 rpm for 3 min at 4° C. The supernatant containing cytosolic proteins was transferred to a different tube. The pellet containing nuclear proteins was dissolved with nuclear lysis buffer (10 mM Hepes pH 7.9, 0.5M NaCl, 0.1 mM EDTA, 0.1 mM EGTA and 0.1% NP40) supplemented with 1% Halt inhibitors (Thermo Scientific™, 78443) for 5 minutes at 4° C. Then the solution was sonicated at 4° C. for 6 cycles (1 cycle=30 s sonication and 30 s cooldown with "High" energy intensity) using a Bioruptor® Plus sonication (Diagenode, UCD-300). After sonication, the solution was centrifuged at 15,000 rpm for 10 minutes. The supernatant was kept as nuclear extraction. Protein concentration was determined by BCA assay (Thermo Scientific, 23227). 5 µg nuclear proteins or 7.5 µg cytosolic proteins were boiled in loading buffer with reducing reagents (Invitrogen, NuPAGE™ LDS Sample Buffer (4X), NP0007), then separated with SDS-PAGE (Nupage™ 4-12% Bis-Tris Protein Gels, 1.0 mm, Invitrogen™, NP0322BOX). Protein was transferred onto a nitrocellulose membrane (Thermo Scientific™, 88018). After blocking in 5% non-fat milk for 30 minutes at room temperature (RT), the primary antibody was added for incubation overnight at 4° C. After washing with TBST (CST, #9997, 1:10 diluted by deionized water) for 3 times, HRP-conjugated secondary antibodies were applied. Signals were detected with an ECL kit (Thermo Scientific™, 34577) by using BioRad Universal Hood II.

RNA isolation, reverse transcription, and real-time PCR. The procedure was performed as described before. Briefly, total RNA was isolated from 60 mm tissue culture plates according to the TRIzol Reagent (Invitrogen, 15596026) protocol. 3 µg of total RNA was used in the reverse transcription reaction using the iScript cDNA synthesis kit (Bio-Rad). Quantitative PCR amplification was performed on the Prism 7900 Sequence Detection System (Applied Biosystems) using Taqman Gene Expression Assays (Applied Biosystems). Gene expression level were normalized to 18S rRNA.

Cell proliferation and clonogenic assay. $2 \times 10^4$ cells were seeded in 12 well-plate and allowed to attached overnight. Then the cells were treated with various conditions as indicated for 48 h or 96 h (n=3). After treatment, cells were counted using hemocytometer.

For the clonogenic assay, 500 cells were plated in 60 mm dishes. After 24 h, cells were treated with indicated conditions. After 14 days, the cells were fixed by 50% methanol in PBS for 15 minutes and stained by crystal violet staining solution (0.5% crystal violet and 25% methanol in PBS). The quantification was done by using countPHICS.

Neurite outgrowth assay. The quantification of neurite was performed as described before. Shortly, $1 \times 10^4$ SK-N-BE(2) and NB16 cells were plated in a 12 well-plate per well. After overnight incubation, cells were treated with various conditions as indicated for 72 h. Then, images were taken by a Leica Florescent Microscope DMi8 in phase contrast mode (20× magnification). The lengths of the neurites were traced and quantified using the ImageJ plugin NeuronJ. For each sample, total neurite length was measured and normalized to the number of cell bodies, mean value from 3 biological replicates was reported.

Immunofluorescence staining. SK-N-BE(2) and NB16 cells were seeded into 8-chamber slides (Thermo Fisher Scientific, 154534) with a density of $6 \times 10^3$ cells/well overnight and treated with indicated treatment for 72 h. Cells were fixed with 4% PFA in PBS with 0.1% Tween-20 at RT for 30 minutes followed by permeabilization with 0.1% Triton X-100 in PBS at room temperature for 10 min. The cells were washed with PBS twice and blocked with 2.5% horse serum in PBS at RT for 1 h. Then, cells were subjected to immunofluorescence staining with primary antibody at 4° C. overnight. After two washes with PBS, cells were incubated with Alexa Fluor 594-conjugated anti-rabbit secondary antibody (Life Technologies) at RT for 1 h followed by staining with DAPI (Vector Laboratories, H-1800-2). Images were acquired with Leica DMi8 microscope.

DNA microarray analysis. DNA extraction was carried out with samples were extracted by using PureLink™ Genomic DNA Mini Kit (Gibco, K182001), according to the protocol provided by the supplier. The DNA was quantified with the Nanodrop and 3 ug was used for bisulfite modification using the EZ DNA methylation kit (D5001, Zymo Research, Orange, CA) according to the protocol provided with the modification step according to the recommendations for array processing of the samples. Control PCR reactions were carried out before array analysis to confirm successful modification of the DNA. The bisulfite-modified DNA (500 ng) was applied to the Infinium MethylationEPIC array (Illumina). After bisulfite treatment of the DNA samples, the cytosines in the CpG sites were genotyped as C/T polymorphisms according to the manufacturer's protocol. Raw array data was collected with 866 k probes for 8 samples across 4 stages (those are control, 5 hours, 24 hours and 48 hours). The fluorescence signals were measured from the BeadArrays using an Illumina BeadStation GX scanner.

The fluorescence data were then analyzed using the GenomeStudio software (Illumina). The software assigns a score called a "b value" to each CpG site, which corresponds to the ratio between the fluorescence signal of the methylated allele (C) and the sum of the fluorescent signals of the methylated (C) and unmethylated (T) alleles. The data generated by the BeadStudio software was exported and further analyses were performed in the R programming environment. Then a detection p-value for every probe in every sample, representing the quality of the signal is generated using method minfi. Poor probes with all samples' p-values larger than or equal to 0.01 are removed which results in 864 k probes left. For methylation levels estimations we use M-Values (log 2 based Methylation signal over unmethylation signal) for analysis.

Differential Methylation Probes are identified by first standardizing M-Values with both rows and columns and then enforced certain direction (hypermethylated or hypomethylated) between control versus treatments. The p-values used in the volcano plot is calculated through Fisher' method by combining quality p-value for all samples with each probe.

Methylated DNA Immunoprecipitation. $5 \times 10^5$ SK-N-BE (2) cells were plated in 60 mm dishes. After overnight incubation, the cells were treated by DMSO or 1 µM NEN for 5 h. After treatment, the cells were collected for DNA extraction as described above. 10 µg genomic DNA was sheared using a Bioruptor® Plus sonicator (Diagenode, UCD-300) to 550 bp fragments according to the instrument manual. Agarose electrophoresis was employed to examine the sizes of DNA fragments. The sonicated DNA samples were denatured at 95° C. for 15 minutes, then kept on ice immediately for at least 5 minutes. 200 ng denatured DNA was transferred to a new tube for input control and diluted with EDTA-free TE buffer to 100 µl total volume. For each pulldown reaction, transfer 600 ng of denatured DNA solution to new tubes and add EDTA-free TE buffer to 300 µl total volume. Add 2 µl antibody (5-mc or IgG control) and 20 µl prewashed Dynabeads™ Protein A (Invitrogen™, 10001 D) into the tubes and incubate the samples at 4° C. for 60 minutes with rotation. After incubation, place the tubes in magnetic rack for 30 s to allow the beads separate from solution. Remove the solution carefully without disturbing the beads. Wash the beads for 4 times by IP buffer (0.01% SDS, 1% Triton X-100, 2 mM EDTA, 20 mM Tris-HCl pH 8.1, 150 mM NaCl). DNA was eluted by resuspending the beads in 100 µl of digestion buffer (10 mM Tris pH 8.0, 1 mM EDTA, 1% SDS, 1 µg/µl proteinase K) and incubated for 6 hr at 65° C. Recover the DNA by using QuickClean II PCR Extraction Kit (GenScript, L00419-100). Recovered DNA was used for qPCR analysis. All data were normalized to input.

RNA Sequencing and bioinformatics analysis. The total RNA from treatment groups (Ctrl and NEN treated, n=3) were extracted using Trizol reagent according to the manufacturer's instructions. The RNA-seq library was constructed and subjected to 150 bp paired-end sequencing on an Illumina sequencing platform (Novogene). RNA-seq analysis was performed using the kallisto and sleuth analytical pipeline. In brief, a transcript index was generated with reference to Ensembl version 67 for hg19. Paired-end mRNA-seq reads were pseudo-aligned using kallisto (v0.42.4) with respect to this transcript index using 100 bootstraps (-b 100) to estimate the variance of estimated transcript abundances. Transcript-level estimates were aggregated to transcripts per million (TPM) estimates for each gene, with gene names assigned from Ensembl using biomaRt. Differential gene expression analysis was performed using the sleuth R package across pairwise groups using Wald tests, with significant hits called with a sleuth q-value<0.05 and log 2(fold change) >0.693 or <−0.693. Gene set enrichment analysis (GSEA) was used to examine the significantly enriched pathways by comparing the normalized data of the entire RNA seq TPM dataset between groups as indicated to Molecular Signatures Database (MSigDB v7.4). All the annotated transcripts (~21,427 features in total) with expression values were uploaded to a locally-installed GSEA tool (version 4.1.0) and compared against the H: hallmark gene sets (50 gene sets).

To generate the favorable or unfavorable prognosis gene sets, Kaplan-Meier assay were employed for all the genes independently by using all 11 available neuroblastoma patient databases from R2. Each gene that passed the filter of Kaplan-Meier assay showed significant correlation with prognosis (p-value<0.05) in relevant databases.

For functional annotation, differentially expressed genes were submitted to online Database for Annotation, Visualization and Integrated Discovery (DAVID) website. The Analyses in DAVID were performed using the default parameters.

Global DNA methylation analysis. The protocol is adapted from previous publication. $3 \times 10^5$ cells were plated in 60 mm dishes, after overnight incubation, the cells were treated with DMSO, 1 µM NEN or 5-Azacytidine for indicated time. Cells were scaped in ice-cold PBS, the cell pellet were collected by centrifuging at 3000 rpm for 3 minutes. DNA samples were extracted by using PureLink™ Genomic DNA Mini Kit (Gibco, K182001), then, they were denatured at 95° C. for 10 minutes and placed on ice immediately for at least 5 minutes. 8 µg DNA in 54 µl of nuclease-free water were digested by adding 2 µl nuclease P1 (1 U/µl, Wako USA) in 10 mM $NH_4OAc$ pH 5.3 (adding ⅜ µl 100 mM $NH_4OAc$) at 42° C. overnight. It was followed by addition of 6.8 µl $NH_4HCO_3$ (1 M) and 2 µl of phosphodiesterase I from *Crotalus adamanteus* venom (0.001 U, Sigma-Aldrich) at 37° C. for 2 hr and finally by addition of 2 U of alkaline phosphatase from *E. coli* (Sigma-Aldrich) at 37° C. for 2 hr. Digested DNA was diluted two fold with nuclease-free $H_2O$. Digested DNA was diluted two-fold with nuclease-free water. 10 µl diluted solution solution injection to liquid chromatography was performed using a 1290 Infinity LC system (Agilent, Santa Clara, US) coupled to a 6470B Triple quadrupole (Agilent, Santa Clara, US). C18 100×2.1 mm column (Agilent) was used for compound separation a flow rate of 0.3 ml/min. The mobile phase A consisted of 10 mM Ammonium Formate 0.1% formic acid in water and the mobile phase B was 10 mM Ammonium Formate 0.1% formic acid in water:Acetonitrile (1:9). The gradient elution was 0-2 min, 2% B; 2-4 min, 2% B→20% B; 4-4.5 min, 20% B→80% B; 4.5-6 min, 80% B→95% B; 6-6.2 min, 95% B→2% B; 6.2-8 min, 2% B. The overall runtime was 8 min, and the injection volume was 10 µl. Agilent 6470B Triple quadrupole was operated in positive mode and the relevant parameters were as follows: Capillary voltage, 3000 V; nozzle voltage, 1000 V; fragmentor voltage, 125 V; drying gas flow, 12 L/min; capillary temperature, 325° C., drying gas temperature, 350° C.; and nebulizer pressure, 40 psi. The acquisition rate was 1. 64 cycle/s. Nucleosides were quantified using the nucleoside precursor ion to base ion mass transitions of 242.12 to 126.1 for 5m-dc and 228.1 to 117 for dc. Quantification of the ratio 5m-dc/dc was performed using the calibration curves obtained from nucleoside standards running at the same time.

Metabolic analysis. For the metabolomics and isotope tracing analysis in vitro, cells were washed with cold PBS, lysed in 80% Ultra LC-MS acetonitrile on ice for 15 minutes, centrifuged at 20,000 g for 10 minutes at 4° C., and supernatant was subjected to mass spectrometry analysis. For the metabolomics analysis in vivo, 10-20 mg tissue were cut off on ice, rinsed if necessary to remove blood, and place in a 2 ml round-bottom cryovial. The tissues were homogenized by 3 times 10 s on/off bursts homogenization in 1 ml 80% methanol on dry ice. Transfer the homogenate to an Eppendorf tube and keep on liquid nitrogen while processing the remaining samples. Incubated all the samples in −80° C. for 30 minutes. After incubation, vortexed the samples for 5 seconds. Then centrifuged the samples at 20,000 g for 10 minutes at 4° C., and supernatant was subjected to mass spectrometry analysis. Resuspend the remaining cellular pellet in 100 ul protein lysis buffer and determine the protein concentration. Then calculate the total protein content per sample.

Liquid chromatography was performed using an Agilent 1290 Infinity LC system (Agilent, Santa Clara, US) coupled to a Q-TOF 6545 mass spectrometer (Agilent, Santa Clara, US). A hydrophilic interaction chromatography method (HILIC) with a BEH amide column (100×2.1 mm i.d., 1.7 µm; Waters) was used for compound separation at 35° C. with a flow rate of 0.3 ml/minutes. The mobile phase A consisted of 25 mM ammonium acetate and 25 mM ammonium hydroxide in water and mobile phase B was acetonitrile. The gradient elution was 0-1 minute, 85% B; 1-12 minutes, 85% B→65% B; 12-12.2 minutes, 65% B→40% B; 12.2-15 minutes, 40% B. After the gradient, the column was re-equilibrated at 85% B for 5 minutes. The overall runtime was 20 minutes, and the injection volume was 5 µL. Agilent Q-TOF was operated in negative mode and the relevant parameters were as listed: ion spray voltage, 3500 V; nozzle voltage, 1000 V; fragmentor voltage, 125 V; drying gas flow, 11 L/minutes; capillary temperature, 325° C., drying gas temperature, 350° C.; and nebulizer pressure, 40 psi. A full scan range was set at 50 to 1600 (m/z). The reference mass was 119.0363 and 980.0164. The acquisition rate was 2 spectra/s. Targeted analysis, isotopologues extraction and natural isotope abundance correction were performed by Agilent Profinder B.10.00 (Agilent Technologies).

Stable isotope tracing analysis. For glutamine isotope tracing under normoxia, SK-N-BE(2) and NB16 cells were pretreated with DMSO or 1 µM NEN for 3 h. Then the culture medium was changed to DMEM/F-12, no glutamine (Gibco, 21331020) with 4 mM U-$^{13}C_5$-glutamine (Cambridge Isotope Laboratories, CLM-1822-H) and 10% dialyzed FBS (Gibco, 26400044) under same treatment condition as above for 2 h. For glutamine isotope tracing under hypoxia, the SK-N-BE(2) cells were pretreated by DMSO or 1 µM NEN under normoxia or hypoxia for 4 h. Then changed the medium to DMEM/F-12, no glutamine (Gibco, 21331020) with 4 mM 1-$^{13}C$-glutamine (Cambridge Isotope Laboratories, CLM-CLM-3612-PK) and 10% dialyzed FBS (Gibco, 26400044) for 2 h with same treatment under normoxia or hypoxia for 2 h.

Mouse orthotopic neuroblastoma model. All mouse procedures were performed in accordance with Stanford University recommendations for the care and use of animals and were maintained and handled under protocols approved by the Institutional Animal Care and Use Committee. All procedures were performed with female NC nude mice (Taconic, Hudson, NY, USA) at 7 weeks of age. Procedures and ultrasound measurements (see below) were performed under general anesthesia using isoflurane inhalation. Orthotopic tumors within the adrenal gland were created as described before 16. Briefly, a transverse incision was made on the left flank to locate the left adrenal gland, and 2 mL of phosphate buffered saline (PBS) containing 104 SK-N-BE(2) cells were injected into the adrenal gland using a 30 G needle. Fascia and skin were closed in separate layers. Tumor formation was monitored by non-invasive ultrasound measurements, and the animals euthanized when the tumor volume exceeded 1,000 mm$^3$.

Monitoring tumor growth with high frequency ultrasound. After securing the mouse in a prone position, a Visual Sonics Vevo 2100 sonographic probe (Toronto, Ontario, Canada) was applied to the left flank to locate the left adrenal gland and the tumor. Serial cross-sectional images (0.076 mm between images) were taken. The tumor volume was measured using the 3-D reconstruction tool (Vevo Software v1.6.0, Toronto, Ontario, Canada).

Histological and Immunohistochemical examination of mouse orthotopic tumors. H&E and immunohistochemically stained sections were prepared from formalin-fixed and paraffin-embedded blocks of the mouse orthotopic tumors. As for immunostaining, unstained sections were heated for 30 minutes in Bond™ Epitope Retrieval Solution 2 (No. AR9640; Leica Biosystems Newcastle LTD, Benton Ln, Newcastle Upon Tyne, UK), and incubated with anti-human N-Myc rabbit monoclonal antibody (#51705, Cell Signaling Technology, Inc., MA, USA at a dilution of 1:300). The counter staining with hematoxylin was performed.

Statistics. For cell proliferation and MS experiments, three biological repeats were used for data analysis. Results were represented as mean±SEM or mean±SD. The student's t-test was performed to determine the significance between groups (two-tailed, unequal variance).

REFERENCES

Jones, P. A.; Issa, J. P.; Baylin, S., Targeting the cancer epigenome for therapy. *Nat Rev Genet* 2016, 17(10), 630-41.

Kinnaird, A.; Zhao, S.; Wellen, K. E.; Michelakis, E. D., Metabolic control of epigenetics in cancer. *Nat Rev Cancer* 2016, 16 (11), 694-707.

Reynolds, C.; Biedler, J.; Spengler, B.; Reynolds, D.; Ross, R.; Frenkel, E.; Smith, R., Characterization of human neuroblastoma cell lines established before and after therapy. *Journal of the National Cancer Institute* 1986, 76 (3), 375-387.

Li, A. M.; Ducker, G. S.; Li, Y.; Seoane, J. A.; Xiao, Y.; Melemenidis, S.; Zhou, Y.; Liu, L.; Vanharanta, S.; Graves, E. E.; Rankin, E. B.; Curtis, C.; Massague, J.; Rabinowitz, J. D.; Thompson, C. B.; Ye, J., Metabolic Profiling Reveals a Dependency of Human Metastatic Breast Cancer on Mitochondrial Serine and One-Carbon Unit Metabolism. *Mol Cancer Res* 2020, 18 (4), 599-611.

Brzozowska, B.; Gałecki, M.; Tartas, A.; Ginter, J.; Kaźmierczak, U.; Lundholm, L., Freeware tool for analysing numbers and sizes of cell colonies. *Radiation and Environmental Biophysics* 2019, 58 (1), 109-117.

Li, Y.; Gruber, J. J.; Litzenburger, U. M.; Zhou, Y.; Miao, Y. R.; LaGory, E. L.; Li, A. M.; Hu, Z.; Yip, M.; Hart, L. S.; Maris, J. M.; Chang, H. Y.; Giaccia, A. J.; Ye, J., Acetate supplementation restores chromatin accessibility and promotes tumor cell differentiation under hypoxia. *Cell Death Dis* 2020, 11 (2), 102.

Meijering, E.; Jacob, M.; Sarria, J. C.; Steiner, P.; Hirling, H.; Unser, M., Design and validation of a tool for neurite tracing and analysis in fluorescence microscopy images. *Cytometry Part A: the journal of the International Society for Analytical Cytology* 2004, 58 (2), 167-176.

Aryee, M. J.; Jaffe, A. E.; Corrada-Bravo, H.; Ladd-Acosta, C.; Feinberg, A. P.; Hansen, K. D.; Irizarry, R. A., Minfi: a flexible and comprehensive Bioconductor package for the analysis of Infinium DNA methylation microarrays. *Bioinformatics* 2014, 30 (10), 1363-9.

Bray, N. L.; Pimentel, H.; Melsted, P.; Pachter, L., Near-optimal probabilistic RNA-seq quantification. *Nature biotechnology* 2016, 34 (5), 525-527.

Pimentel, H.; Bray, N. L.; Puente, S.; Melsted, P.; Pachter, L., Differential analysis of RNA-seq incorporating quantification uncertainty. *Nature methods* 2017, 14 (7), 687.

Mootha, V. K.; Lindgren, C. M.; Eriksson, K.-F.; Subramanian, A.; Sihag, S.; Lehar, J.; Puigserver, P.; Carlsson, E.; Ridderstråle, M.; Laurila, E., PGC-1α-responsive genes involved in oxidative phosphorylation are coordinately downregulated in human diabetes. *Nature genetics* 2003, 34 (3), 267-273.

Subramanian, A.; Tamayo, P.; Mootha, V. K.; Mukherjee, S.; Ebert, B. L.; Gillette, M. A.; Paulovich, A.; Pomeroy, S. L.; Golub, T. R.; Lander, E. S., Gene set enrichment analysis: a knowledge-based approach for interpreting genome-wide expression profiles. *Proceedings of the National Academy of Sciences* 2005, 102 (43), 15545-15550.

Huang, D. W.; Sherman, B. T.; Lempicki, R. A., Bioinformatics enrichment tools: paths toward the comprehensive functional analysis of large gene lists. *Nucleic acids research* 2009, 37(1), 1-13.

Sherman, B. T.; Lempicki, R. A., Systematic and integrative analysis of large gene lists using DAVID bioinformatics resources. *Nature protocols* 2009, 4 (1), 44.

Greer, E. L.; Blanco, M. A.; Gu, L.; Sendinc, E.; Liu, J.; Aristizabal-Corrales, D.; Hsu, C. H.; Aravind, L.; He, C.; Shi, Y., DNA Methylation on N6-Adenine in *C. elegans*. *Cell* 2015, 161 (4), 868-78.

Chiu, B.; Coburn, J.; Pilichowska, M.; Holcroft, C.; Seib, F. P.; Charest, A.; Kaplan, D. L., Surgery combined with controlled-release doxorubicin silk films as a treatment strategy in an orthotopic neuroblastoma mouse model. *Br J Cancer* 2014, 111 (4), 708-15.

Takeshima, H.; Ushijima, T., Accumulation of genetic and epigenetic alterations in normal cells and cancer risk. *NPJ Precis Oncol* 2019, 3, 7.

You, J. S.; Jones, P. A., Cancer genetics and epigenetics: two sides of the same coin? *Cancer Cell* 2012, 22 (1), 9-20.

Ehrlich, M., DNA hypermethylation in disease: mechanisms and clinical relevance. *Epigenetics* 2019, 14 (12), 1141-1163.

Henrich, K. O.; Bender, S.; Saadati, M.; Dreidax, D.; Gartlgruber, M.; Shao, C.; Herrmann, C.; Wiesenfarth, M.; Parzonka, M.; Wehrmann, L.; Fischer, M.; Duffy, D. J.; Bell, E.; Torkov, A.; Schmezer, P.; Plass, C.; Hofer, T.; Benner, A.; Pfister, S. M.; Westermann, F., Integrative Genome-Scale Analysis Identifies Epigenetic Mechanisms of Transcriptional Deregulation in Unfavorable Neuroblastomas. *Cancer Res* 2016, 76 (18), 5523-37.

Koch, A.; Joosten, S. C.; Feng, Z.; de Ruijter, T. C.; Draht, M. X.; Melotte, V.; Smits, K. M.; Veeck, J.; Herman, J. G.; Van Neste, L.; Van Criekinge, W.; De Meyer, T.; van Engeland, M., Analysis of DNA methylation in cancer: location revisited. *Nat Rev Clin Oncol* 2018, 15 (7), 459-466.

Weisenberger, D. J.; Liang, G.; Lenz, H. J., DNA methylation aberrancies delineate clinically distinct subsets of colorectal cancer and provide novel targets for epigenetic therapies. *Oncogene* 2018, 37 (5), 566-577.

Bennett, R. L.; Licht, J. D., Targeting Epigenetics in Cancer. *Annu Rev Pharmacol Toxicol* 2018, 58, 187-207.

Derissen, E. J.; Beijnen, J. H.; Schellens, J. H., Concise drug review: azacitidine and decitabine. *The oncologist* 2013, 18 (5), 619.

Jones, P. A.; Issa, J.-P. J.; Baylin, S., Targeting the cancer epigenome for therapy. *Nature Reviews Genetics* 2016, 17 (10), 630.

Linnekamp, J.; Butter, R.; Spijker, R.; Medema, J.; Van Laarhoven, H., Clinical and biological effects of demethylating agents on solid tumours—a systematic review. *Cancer Treatment Reviews* 2017, 54, 10-23.

Wu, X.; Zhang, Y., TET-mediated active DNA demethylation: mechanism, function and beyond. *Nature Reviews Genetics* 2017, 18 (9), 517.

Carey, B. W.; Finley, L. W.; Cross, J. R.; Allis, C. D.; Thompson, C. B., Intracellular alpha-ketoglutarate maintains the pluripotency of embryonic stem cells. *Nature* 2015, 518 (7539), 413-6.

Intlekofer, A. M.; Dematteo, R. G.; Venneti, S.; Finley, L. W.; Lu, C.; Judkins, A. R.; Rustenburg, A. S.; Grinaway, P. B.; Chodera, J. D.; Cross, J. R.; Thompson, C. B., Hypoxia Induces Production of L-2-Hydroxyglutarate. *Cell Metab* 2015, 22 (2), 304-11.

Oldham, W. M.; Clish, C. B.; Yang, Y.; Loscalzo, J., Hypoxia-Mediated Increases in L-2-hydroxyglutarate Coordinate the Metabolic Response to Reductive Stress. *Cell Metab* 2015, 22 (2), 291-303.

Wise, D. R.; Ward, P. S.; Shay, J. E.; Cross, J. R.; Gruber, J. J.; Sachdeva, U. M.; Platt, J. M.; DeMatteo, R. G.; Simon, M. C.; Thompson, C. B., Hypoxia promotes isocitrate dehydrogenase-dependent carboxylation of α-ketoglutarate to citrate to support cell growth and viability. *Proceedings of the National Academy of Sciences* 2011, 108 (49), 19611-19616.

Fendt, S.-M.; Bell, E. L.; Keibler, M. A.; Olenchock, B. A.; Mayers, J. R.; Wasylenko, T. M.; Vokes, N. I.; Guarente, L.; Vander Heiden, M. G.; Stephanopoulos, G., Reductive glutamine metabolism is a function of the α-ketoglutarate to citrate ratio in cells. *Nature communications* 2013, 4 (1), 1-11.

Intlekofer, A. M.; Dematteo, R. G.; Venneti, S.; Finley, L. W.; Lu, C.; Judkins, A. R.; Rustenburg, A. S.; Grinaway, P. B.; Chodera, J. D.; Cross, J. R., Hypoxia induces production of L-2-hydroxyglutarate. *Cell metabolism* 2015, 22 (2), 304-311.

Xu, W.; Yang, H.; Liu, Y.; Yang, Y.; Wang, P.; Kim, S.-H.; Ito, S.; Yang, C.; Wang, P.; Xiao, M.-T., Oncometabolite 2-hydroxyglutarate is a competitive inhibitor of α-ketoglutarate-dependent dioxygenases. *Cancer cell* 2011, 19(1), 17-30.

Tao, H.; Zhang, Y.; Zeng, X.; Shulman, G. I.; Jin, S., Niclosamide ethanolamine-induced mild mitochondrial uncoupling improves diabetic symptoms in mice. *Nature medicine* 2014, 20 (11), 1263.

Alasadi, A.; Chen, M.; Swapna, G.; Tao, H.; Guo, J.; Collantes, J.; Fadhil, N.; Montelione, G. T.; Jin, S., Effect of mitochondrial uncouplers niclosamide ethanolamine (NEN) and oxyclozanide on hepatic metastasis of colon cancer. *Cell death & disease* 2018, 9 (2), 1-14.

Mullen, A. R.; Wheaton, W. W.; Jin, E. S.; Chen, P.-H.; Sullivan, L. B.; Cheng, T.; Yang, Y.; Linehan, W. M.; Chandel, N. S.; DeBerardinis, R. J., Reductive carboxylation supports growth in tumour cells with defective mitochondria. *Nature* 2012, 481 (7381), 385-388.

Alasadi, A.; Chen, M.; Swapna, G. V. T.; Tao, H.; Guo, J.; Collantes, J.; Fadhil, N.; Montelione, G. T.; Jin, S., Effect of mitochondrial uncouplers niclosamide ethanolamine (NEN) and oxyclozanide on hepatic metastasis of colon cancer. *Cell Death Dis* 2018, 9 (2), 215.

Jastroch, M.; Divakaruni, A. S.; Mookerjee, S.; Treberg, J. R.; Brand, M. D., Mitochondrial proton and electron leaks. *Essays Biochem* 2010, 47, 53-67.

Xie, N.; Zhang, L.; Gao, W.; Huang, C.; Huber, P. E.; Zhou, X.; Li, C.; Shen, G.; Zou, B., NAD(+) metabolism: pathophysiologic mechanisms and therapeutic potential. *Signal Transduct Target Ther* 2020, 5 (1), 227.

Hecht, G.; Gloxhuber, C., Studies on the tolerance of 5, 2'-dichloro-4'-nitrosalicylanilide ethanolamine salt. *Zeitschrift fur Tropenmedizin und Parasitologie* 1962, 13, 1-8.

Sheth, U., Mechanisms of anthelmintic action. Progress in Drug Research/Fortschritte der Arzneimittelforschung/Progrès des recherches pharmaceutiques 1975, 147-157.

Andrews, P.; Thyssen, J.; Lorke, D., The biology and toxicology of molluscicides, Bayluscide. *Pharmacology & therapeutics* 1982, 19 (2), 245-295.

Frayha, G. J.; Smyth, J.; Gobert, J. G.; Savel, J., The mechanisms of action of antiprotozoal and anthelmintic drugs in man. *General Pharmacology: The Vascular System* 1997, 28 (2), 273-299.

Patgiri, A.; Skinner, O. S.; Miyazaki, Y.; Schleifer, G.; Marutani, E.; Shah, H.; Sharma, R.; Goodman, R. P.; To, T. L.; Robert Bao, X.; Ichinose, F.; Zapol, W. M.; Mootha, V. K., An engineered enzyme that targets circulating lactate to alleviate intracellular NADH:NAD(+) imbalance. *Nat Biotechnol* 2020, 38 (3), 309-313.

Kinnaird, A.; Zhao, S.; Wellen, K. E.; Michelakis, E. D., Metabolic control of epigenetics in cancer. *Nature Reviews Cancer* 2016, 16 (11), 694-707.

Pavlova, N. N.; Thompson, C. B., The Emerging Hallmarks of Cancer Metabolism. *Cell Metab* 2016, 23 (1), 27-47.

Strieder, V.; Lutz, W., E2F proteins regulate MYCN expression in neuroblastomas. *J Biol Chem* 2003, 278 (5), 2983-9.

Morris, J. P. t.; Yashinskie, J. J.; Koche, R.; Chandwani, R.; Tian, S.; Chen, C. C.; Baslan, T.; Marinkovic, Z. S.; Sanchez-Rivera, F. J.; Leach, S. D.; Carmona-Fontaine, C.; Thompson, C. B.; Finley, L. W. S.; Lowe, S. W., alpha-Ketoglutarate links p53 to cell fate during tumour suppression. *Nature* 2019, 573 (7775), 595-599.

Tran, T. Q.; Hanse, E. A.; Habowski, A. N.; Li, H.; Gabra, M. B. I.; Yang, Y.; Lowman, X. H.; Ooi, A. M.; Liao, S. Y.; Edwards, R. A.; Waterman, M. L.; Kong, M., alpha-Ketoglutarate attenuates Wnt signaling and drives differentiation in colorectal cancer. *Nat Cancer* 2020, 1 (3), 345-358.

Metallo, C. M.; Gameiro, P. A.; Bell, E. L.; Mattaini, K. R.; Yang, J.; Hiller, K.; Jewell, C. M.; Johnson, Z. R.; Irvine, D. J.; Guarente, L.; Kelleher, J. K.; Vander Heiden, M. G.; Iliopoulos, O.; Stephanopoulos, G., Reductive glutamine metabolism by IDH1 mediates lipogenesis under hypoxia. *Nature* 2011, 481 (7381), 380-4.

Mullen, A. R.; Wheaton, W. W.; Jin, E. S.; Chen, P. H.; Sullivan, L. B.; Cheng, T.; Yang, Y.; Linehan, W. M.; Chandel, N. S.; DeBerardinis, R. J., Reductive carboxylation supports growth in tumour cells with defective mitochondria. *Nature* 2011, 481 (7381), 385-8.

Wise, D. R.; Ward, P. S.; Shay, J. E.; Cross, J. R.; Gruber, J. J.; Sachdeva, U. M.; Platt, J. M.; DeMatteo, R. G.; Simon, M. C.; Thompson, C. B., Hypoxia promotes isocitrate dehydrogenase-dependent carboxylation of alpha-ketoglutarate to citrate to support cell growth and viability. *Proc Natl Acad Sci USA* 2011, 108 (49), 19611-6.

Nordsmark, M.; Overgaard, M.; Overgaard, J., Pretreatment oxygenation predicts radiation response in advanced squamous cell carcinoma of the head and neck. *Radiother Oncol* 1996, 41 (1), 31-9.

Hockel, M.; Schlenger, K.; Mitze, M.; Schaffer, U.; Vaupel, P., Hypoxia and Radiation Response in Human Tumors. *Seminars in radiation oncology* 1996, 6 (1), 3-9.

Teicher, B. A.; Holden, S. A.; al-Achi, A.; Herman, T. S., Classification of antineoplastic treatments by their differential toxicity toward putative oxygenated and hypoxic tumor subpopulations in vivo in the FSaIIC murine fibrosarcoma. *Cancer research* 1990, 50 (11), 3339-44.

Wike-Hooley, J. L.; Haveman, J.; Reinhold, H. S., The relevance of tumour pH to the treatment of malignant disease. *Radiother Oncol* 1984, 2 (4), 343-66.

Sutherland, R. M.; Eddy, H. A.; Bareham, B.; Reich, K.; Vanantwerp, D., Resistance to adriamycin in multicellular spheroids. *International journal of radiation oncology, biology, physics* 1979, 5 (8), 1225-30.

Intlekofer, A. M.; Wang, B.; Liu, H.; Shah, H.; Carmona-Fontaine, C.; Rustenburg, A. S.; Salah, S.; Gunner, M. R.; Chodera, J. D.; Cross, J. R.; Thompson, C. B., L-2-Hydroxyglutarate production arises from noncanonical enzyme function at acidic pH. *Nat Chem Biol* 2017, 13 (5), 494-500.

Tao, H.; Zhang, Y.; Zeng, X.; Shulman, G. I.; Jin, S., Niclosamide ethanolamine-induced mild mitochondrial uncoupling improves diabetic symptoms in mice. *Nat Med* 2014, 20 (11), 1263-9.

Niemas-Teshiba, R.; Matsuno, R.; Wang, L. L.; Tang, X. X.; Chiu, B.; Zeki, J.; Coburn, J.; Ornell, K.; Naranjo, A.; Van Ryn, C., MYC-family protein overexpression and prominent nucleolar formation represent prognostic indicators and potential therapeutic targets for aggressive high-MKI neuroblastomas: a report from the children's oncology group. *Oncotarget* 2018, 9 (5), 6416.

Gomez, S.; Castellano, G.; Mayol, G.; Sunol, M.; Queiros, A.; Bibikova, M.; Nazor, K. L.; Loring, J. F.; Lemos, I.; Rodriguez, E.; de Torres, C.; Mora, J.; Martin-Subero, J. I.; Lavarino, C., DNA methylation fingerprint of neuroblastoma reveals new biological and clinical insights. *Epigenomics* 2015, 7 (7), 1137-53.

Reynolds, P. R.; Schaalje, G. B.; Seegmiller, R. E., Combination therapy with folic acid and methionine in the prevention of retinoic acid-induced cleft palate in mice. *Birth Defects Res A Clin Mol Teratol* 2003, 67 (3), 168-73.

Finklestein, J. Z.; Krailo, M. D.; Lenarsky, C.; Ladisch, S.; Blair, G. K.; Reynolds, C. P.; Sitarz, A. L.; Hammond, G. D., 13-cis-retinoic acid (NSC 122758) in the treatment of children with metastatic neuroblastoma unresponsive to conventional chemotherapy: report from the Childrens Cancer Study Group. *Med Pediatr Oncol* 1992, 20 (4), 307-11.

Smith, M. A.; Adamson, P. C.; Balis, F. M.; Feusner, J.; Aronson, L.; Murphy, R. F.; Horowitz, M. E.; Reaman, G.; Hammond, G. D.; Fenton, R. M.; et al., Phase I and pharmacokinetic evaluation of all-trans-retinoic acid in pediatric patients with cancer. *J Clin Oncol* 1992, 10 (11), 1666-73.

Villablanca, J. G.; Khan, A. A.; Avramis, V. I.; Seeger, R. C.; Matthay, K. K.; Ramsay, N. K.; Reynolds, C. P., Phase I trial of 13-cis-retinoic acid in children with neuroblastoma following bone marrow transplantation. *J Clin Oncol* 1995, 13 (4), 894-901.

Bartolucci, S.; Estenoz, M.; de Franciscis, V.; Carpinelli, P.; Colucci, G. L.; Augusti Tocco, G.; Rossi, M., Effect of cytidine analogs on cell growth and differentiation on a human neuroblastoma line. *Cell Biophys* 1989, 15 (1-2), 67-77.

Bartolucci, S.; Estenoz, M.; Longo, A.; Santoro, B.; Momparler, R. L.; Rossi, M.; Augusti-Tocco, G., 5-Aza-2'-deoxycytidine as inducer of differentiation and growth inhibition in mouse neuroblastoma cells. *Cell Differ Dev* 1989, 27 (1), 47-55.

Westerlund, I.; Shi, Y.; Toskas, K.; Fell, S. M.; Li, S.; Surova, O.; Sodersten, E.; Kogner, P.; Nyman, U.; Schlisio, S.; Holmberg, J., Combined epigenetic and differentiation-based treatment inhibits neuroblastoma tumor growth and links HIF2alpha to tumor suppression. *Proc Natl Acad Sci USA* 2017, 114 (30), E6137-E6146.

Warburg, O.; Wind, F.; Negelein, E., The Metabolism of Tumors in the Body. *The Journal of general physiology* 1927, 8 (6), 519-30.

Warburg, O., On the origin of cancer cells. *Science* 1956, 123 (3191), 309-14.

Dang, L.; White, D. W.; Gross, S.; Bennett, B. D.; Bittinger, M. A.; Driggers, E. M.; Fantin, V. R.; Jang, H. G.; Jin, S.; Keenan, M. C.; Marks, K. M.; Prins, R. M.; Ward, P. S.; Yen, K. E.; Liau, L. M.; Rabinowitz, J. D.; Cantley, L. C.; Thompson, C. B.; Vander Heiden, M. G.; Su, S. M., Cancer-associated IDH1 mutations produce 2-hydroxyglutarate. *Nature* 2009, 462 (7274), 739-44.

Ward, P. S.; Patel, J.; Wise, D. R.; Abdel-Wahab, O.; Bennett, B. D.; Coller, H. A.; Cross, J. R.; Fantin, V. R.; Hedvat, C. V.; Perl, A. E.; Rabinowitz, J. D.; Carroll, M.; Su, S. M.; Sharp, K. A.; Levine, R. L.; Thompson, C. B., The common feature of leukemia-associated IDH1 and IDH2 mutations is a neomorphic enzyme activity converting alpha-ketoglutarate to 2-hydroxyglutarate. *Cancer Cell* 2010, 17 (3), 225-34.

Xu, W.; Yang, H.; Liu, Y.; Yang, Y.; Wang, P.; Kim, S. H.; Ito, S.; Yang, C.; Wang, P.; Xiao, M. T.; Liu, L. X.; Jiang, W. Q.; Liu, J.; Zhang, J. Y.; Wang, B.; Frye, S.; Zhang, Y.; Xu, Y. H.; Lei, Q. Y.; Guan, K. L.; Zhao, S. M.; Xiong, Y., Oncometabolite 2-Hydroxyglutarate Is a Competitive Inhibitor of alpha-Ketoglutarate-Dependent Dioxygenases. *Cancer Cell* 2011, 19 (1), 17-30.

Shim, E. H.; Livi, C. B.; Rakheja, D.; Tan, J.; Benson, D.; Parekh, V.; Kho, E. Y.; Ghosh, A. P.; Kirkman, R.; Velu, S.; Dutta, S.; Chenna, B.; Rea, S. L.; Mishur, R. J.; Li, Q.; Johnson-Pais, T. L.; Guo, L.; Bae, S.; Wei, S.; Block, K.; Sudarshan, S., L-2-Hydroxyglutarate: an epigenetic modifier and putative oncometabolite in renal cancer. *Cancer Discov* 2014, 4 (11), 1290-8.

Figueroa, M. E.; Abdel-Wahab, O.; Lu, C.; Ward, P. S.; Patel, J.; Shih, A.; Li, Y.; Bhagwat, N.; Vasanthakumar, A.; Fernandez, H. F.; Tallman, M. S.; Sun, Z.; Wolniak, K.; Peeters, J. K.; Liu, W.; Choe, S. E.; Fantin, V. R.; Paietta, E.; Lowenberg, B.; Licht, J. D.; Godley, L. A.; Delwel, R.; Valk, P. J.; Thompson, C. B.; Levine, R. L.; Melnick, A., Leukemic IDH1 and IDH2 mutations result in a hypermethylation phenotype, disrupt TET2 function, and impair hematopoietic differentiation. *Cancer Cell* 2010, 18 (6), 553-67.

Lu, C.; Ward, P. S.; Kapoor, G. S.; Rohle, D.; Turcan, S.; Abdel-Wahab, O.; Edwards, C. R.; Khanin, R.; Figueroa, M. E.; Melnick, A.; Wellen, K. E.; O'Rourke, D. M.; Berger, S. L.; Chan, T. A.; Levine, R. L.; Mellinghoff, I. K.; Thompson, C. B., IDH mutation impairs histone demethylation and results in a block to cell differentiation. *Nature* 2012, 483 (7390), 474-8.

Thiele, C. J.; Reynolds, C. P.; Israel, M. A., Decreased expression of N-myc precedes retinoic acid-induced morphological differentiation of human neuroblastoma. *Nature* 1985, 313 (6001), 404-6.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

What is claimed is:

1. A method for the therapeutic treatment of neuroblastoma in an individual, the method comprising:
   contacting a population of cancer cells with a mitochondrial uncoupler in a dose effective to increase differentiation of the cancer cells, wherein the mitochondrial uncoupler is selected from niclosamide ethanolamine (NEN), oxyclozanide and dinitrophenol (DNP).

2. The method of claim 1, wherein the neuroblastoma is retinoic acid resistant.

3. The method of claim 1, further comprising contacting the population of neuroblastoma cells with an effective dose of a retinoic acid.

4. The method of claim 3, wherein the combination of mitochondrial uncoupler and retinoic acid provides for a synergistic increase in differentiation of the neuroblastoma cells.

5. The method of claim 3, wherein the retinoic acid is selected from tretinoin, isotretinoin, and alitretinoin.

6. The method of claim 5, wherein the retinoic acid is isotretinoin.

7. The method of claim 3, wherein the retinoic acid is orally administered.

8. The method of claim 7, wherein the dose of retinoic acid is from 10 to 500 mg/m$^2$/day.

9. The method of claim 1, wherein the dose of NEN is from 1 to 500 mg/kg/day.

10. The method of claim 9, wherein NEN is orally administered.

11. The method of claim 1, further comprising an effective dose of an acetate supplementation agent and/or α-ketoglutarate.

12. The method of claim 11 wherein the acetate supplementation agent is glyceryltriacetate (GTA).

13. The method of claim 12, wherein the dose of GTA is from 25 to 1000 mg/kg/daily.

14. The method of claim 1, wherein the cancer is high risk neuroblastoma.

15. The method of claim 1, wherein the treatment provides for increased overall survival of the individual.

* * * * *

UNITED STATES PATENT AND TRADEMARK OFFICE
CERTIFICATE OF CORRECTION

| | | |
|---|---|---|
| PATENT NO. | : 11,918,550 B2 | Page 1 of 1 |
| APPLICATION NO. | : 17/542145 | |
| DATED | : March 5, 2024 | |
| INVENTOR(S) | : Jiangbin Ye | |

It is certified that error appears in the above-identified patent and that said Letters Patent is hereby corrected as shown below:

In the Specification

In Column 1, Line 14 through Line 20, please delete:
"STATEMENT REGARDING FEDERALLY SPONSORED RESEARCH
This invention was made with Government support under contracts HL157540 and OD029586 awarded by the National Institutes of Health. the government has certain rights in the invention."

Signed and Sealed this
Twenty-seventh Day of August, 2024

Katherine Kelly Vidal
*Director of the United States Patent and Trademark Office*